US008242134B2

(12) United States Patent
Khanzhin et al.

(10) Patent No.: US 8,242,134 B2
(45) Date of Patent: Aug. 14, 2012

(54) ISOQUINOLINONE DERIVATIVES AS NK3 ANTAGONISTS

(75) Inventors: Nikolay Khanzhin, Humlebaek (DK); Karsten Juhl, Greve (DK); Soren Moller Nielsen, Hillerod (DK); Klaus Baek Simonsen, Odense M (DK)

(73) Assignee: H. Lundbeck A/S, Valby (DK)

( * ) Notice: Subject to any disclaimer, the term of this patent is extended or adjusted under 35 U.S.C. 154(b) by 388 days.

(21) Appl. No.: 12/557,551

(22) Filed: Sep. 11, 2009

(65) Prior Publication Data

US 2010/0076016 A1    Mar. 25, 2010

Related U.S. Application Data

(60) Provisional application No. 61/096,993, filed on Sep. 15, 2008, provisional application No. 61/142,671, filed on Jan. 6, 2009.

(51) Int. Cl.
*A61K 31/47* (2006.01)
*C07D 217/22* (2006.01)

(52) U.S. Cl. ........................................ 514/309; 546/141

(58) Field of Classification Search ........................ None
See application file for complete search history.

(56) References Cited

U.S. PATENT DOCUMENTS

| 7,834,008 | B2 | 11/2010 | Kehler et al. |
| 2006/0142324 | A1 | 6/2006 | Yuan et al. |
| 2009/0143402 | A1 | 6/2009 | Kehler et al. |
| 2011/0130407 | A1 | 6/2011 | Khanzhin et al. |
| 2011/0130420 | A1 | 6/2011 | Khanzhin et al. |
| 2011/0288120 | A1 | 11/2011 | Khanzhin et al. |

FOREIGN PATENT DOCUMENTS

| WO | 9532948 A1 | 7/1995 |
| WO | 0031038 | 6/2000 |
| WO | 02083664 A1 | 10/2002 |
| WO | 2005014575 A1 | 2/2005 |
| WO | 2006050991 A | 5/2006 |
| WO | 2006050992 A1 | 5/2006 |
| WO | 2006120478 A2 | 11/2006 |
| WO | 2006130080 A2 | 12/2006 |
| WO | 2008131779 A1 | 11/2008 |
| WO | 2009/130240 A1 | 10/2009 |
| WO | 2009/156339 A1 | 12/2009 |
| WO | 2010/045948 A1 | 4/2010 |

OTHER PUBLICATIONS

Albert, J. S.; 2004, Neurokinin antagonists and their potential role in treating depression and other stress disorders, Expert Opin. Ther. Patents, 14(10):1421-1433.
Cogan D. A. et al., Jul. 16, 1999, Asymmetric Synthesis of Chiral Amines by Highly Diastereoselective 1,2-Additions of Organometallic Reagents to N-tert-Butanesulfinyl Imines, Tetrahedron, 29(55):8883-8904.

Daoui, Samira. et al., Jul. 1, 1998, Involvement of Tachykinin NK3 Receptors in Citric Acid-induced Cough and Bronchial Responses in Guinea Pigs, Am. .J. .Respir. Crit. Care. Med., 158(1):42-48.
Evangelista, S., 2005, Talnetant GlaxoSmithKline, Curr. Opion. .Invest. Drug., 6(7):717-721, 2005.
Fioramonti, J. et al., Aug. 2003, Intestinal anti-nociceptive behaviour of NK3 receptor antagonism in conscious rats: evidence to support a peripheral mechanism of action, Neurogastroenterol. Motil.,15(4):363-369, 2003.
Kemel, M. L. et al., Mar. 1, 2002, Facilitation of Endogenous Tachykinins of the NMDA-Evoked Release of Acetylcholine after Acute and Chronic Suppression of Dopaminergic Transmission of the Matrix of the Rat Striatum, J. Neurosci., 22(5):1929-1936.
Langlois, X. et al., Nov. 1, 2001, Use of the B-Imager for Rapid ex Vivo Autoradiography Exemplified with Central Nervous System Penetrating Neurokinin 3 Antagonists, J. Pharm. Exp. Ther., 299(2):712-717.
Liu, G., et al., Feb. 4, 1999, Synthesis of Enantiomerically Pure N-tert-Butanesulfinyl Imines (tert-Butanesulfinimines) by the Direct Condensation of tret-Butanesulfinamide with Aldehydes and Ketones, J. Org. Chem., 64(4):1278-1284.
Maubach, K. A. et al., 1998, Tachykinins May Modify Spontaneous Epileptiform Activity in the Rat Enthorhinal Cortex in Vitro by Activating Gabaergic Inhibition, Neuroscience., 83(4):1047-1062.
Mazelin, L., et al., 1998, Comparative Effects of Nonpeptide TachyKinin Receptor Antagonists of Experimental Gut Inflammation in Rats and Guinea-Pigs, Life Sci., 63(4):293-304.
Meltzer, et al., Jun. 2004, Placebo-Controlled Evaluation of Four Novel Compounds for the Treatment of Schizophrenia and Schizoaffective Disorder, Am. .J. Psychiatry, 161(6):975-984.
Modi, A. R. et al., Oct. 1979, Isopquinolones: Part IV—Synthesis of 3-Methyl, 3-Formyl & Other 3-Substituted N-Arylisoquinolones, Ind.J.Chem. Section B, 18B, 304-306.
Spooren et al, nk3 receptor antagonists: the next generation of antipsychotics?, Nature Reviews, 4(12):967-975, 2005.
Weix, D. J. and Ellman, A. E., 2005, (RS)-(+)-2-Methyl-2-Propanesulfinamide [tert-Butylsulfinamide], Organic Syntheses, 82:157.
Yip, J. and Chahl, L. A., Oct. 1997, et al, Localization of Fos-like immunoreactivity induced by the NK3 tachykinin receptor agonist, senktide, in the guinea-pig brain, Br. J. Phar., 122(4):715-722.
STN Registry No. 439140-06-4; Ambinter (Chemical Library); Jul. 17, 2002.
CAPLUS Registry No. 95311-84-5; retrieved from STN Accession No. 1985:132435 (Database Accn. No. 102:132435), Khaimova, M. et al., 1984 Synthesis of 1(2H)-isoquinolinone-3- and -4-carboxamides, Izvestiya Po Khimiya, vol. 17, No. 2, pp. 163-171 (XP-002553738).
CAS Registry No. 440662-17-9; AKos Screening Library Order No. AKG-K905-0165; Jul. 27, 2009 (XP-002553740).
CAS Registry No. 892265-30-4; AKos Screening Library Order No. AKG-C154-0190; Jul. 27, 2009 (XP-002553740).

(Continued)

*Primary Examiner* — Zinna Northington Davis
(74) *Attorney, Agent, or Firm* — Stephen G. Kalinchak; Mary Catherine Di Nunzio; Kitae Lim

(57) ABSTRACT

The invention relates to compounds useful in therapy, in particular in the treatment of psychosis, to compositions comprising said compounds, and to methods of treating diseases comprising the administration of said compounds.

31 Claims, No Drawings

OTHER PUBLICATIONS

CAS Registry No. 896626-62-3; ChemDiv Discovery Chemistry Collection Public Database Order No. C066-1497; Jul. 2, 2009 (XP-002553739).

CAS Registry No. 892264-55-0; ChemDiv Discovery Chemistry Collection Public Database Order No. C168-0204; Jul. 2, 2009 (XP-002553739).

CAS Registry No. 896627-38-6; ChemDiv Discovery Chemistry Collection Public Database Order No. C1066-3989; Jul. 2, 2009 (XP-002553739).

CAS Registry No. 896628-06-1; ChemDiv Discovery Chemistry Collection Public Database Order No. C066-4018; Jul. 2, 2009 (XP-002553739).

CAS Registry No. 892270-74-5; ChemDiv Discovery Chemistry Collection Public Database Order No. C168-0480; Jul. 2, 2009 (XP-002553739).

CAS Registry No. 896623-00-0; ChemDiv Discovery Chemistry Collection Public Database Order No. C066-1350; Jul. 2, 2009 (XP-002553739).

CAS Registry No. 896627-38-6; ChemDiv Discovery Chemistry Collection Public Database Order No. C066-3989; Jul. 2, 2009 (XP-002553739).

CAS Registry No. 8922969-97-5; ChemDiv Discovery Chemistry Collection Public Database Order No. C168-0466; Jul. 2, 2009 (XP-002553739).

CAS Registry No. 896623-00-0; ChemDiv Discovery Chemistry Collection Public Database Order No. C168-0204; Jul. 2, 2009 (XP-002553739).

Haimova, M., et al. 1984, Synthesis of 1(2H)-Isoquinolinone-3- and -4-Carboxamides, Communications of the Department of Chemistry, Bulgarian Academy of Sciences, 17(2):163-171.

Berge et al., 1977, "Pharmaceutical Salts" Journal of Pharmceutical Sciences, 66(1), pp. 1-19.

ISOQUINOLINONE DERIVATIVES AS NK3 ANTAGONISTS

CROSS-REFERENCE TO RELATED APPLICATIONS

The present application claims the benefit of priority under 35 U.S.C. §119(e) of U.S. Provisional Patent Application No. 61/096,993, filed Sep. 15, 2008 and U.S. Provisional Patent Application No. 61/142,671, filed Jan. 6, 2009, each of which are hereby incorporated by reference in their entirety.

FIELD OF THE INVENTION

The present invention relates to compounds useful in therapy, in particular in the treatment of psychosis, to compositions comprising said compounds, and to methods of treating diseases comprising the administration of said compounds.

BACKGROUND OF THE INVENTION

The currently approved antipsychotic drugs share the common feature of reducing dopamine signalling in the brain. This is achieved through either a dopamine D2 receptor antagonistic or partial agonistic effect. The first generation antipsychotics (also referred to as "typical") are often associated with extra-pyramidal side effects for which reason the use of these agents has diminished. Second generation or "atypical" antipsychotics in addition to the D2 receptor affinity have affinity to the serotonin receptor 2A (5-$HT_{2A}$). Some atypical antipsychotics in addition have affinity for the 5-$HT_{2C}$, 5-$HT_6$, or 5-$HT_7$ receptors. Atypical antipsychotics give rise to fewer extra-pyramidal side effects, but are still hampered by weight gain and $QT_C$ effects. Examples of atypicals are clozapine, olanzapine and risperidone.

More recently, neurokinin receptors have been suggested as targets for CNS diseases [Albert, *Expert Opin. Ther. Patents*, 14, 1421-1433, 2004]. Neurokinins (or tachykinins) are a family of neuropeptides which include substance P (SP), neurokinin A (NKA), and neurokinin B (NKB). The biological effects of these substances are primarily effected through binding to and activation of the three neurokinin receptors NK1, NK2, and NK3. Although some cross reactivity probably exists, SP has the highest affinity and is believed to be the endogenous ligand for NK1. Similarly, NKA is believed to be the endogenous ligand for NK2, and for NKB is believed to be the endogenous ligand for NK3.

NK3 is primarily expressed centrally in regions including cortical regions, such as frontal, parietal and cingulated cortex; nuclei of the amygdale, such as the basal, central and lateral nuclei; the hippocampus; and mesencephalon structures, such as ventral tegmental area, substantia nigra pars compacta, and dorsal raphe nuclei [Spooren et al, *Nature Reviews*, 4, 967-975, 2005]. The NK3 receptor is expressed on dopaminergic neurons, and Spooren et al has suggested that the antipsychotic effects of NK3 antagonists are mediated by an inhibition of the dopamine tone, particularly at the D2 receptor combined with a reduction of the serotonergic tone, particularly at the 5-$HT_{2A}$ receptor.

Two structurally distinct NK3 antagonists, namely talnetant and osanetant, have been clinically tested for antipsychotic, and in particular antischizophrenic effects.

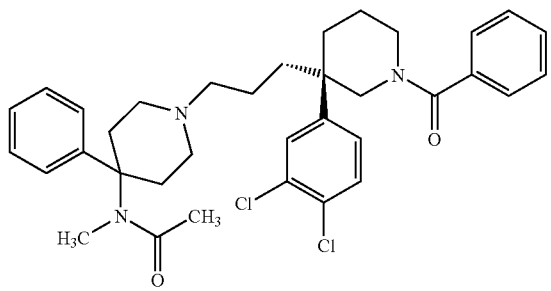

Osanetant

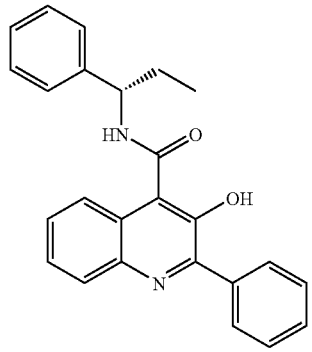

Talnetant

Osanetant proved superior to placebo in clinical trials, in particular on positive symptoms of psychosis, i.e. delusions, hallucinations and paranoia [*Am. J. Psychiatry*, 161, 2004, 975-984]. Similarly, talnetant has been shown in clinical trials to ameliorate the cognitive behaviour of schizophrenics [*Curr. Opion. Invest. Drug*, 6, 717-721, 2005]. Nevertheless, both compounds are hampered by poor pharmacokinetic and pharmacodynamic properties including poor solubility, poor bioavailability, relatively high clearance, and poor blood-brain barrier penetration [*Nature reviews*, 4, 967-975, 2005]. These results lend support to the notion that the NK3 receptor is a promising target for the treatment of e.g. psychosis, however emphasizing the need for identifying compounds with adequate pharmacokinetic and pharmacodynamic properties.

WO95/32948 discloses a range of quinoline derivatives, including talnetant, as NK3 antagonists.

More recently, WO 2006/130080 discloses compounds having the core structure

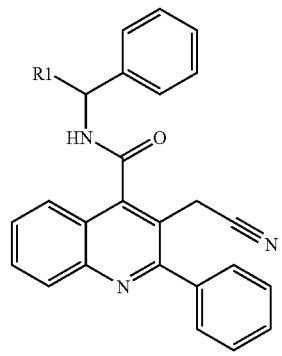

which compounds are said to be NK3 antagonists; and WO 2006/050991 and WO 2006/050992 disclose further quinolinecarboxamides derivatives, which derivatives are said to be NK3 antagonists.

WO 2005/014575 discloses compounds of the formula

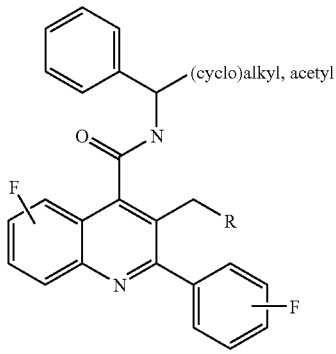

wherein R represents N-containing heterocycles, i.e. pyrazolyl, triazolyl and tetrazolyl.

*Ind. J. Chem. Section B,* 18B, 304-306, 1979 discloses a study on the synthesis of compounds with the following core structure

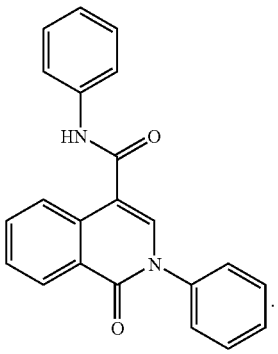

The chemical supplier Ambinter provides a compound of the structure

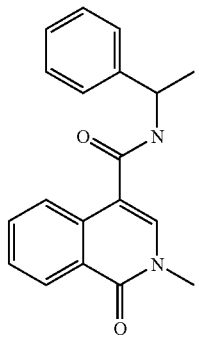

and with the chemical name 2-methyl-1-oxo-1,2-dihydro-isoquinoline-4-carboxylic acid (1-phenyl-ethyl)-amide.

SUMMARY OF THE INVENTION

The present inventors have surprisingly found that certain isoquinolinone derivatives are potent NK3 antagonists which may as such be used in the treatment of e.g. psychosis. Accordingly, in one embodiment the invention relates to compounds of formula I

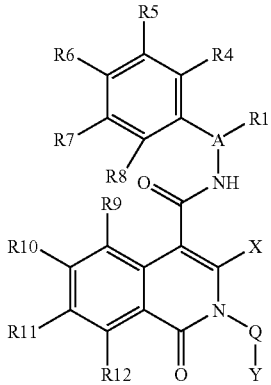

wherein A represents N, CH or $CR^1$;
each $R^1$ independently represents hydrogen, $C_{1-6}$alkyl, $C_{2-6}$alkenyl, $C_{2-6}$alkynyl, —C(O)—$C_{1-6}$alkyl, —C(O)—$C_{2-6}$alkenyl, —C(O)—$C_{2-6}$alkynyl, —C(O)—O—$C_{1-6}$alkyl, —C(O)—O—$C_{2-6}$alkenyl, —C(O)—O—$C_{2-6}$alkynyl or phenyl, wherein said phenyl, $C_{1-6}$alkyl, $C_{2-6}$alkenyl or $C_{2-6}$alkynyl is optionally substituted with one or more substituents selected from halogen, hydroxyl, halo$C_{1-6}$alkyl, nitro, $C_{1-6}$alkoxy, and $NR^2R^3$;
X represents hydrogen, $C_{1-6}$alkyl optionally substituted with F, or —$CR^aR^b$—X',
wherein X' represents a monocyclic saturated moiety having 5-6 ring atoms one of which is N and wherein one or two additional ring atom may be a hetero atom selected from N, O and S, which monocyclic ring may be substituted with one or more substituent W, wherein W is selected from $C_{1-6}$alkyl, $C_{2-6}$alkenyl, $C_{2-6}$alkynyl, $C_{1-6}$haloalkyl or (=O);
$R^a$ and $R^b$ each individually represent hydrogen, —$CH_3$ or halogen;
Q represents a bond, —$CH_2$—, —NH—, or —O—;
Y represents $C_{1-6}$alkyl, $C_{2-6}$alkenyl or $C_{2-6}$alkynyl, wherein said alkyl, alkenyl or alkynyl may be substituted with one or more substituents P, wherein P is selected from halogen, hydroxy, $C_{1-6}$alkoxy, cyano, —S—$C_{1-6}$alkyl, and a monocyclic saturated moiety having 5-6 ring atoms one ring atom of which may be N and the rest is C; or Y may represent a monocyclic saturated moiety having 4-6 ring atoms, wherein 1 of said ring atoms may be selected from N and O, the rest being C, and which monocyclic saturated moiety may be substituted with one or more substituents Z, wherein Z is selected from $C_{1-6}$alkyl, $C_{2-6}$alkenyl, $C_{2-6}$alkynyl, (=O), C(O)H, —C(O)—$C_{1-6}$alkyl, halogen, $C_{1-6}$alkoxy, $C_{1-6}$hydroxyalkyl and hydroxy;
wherein each of $R^2$ and $R^3$ independently represents hydrogen, $C_{1-6}$alkyl, $C_{2-6}$alkenyl, $C_{2-6}$alkynyl, hydroxy$C_{1-6}$alkyl, or halo$C_{1-6}$alkyl;
each of $R^4$-$R^8$ and $R^9$-$R^{12}$ independently represent hydrogen, $C_{1-6}$alkyl, $C_{2-6}$alkenyl, $C_{2-6}$alkynyl, halogen, $NR^2R^3$, hydroxy, cyano, nitro, $C_{1-6}$alkoxy, halo$C_{1-6}$alkyl or hydroxy$C_{1-6}$alkyl;
provided said compound is different from 2-methyl-1-oxo-1,2-dihydro-isoquinoline-4-carboxyl is acid (1-phenyl-ethyl)-amide;
and pharmaceutically acceptable salts thereof.

In one embodiment, the invention relates to the use of a compound of formula I and pharmaceutically acceptable salts thereof in therapy.

In one embodiment, the invention relates to a pharmaceutical composition comprising compounds of formula I and pharmaceutically acceptable salts in combination with one or more pharmaceutically acceptable carrier or excipient.

In one embodiment, the invention relates to the use of a compound of formula I and pharmaceutically acceptable salts in the manufacture of medicaments.

In one embodiment, the invention relates to a compound of formula I and pharmaceutically acceptable salts for use in the treatment of diseases.

In one embodiment, the invention relates to a method a treatment, said method comprising the administration of a therapeutically effective amount of compound I and pharmaceutically acceptable salts to a patient in need thereof.

In one embodiment, the invention relates to a method of determining binding occupancy of an NK3 ligand comprising the use of an effective amount of a compound of formula I' wherein each C may be the $^{11}C$ isotope and each F may be the $^{18}F$ isotope, wherein said compound comprises at least one of said isotopes; and pharmaceutically acceptable salts thereof.

DEFINITIONS

In the present context, "alkyl" is intended to indicate a straight, branched and/or cyclic saturated hydrocarbon. In particular "$C_{1-6}$alkyl" is intended to indicate such hydrocarbon having 1, 2, 3, 4, 5, or 6 carbon atoms. Examples of $C_{1-6}$alkyl include methyl, ethyl, propyl, butyl, pentyl, hexyl, cyclopropyl, cyclobutyl, cyclopentyl, cyclohexyl, 2-methylpropyl, tert.-butyl, and cyclopropylmethyl.

In the present context, "alkenyl" is intended to indicate a non-aromatic, straight, branched and/or cyclic hydrocarbon comprising at least one carbon-carbon double bond. In particular "$C_{2-6}$alkenyl" is intended to indicate such hydrocarbon having 2, 3, 4, 5, or 6 carbon atoms. Examples of $C_{2-6}$alkenyl include ethenyl, 1-propenyl, 2-propenyl, 1-butenyl, 2-butenyl, 3-butenyl, and cyclohexenyl.

In the present context, "alkynyl" is intended to indicate a non-aromatic, straight, branched and/or cyclic hydrocarbon comprising at least one carbon-carbon triple bond and optionally also one or more carbon-carbon double bonds. In particular "$C_{2-6}$alkynyl" is intended to indicate such hydrocarbon having 2, 3, 4, 5, or 6 carbon atoms. Examples of $C_{2-6}$alkynyl include ethynyl, 1-propynyl, 2-propynyl, 1-butynyl, 2-butynyl, 3-butynyl and 5-but-1-en-3-ynyl.

In the present context "halogen" is intended to indicate members of the 7$^{th}$ group of the periodic system, e.g. fluoro, chloro, bromo, and iodo.

In the present context, "alkoxy" is intended to indicate a moiety of the formula —OR', wherein R' indicates alkyl as defined above. In particular "$C_{1-6}$alkoxy" is intended to indicate such moiety wherein the alkyl part has 1, 2, 3, 4, 5, or 6 carbon atoms.

In the present context, haloalkyl is intended to indicate an alkyl as defined above substituted with one or more halogens. In particular, halo$C_{1-6}$alkyl is intended to indicate a moiety wherein the alkyl part has 1, 2, 3, 4, 5 or 6 carbon atoms. One example of haloalkyl is trifluoromethyl.

In the present context, pharmaceutically acceptable salts include pharmaceutical acceptable acid addition salts, pharmaceutically acceptable metal salts, ammonium and alkylated ammonium salts. Acid addition salts include salts of inorganic acids as well as organic acids.

Examples of suitable inorganic acids include hydrochloric, hydrobromic, hydroiodic, phosphoric, sulfuric, sulfamic, nitric acids and the like.

Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

In the present context, a "ring atom" is intended to indicate the atoms constituting a ring, and ring atoms are selected from C, N, O and S. As an example, benzene and toluene both have 6 carbons as ring atoms whereas pyridine has 5 carbons and 1 nitrogen as ring atoms.

In the present context, a "mono-cyclic moiety" is intended to indicate a ring formed structure comprising only one ring.

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspects of the invention. The patient to be treated is preferably a mammal, in particular a human being.

In the present context, the term "binding occupancy" indicates the fraction of target binding sites occupied by a particular compound.

In the present context, the term "PET ligand" indicates a high affinity ligand for the relevant target with good distribution to the relevant compartment, in the present context the CNS. Said ligand is radiolabeled with a short-lived radioactive tracer isotope, preferably $^{11}C$ or $^{18}F$, that undergoes positron emission decay.

In the present context, the term "plasma free fraction" indicates the fraction of a compound in blood plasma that is not bound to plasma proteins.

In the present context, "blood-brain barrier" (or BBB) indicates a physiological barrier formed by an endothelial cell layer. Said barrier prevents some substances, such as certain drugs from entering brain tissue.

In the present context, P-gp (P-glycoprotein) indicates an efflux transporter located in the BBB. Other names for P-gp are MDR1 and ABCB1.

DETAILED DESCRIPTION OF THE INVENTION

In one embodiment, the invention provides compounds according to formula I

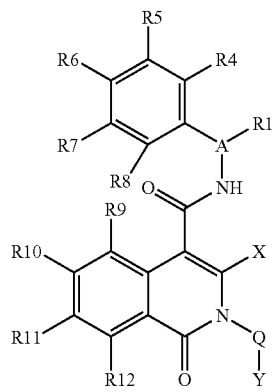

wherein A represents N, CH or $CR^1$;
each R' independently represents hydrogen, $C_{1-6}$alkyl, $C_{2-6}$alkenyl, $C_{2-6}$alkynyl, —C(O)—$C_{1-6}$alkyl, —C(O)—$C_{2-6}$alkenyl, —C(O)—$C_{2-6}$alkynyl, —C(O)—O—$C_{1-6}$alkyl, —C(O)—$C_{2-6}$alkenyl, —C(O)—O—$C_{2-6}$alkynyl or phenyl, wherein said phenyl, $C_{1-6}$alkyl, $C_{2-6}$alkenyl or $C_{2-6}$alkynyl is optionally substituted with one or more substituents selected from halogen, hydroxyl, halo$C_{1-6}$alkyl, nitro, $C_{1-6}$alkoxy, and $NR^2R^3$;
X represents hydrogen, $C_{1-6}$alkyl optionally substituted with F, or —$CR^aR^b$—X',
wherein X' represents a monocyclic saturated moiety having 5-6 ring atoms one of which is N and wherein one or two additional ring atom may be a hetero atom selected from N, O and S, which monocyclic ring may be substituted with one or more substituents W, wherein W is selected from $C_{1-6}$alkyl, $C_{2-6}$alkenyl, $C_{2-6}$alkynyl, $C_{1-6}$haloalkyl or (=O);
$R^a$ and $R^b$ each individually represent hydrogen, —$CH_3$ or halogen;
Q represents a bond, —$CH_2$—, —NH—, or —O—;
Y represents $C_{1-6}$alkyl, $C_{2-6}$alkenyl or $C_{2-6}$alkynyl, wherein said alkyl, alkenyl or alkynyl may be substituted with one or more substituents P, wherein P is selected from halogen, hydroxy, $C_{1-6}$alkoxy, cyano, —S—$C_{1-6}$alkyl, and a monocyclic saturated moiety having 5-6 ring atoms one ring atom of which may be N and the rest is C; or Y may represent a monocyclic saturated moiety having 4-6 ring atoms, wherein 1 of said ring atoms may be selected from N and O, the rest being C, and which monocyclic saturated moiety may be substituted with one or more substituents Z, wherein Z is selected from $C_{1-6}$alkyl, $C_{2-6}$alkenyl, $C_{2-6}$alkynyl, (=O), C(O)H, halogen, $C_{1-6}$alkoxy, $C_{1-6}$hydroxyalkyl and hydroxy; wherein each of $R^2$ and $R^3$ independently represents hydrogen, $C_{1-6}$alkyl, $C_{2-6}$alkenyl, $C_{2-6}$alkynyl, hydroxy$C_{1-6}$alkyl, or halo$C_{1-6}$alkyl;
each of $R^4$-$R^8$ and $R^9$-$R^{12}$ independently represent hydrogen, $C_{1-6}$alkyl, $C_{2-6}$alkenyl, $C_{2-6}$alkynyl, halogen, $NR^2R^3$, hydroxy, cyano, nitro, $C_{1-6}$alkoxy, halo$C_{1-6}$alkyl or hydroxy$C_{1-6}$alkyl;
provided said compound is different from 2-methyl-1-oxo-1,2-dihydro-isoquinoline-4-carboxylic acid 1-phenyl-ethyl)-amide;
and pharmaceutically acceptable salts thereof (i.e. the compounds of the present invention).

Example of such mono-cyclic saturated moieties having 5-6 ring atoms one of which is N and wherein one or two additional ring atoms may be a hetero atom selected from N, O, S include piperazinyl, pyrrolidinyl, imidazolidinyl, pyrrazolidinyl, piperdyl, morpholinyl, and thiomorpholinyl.

Examples of such monocyclic saturated moiety having 5-6 ring atoms one ring atom of which may be N and the rest is C include cyclopropyl, cyclohexyl, pyrrolidinyl and piperidyl.

Examples of such monocyclic saturated moiety having 4-6 ring atoms, wherein 1 of said ring atoms may be selected from N and O, the rest being C include cyclopropyl, cyclohexyl, pyrrolidinyl, piperidyl, tetrahydrofuranyl and tetrahydropyranyl.

In one embodiment, A represents CH.

In one embodiment, $R^1$ represents $C_{1-6}$alkyl, in particular ethyl, cyclopropyl or cyclobutyl.

In one embodiment, X represents H, methyl optionally substituted with F, or —$CH_2$—X', wherein X' represents a monocyclic saturated moiety selected from piperazinyl and pyrrolidinyl, wherein said monocyclic moiety may be substituted with one or more substituents W, wherein W is selected from $C_{1-6}$alkyl and (=O).

In one embodiment, Q represents —$CH_2$— and Y represents $C_{1-4}$alkyl, $C_{2-4}$alkenyl or $C_{2-4}$alkynyl, wherein P is selected from halogen, hydroxyl, —S—$CH_3$ and cyano. Particular examples of $C_{1-4}$alkyl include methyl, ethyl propyl, cyclopropyl, cyclobutyl, 2-methyl-propyl and tert.-butyl; Particular examples of $C_{2-4}$alkenyl include ethenyl, 1-propenyl and 2-propenyl; Particular examples of $C_{2-4}$alkynyl include ethynyl, 1-propenyl and 2-propenyl.

In one embodiment, Q represents —$CH_2$— and Y represents a monocyclic saturated moiety having 4-6 ring atoms, wherein 1 of said ring atoms may be selected from N and O, the rest being C, and which monocyclic saturated moiety may be substituted with one or more substituents Z, wherein Z is selected from $C_{1-6}$alkyl, (=O), C(O)H, —C(O)—O—$C_{1-6}$alkyl, halogen, $C_{1-6}$alkoxy, $C_{1-6}$hydroxyalkyl and hydroxy.

In one embodiment, Q represents —NH— and Y represents $C_{1-6}$alkyl, wherein P is halogen, or alternatively Y represents a monocyclic moiety having 4, 5 or 6 ring atoms, which ring atoms are selected from C. Particular examples of Y include methyl, ethyl, propyl, 1-methyl-ethyl, 2-methyl-propyl and butyl.

In one embodiment, Q represents —O— and Y represents $C_{1-4}$alkyl. Particular examples of $C_{1-4}$alkyl include methyl, ethyl propyl, cyclopropyl, cyclobutyl, 2-methyl-propyl and tert.-butyl.

In one embodiment, Q represents a bond and Y represents a monocyclic saturated moiety having 4-6 ring atoms, wherein one of said ring atoms may be selected from N and O, the rest being C, and which monocyclic saturated moiety may be substituted with one or more substituents Z, wherein Z is selected from $C_{1-6}$alkyl, (=O), halogen, and hydroxy.

In one embodiment, each of $R^4$-$R^8$ independently represents hydrogen or halogen; in particular, $R^7$ represents halogen and $R^4$, $R^5$ and $R^8$ represent hydrogen.

In one embodiment, all of $R^4$-$R^8$ represents hydrogen.

In one embodiment, each of $R^9$-$R^{12}$ independently represents hydrogen of halogen; in particular, $R^{12}$ represents halogen and $R^9$-$R^{11}$ represent hydrogen.

In one embodiment, all of $R^9$-$R^{12}$ represent hydrogen.

In one embodiment, the compounds of the invention are defined further by formula I' below

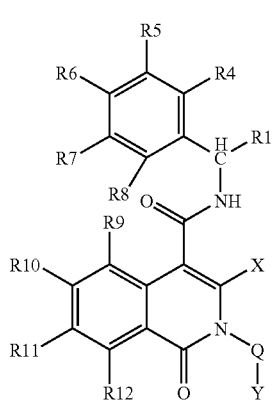

[I']

wherein $R^1$ represents $C_{1-6}$alkyl;
X represents hydrogen, $C_{1-6}$ alkyl optionally substituted with F, or —$CR^aR^b$—X',
wherein X' represents a monocyclic saturated moiety having 5-6 ring atoms one of which is N and wherein one or two additional ring atom may be a hetero atom selected from N, O and S, selected from piperazinyl and pyrrolidinyl, which monocyclic ring may be substituted with one or more substituent W, wherein W is selected from $C_{1-6}$alkyl or (=O);
$R^a$ and $R^b$ each individually represent hydrogen, —$CH_3$ or halogen;
Q represents a bond, —$CH_2$—, —NH— or —O—;
Y represents $C_{1-6}$alkyl, $C_{2-6}$alkenyl or $C_{2-6}$alkynyl, wherein said alkyl, alkenyl or alkynyl may be substituted with one or more substituents P, wherein P is selected from halogen, hydroxy, $C_{1-6}$alkoxy, cyano, —S—$C_{1-6}$alkyl, and a monocyclic saturated moiety having 5-6 ring atoms, one ring atom of which may be N and the rest is C; or alternatively Y may represent a monocyclic saturated moiety having 4-6 ring atoms, wherein one of said ring atoms may be selected from N and O, the rest being C, and which monocyclic saturated moiety may be substituted with one or more substituents Z, wherein Z is selected from $C_{1-6}$alkyl, (=O), C(O)H, —C(O)—O—$C_{1-6}$alkyl, halogen, $C_{1-6}$alkoxy, $C_{1-6}$hydroxyalkyl and hydroxy;
each of $R^4$-$R^8$ and $R^9$-$R^{12}$ independently represent hydrogen, halogen, $C_{1-6}$alkoxy or $C_{1-6}$haloalkyl;
and pharmaceutically acceptable salts thereof.

In one embodiment relating for formula I', $R^1$ represents ethyl, cyclopropyl or cyclobutyl; X represents $C_{1-6}$alkyl optionally substituted with F, or —$CH_2$—X', wherein X' represents a monocyclic saturated moiety having 5-6 ring atoms one of which is N and wherein one or two additional ring atom may be a hetero atom selected from N, O and S, selected from piperazinyl and pyrrolidinyl, which monocyclic ring may be substituted with one or more substituent W, wherein W is selected from $C_{1-6}$alkyl or (=O); Q represents —$CH_2$— or —NH—; Y represents $C_{1-6}$alkyl, $C_{2-6}$alkenyl or $C_{2-6}$alkynyl all of which may optionally be substituted with up to three halogens, or alternatively Y represent a monocyclic saturated moiety having 4-6 ring atoms, wherein 1 of said ring atoms may be selected from N and O, the rest being C, and which monocyclic saturated moiety may be substituted with one or more substituents Z, wherein Z is selected from $C_{1-6}$alkyl; and each of $R^4$-$R^8$ and $R^9$-$R^{12}$ independently represents hydrogen, halogen, $C_{1-6}$alkoxy or $C_{1-6}$haloalkyl, and in particular each of $R^4$-$R^8$ and $R^9$-$R^{12}$ independently represents hydrogen or halogen. In a further embodiment within this embodiment, $R^7$ represents halogen, $R^5$, $R^6$ and $R^8$ represent hydrogen.

In one embodiment relating to formula I' $R^1$ represents ethyl, cyclopropyl or cyclobutyl; X represents $C_{1-6}$alkyl optionally substituted with F, or —$CH_2$—X', wherein X' represents a monocyclic saturated moiety having 5-6 ring atoms one of which is N and wherein one or two additional ring atom may be a hetero atom selected from N, O and S, selected from piperazinyl and pyrrolidinyl, which monocyclic ring may be substituted with one or more substituent W, wherein W is selected from $C_{1-6}$alkyl or (=O); Q represents —$CH_2$— or —NH—; Y represents $C_{1-4}$alkyl, $C_{2-4}$alkenyl or $C_{2-4}$alkynyl all of which may optionally be substituted with up to three halogens;
each of $R^4$-$R^8$ and $R^9$-$R^{12}$ independently represents hydrogen or halogen, and in particular $R^7$ and $R^{12}$ each independently represents halogen and $R^4$-$R^6$, $R^8$ and $R^9$-$R^{11}$ represent hydrogen. Alternatively, $R^7$ is halogen and $R^4$-$R^8$ and $R^9$-$R^{11}$ are hydrogen. Particular examples of Y as $C_{1-4}$alkyl include methyl, ethyl propyl, cyclopropyl, cyclobutyl, 2-methyl-propyl and tert.-butyl; particular examples of Y as $C_{2-4}$alkenyl include ethenyl, 1-propenyl and 2-propenyl; particular examples of Y as $C_{2-4}$alkynyl include ethynyl, 1-propenyl and 2-propenyl.

In one embodiment relating to formula I' $R^1$ represents ethyl, cyclopropyl or cyclobutyl; X represents $C_{1-6}$alkyl optionally substituted with F; Q represents —NH—; Y represents $C_{1-4}$alkyl, which may optionally be substituted with up to three halogens;
each of $R^4$-$R^8$ and $R^9$-$R^{12}$ independently represents hydrogen or halogen, and in particular, $R^7$ is halogen and $R^4$-$R^6$, $R^8$ and $R^9$-$R^{11}$ are hydrogen. Particular examples of Y as $C_{1-4}$alkyl include methyl, ethyl propyl, cyclopropyl, cyclobutyl, 2-methyl-propyl and tert.-butyl.

In one embodiment, the invention provides compounds selected from the list
1a  2-Cyclopentyl-3-methyl-1-oxo-1,2-dihydro-isoquinoline-4-carboxylic acid ((S)-1-phenyl-propyl)-amide
1b  2-Cyclopropyl-3-methyl-1-oxo-1,2-dihydro-isoquinoline-4-carboxylic acid ((S)-1-phenyl-propyl)-amide
1c  2-Cyclobutyl-3-methyl-1-oxo-1,2-dihydro-isoquinoline-4-carboxylic acid ((S)-1-phenyl-propyl)-amide
1d  2-Cyclohexyl-3-methyl-1-oxo-1,2-dihydro-isoquinoline-4-carboxylic acid ((S)-1-phenyl-propyl)-amide
1e  3-Methyl-1-oxo-2-(2,2,2-trifluoro-ethylamino)-1,2-dihydro-isoquinoline-4-carboxylic acid ((S)-1-phenyl-propyl)-amide
1f  3-Methyl-1-oxo-2-(2,2,2-trifluoro-ethyl)-1,2-dihydro-isoquinoline-4-carboxylic acid ((S)-1-phenyl-propyl)-amide
1g  3-Methyl-1-oxo-2-piperidin-1-yl-1,2-dihydro-isoquinoline-4-carboxylic acid ((S)-1-phenyl-propyl)-amide
1h  2-tert-Butylamino-3-methyl-1-oxo-1,2-dihydro-isoquinoline-4-carboxylic acid ((S)-1-phenyl-propyl)-amide
1i  2-Isopropylamino-3-methyl-1-oxo-1,2-dihydro-isoquinoline-4-carboxylic acid ((S)-1-phenyl-propyl)-amide 1j 3-Methyl-2-morpholin-4-yl-1-oxo-1,2-dihydro-isoquinoline-4-carboxylic acid ((S)-1-phenyl-propyl)-amide
1k 3-Methyl-1-oxo-2-propyl-1,2-dihydro-isoquinoline-4-carboxylic acid ((S)-1-phenyl-propyl)-amide
1l 2-Butyl-3-methyl-1-oxo-1,2-dihydro-isoquinoline-4-carboxylic acid ((S)-1-phenyl-propyl)-amide
1m 3-Methyl-2-(3-methyl-butyl)-1-oxo-1,2-dihydro-isoquinoline-4-carboxylic acid ((S)-1-phenyl-propyl)-amide
1n 2-(2-Methoxy-ethyl)-3-methyl-1-oxo-1,2-dihydro-isoquinoline-4-carboxylic acid ((S)-1-phenyl-propyl)-amide
1o 3-Methyl-1-oxo-2-(tetrahydro-furan-2-ylmethyl)-1,2-dihydro-isoquinoline-4-carboxylic acid ((S)-1-phenyl-propyl)-amide
1p 3-Methyl-1-oxo-2-pentyl-1,2-dihydro-isoquinoline-4-carboxylic acid ((S)-1-phenyl-propyl)-amide
1q 3-Methyl-2-(2-methylsulfanyl-ethyl)-1-oxo-1,2-dihydro-isoquinoline-4-carboxylic acid ((S)-1-phenyl-propyl)-amide
1r 2-Ethoxy-3-methyl-1-oxo-1,2-dihydro-isoquinoline-4-carboxylic acid ((S)-1-phenyl-propyl)-amide
1s 2-Cyclobutylamino-8-fluoro-3-methyl-1-oxo-1,2-dihydro-isoquinoline-4-carboxylic acid ((S)-cyclopropyl-phenyl-methyl)-amide
1t 2-Cyclopentylamino-8-fluoro-3-methyl-1-oxo-1,2-dihydro-isoquinoline-4-carboxylic acid ((S)-cyclopropyl-phenyl-methyl)-amide
1u 2-Ethoxy-8-fluoro-3-methyl-1-oxo-1,2-dihydro-isoquinoline-4-carboxylic acid ((S)-cyclopropyl-phenyl-methyl)-amide
1v 8-Chloro-2-ethoxy-3-methyl-1-oxo-1,2-dihydro-isoquinoline-4-carboxylic acid ((S)-1-phenyl-propyl)-amide
1w 8-Chloro-2-isobutoxy-3-methyl-1-oxo-1,2-dihydro-isoquinoline-4-carboxylic acid ((S)-1-phenyl-propyl)-amide
1x 8-Chloro-3-methyl-1-oxo-2-propoxy-1,2-dihydro-isoquinoline-4-carboxylic acid ((S)-1-phenyl-propyl)-amide
1y 2,3-Dimethyl-1-oxo-1,2-dihydro-isoquinoline-4-carboxylic acid ((S)-1-phenyl-propyl)-amide
1z 2-Isopropyl-3-methyl-1-oxo-1,2-dihydro-isoquinoline-4-carboxylic acid ((S)-1-phenyl-propyl)-amide
1aa 2-(2,2-Difluoro-propyl)-3-methyl-1-oxo-1,2-dihydro-isoquinoline-4-carboxylic acid ((S)-1-phenyl-propyl)-amide
2a 2-Ethylamino-3-methyl-1-oxo-1,2-dihydro-isoquinoline-4-carboxylic acid ((S)-1-phenyl-propyl)-amide
2b 3-Methyl-1-oxo-2-propylamino-1,2-dihydro-isoquinoline-4-carboxylic acid ((S)-1-phenyl-propyl)-amide
2c 2-Butylamino-3-methyl-1-oxo-1,2-dihydro-isoquinoline-4-carboxylic acid ((S)-1-phenyl-propyl)-amide
2d 2-Isobutylamino-3-methyl-1-oxo-1,2-dihydro-isoquinoline-4-carboxylic acid ((S)-1-phenyl-propyl)-amide
2e 2-(2,2-Dimethyl-propylamino)-3-methyl-1-oxo-1,2-dihydro-isoquinoline-4-carboxylic acid ((S)-1-phenyl-propyl)-amide
2f 2-(Cyclopropylmethyl-amino)-3-methyl-1-oxo-1,2-dihydro-isoquinoline-4-carboxylic acid ((S)-1-phenyl-propyl)-amide
2g 3-Methyl-2-(3-methyl-butylamino)-1-oxo-1,2-dihydro-isoquinoline-4-carboxylic acid ((S)-1-phenyl-propyl)-amide
2h 8-Chloro-2-ethylamino-3-methyl-1-oxo-1,2-dihydro-isoquinoline-4-carboxylic acid ((S)-1-phenyl-propyl)-amide
2i 2-Ethylamino-8-fluoro-3-methyl-1-oxo-1,2-dihydro-isoquinoline-4-carboxylic acid ((S)-cyclopropyl-phenyl-methyl)-amide
2j 8-Fluoro-2-isobutylamino-3-methyl-1-oxo-1,2-dihydro-isoquinoline-4-carboxylic acid ((S)-cyclopropyl-phenyl-methyl)-amide
2k 8-Fluoro-3-methyl-1-oxo-2-propylamino-1,2-dihydro-isoquinoline-4-carboxylic acid ((S)-cyclopropyl-phenyl-methyl)-amide
2l 8-Chloro-3-methyl-1-oxo-2-propylamino-1,2-dihydro-isoquinoline-4-carboxylic acid ((S)-1-phenyl-propyl)-amide
2m 8-Chloro-2-isobutylamino-3-methyl-1-oxo-1,2-dihydro-isoquinoline-4-carboxylic acid ((S)-1-phenyl-propyl)-amide
2n 2-Ethylamino-1-oxo-3-(2-oxo-pyrrolidin-1-ylmethyl)-1,2-dihydro-isoquinoline-4-carboxylic acid ((S)-1-phenyl-propyl)-amide
2o 1-Oxo-3-(2-oxo-pyrrolidin-1-ylmethyl)-2-propylamino-1,2-dihydro-isoquinoline-4-carboxylic acid ((S)-1-phenyl-propyl)-amide
2p 2-Ethylamino-8-fluoro-3-methyl-1-oxo-1,2-dihydro-isoquinoline-4-carboxylic acid [(S)-cyclopropyl-(3-fluoro-phenyl)-methyl]-amide
2q 8-Fluoro-3-methyl-1-oxo-2-propylamino-1,2-dihydro-isoquinoline-4-carboxylic acid [(S)-cyclopropyl-(3-fluoro-phenyl)-methyl]-amide
2r 2-Ethylamino-8-fluoro-1-oxo-3-(2-oxo-pyrrolidin-1-ylmethyl)-1,2-dihydro-isoquinoline-4-carboxylic acid [(S)-cyclopropyl-(3-fluoro-phenyl)-methyl]-amide
2s 2-Ethylamino-8-fluoro-3-methyl-1-oxo-1,2-dihydro-isoquinoline-4-carboxylic acid [(S)-cyclobutyl-(3-fluoro-phenyl)-methyl]-amide
2t 2-Ethylamino-8-fluoro-3-methyl-1-oxo-1,2-dihydro-isoquinoline-4-carboxylic acid ((S)-1-phenyl-propyl)-amide
2u 8-Fluoro-3-methyl-2-methylamino-1-oxo-1,2-dihydro-isoquinoline-4-carboxylic acid ((S)-cyclopropyl-phenyl-methyl)-amide
2v 8-Fluoro-3-methyl-2-methylamino-1-oxo-1,2-dihydro-isoquinoline-4-carboxylic acid [(S)-cyclopropyl-(4-fluoro-phenyl)-methyl]-amide
2w 2-Ethylamino-8-fluoro-3-methyl-1-oxo-1,2-dihydro-isoquinoline-4-carboxylic acid [(S)-cyclopropyl-(4-fluoro-phenyl)-methyl]-amide
2x 8-Fluoro-3-methyl-2-methylamino-1-oxo-1,2-dihydro-isoquinoline-4-carboxylic acid [(S)-cyclopropyl-(3,4-difluoro-phenyl)-methyl]-amide
2y 2-Ethylamino-8-fluoro-3-methyl-1-oxo-1,2-dihydro-isoquinoline-4-carboxylic acid [(S)-cyclopropyl-(3,4-difluoro-phenyl)-methyl]-amide
2z 8-Fluoro-3-methyl-2-methylamino-1-oxo-1,2-dihydro-isoquinoline-4-carboxylic acid [(S)-cyclobutyl-(3,4-difluoro-phenyl)-methyl]-amide
2aa 2-Ethylamino-8-fluoro-3-methyl-1-oxo-1,2-dihydro-isoquinoline-4-carboxylic acid [(S)-cyclobutyl-(3,4-difluoro-phenyl)-methyl]-amide
2ab 8-Iodo-3-methyl-1-oxo-2-propylamino-1,2-dihydro-isoquinoline-4-carboxylic acid [(S)-cyclobutyl-(3-fluoro-phenyl)-methyl]-amide
2ac 8-Fluoro-3-methyl-1-oxo-2-propylamino-1,2-dihydro-isoquinoline-4-carboxylic acid 3-iodo-benzylamide
3a 8-Fluoro-3-methyl-1-oxo-2-propyl-1,2-dihydro-isoquinoline-4-carboxylic acid [(S)-cyclopropyl-(3-fluoro-phenyl)-methyl]-amide
3b 8-Chloro-3-methyl-1-oxo-2-propyl-1,2-dihydro-isoquinoline-4-carboxylic acid [(S)-cyclopropyl-(3-fluoro-phenyl)-methyl]-amide
3c 8-Fluoro-3-methyl-1-oxo-2-propyl-1,2-dihydro-isoquinoline-4-carboxylic acid [(S)-cyclobutyl-(3-fluoro-phenyl)-methyl]-amide
3d 5,8-Difluoro-3-methyl-1-oxo-2-propyl-1,2-dihydro-isoquinoline-4-carboxylic acid [(S)-cyclopropyl-(3-fluoro-phenyl)-methyl]-amide 4a  8-Fluoro-2,3-dimethyl-1-oxo-1,2-dihydro-isoquinoline-4-carboxylic acid [(S)-cyclopropyl-(3-fluoro-phenyl)-methyl]-amide
4b  8-Fluoro-2-isopropyl-3-methyl-1-oxo-1,2-dihydro-isoquinoline-4-carboxylic acid [(S)-cyclopropyl-(3-fluoro-phenyl)-methyl]-amide
4c  2-Cyanomethyl-8-fluoro-3-methyl-1-oxo-1,2-dihydro-isoquinoline-4-carboxylic acid [(S)-cyclopropyl-(3-fluoro-phenyl)-methyl]-amide
4d  8-Fluoro-3-methyl-1-oxo-2-(3,3,3-trifluoro-propyl)-1,2-dihydro-isoquinoline-4-carboxylic acid [(S)-cyclopropyl-(3-fluoro-phenyl)-methyl]-amide
4e  2-(2,2-Difluoro-propyl)-8-fluoro-3-methyl-1-oxo-1,2-dihydro-isoquinoline-4-carboxylic acid [(S)-cyclopropyl-(3-fluoro-phenyl)-methyl]-amide
4f  8-Fluoro-2-(2-methoxy-ethyl)-3-methyl-1-oxo-1,2-dihydro-isoquinoline-4-carboxylic acid [(S)-cyclopropyl-(3-fluoro-phenyl)-methyl]-amide
4g  8-Fluoro-3-methyl-1-oxo-2-(2-pyrrolidin-1-yl-ethyl)-1,2-dihydro-isoquinoline-4-carboxylic acid [(S)-cyclopropyl-(3-fluoro-phenyl)-methyl]-amide
4h  8-Fluoro-3-methyl-2-(2-morpholin-4-yl-ethyl)-1-oxo-1,2-dihydro-isoquinoline-4-carboxylic acid [(S)-cyclopropyl-(3-fluoro-phenyl)-methyl]-amide
4h  2-Allyl-3-methyl-1-oxo-1,2-dihydro-isoquinoline-4-carboxylic acid ((S)-1-phenyl-propyl)-amide
4i  8-Fluoro-3-methyl-2-(3-morpholin-4-yl-propyl)-1-oxo-1,2-dihydro-isoquinoline-4-carboxylic acid [(S)-cyclopropyl-(3-fluoro-phenyl)-methyl]-amide
4i  2-(3-Methoxy-propyl)-3-methyl-1-oxo-1,2-dihydro-isoquinoline-4-carboxylic acid ((S)-1-phenyl-propyl)-amide
4j  6,8-Difluoro-3-methyl-1-oxo-2-(3,3,3-trifluoro-propyl)-1,2-dihydro-isoquinoline-4-carboxylic acid [(S)-cyclopropyl-(3-fluoro-phenyl)-methyl]-amide
4k  8-Fluoro-3-methyl-1-oxo-2-(2-oxo-oxazolidine-3-yl)-1,2-dihydro-isoquinoline-4-carboxylic acid [(S)-cyclopropyl-(3-fluoro-phenyl)-methyl]-amide
4k  3-Methyl-1-oxo-2-prop-2-ynyl-1,2-dihydro-isoquinoline-4-carboxylic acid ((S)-1-phenyl-propyl)-amide
4l  8-Fluoro-1-oxo-3-(2-oxo-pyrrolidin-1-ylmethyl)-2-(3,3,3-trifluoro-propyl)-1,2-dihydro-isoquinoline-4-carboxylic acid [(S)-cyclopropyl-(3-fluoro-phenyl)-methyl]-amide
4m  2-Cyclopropylmethyl-8-fluoro-3-methyl-1-oxo-1,2-dihydro-isoquinoline-4-carboxylic acid [(S)-cyclopropyl-(3-fluoro-phenyl)-methyl]-amide
4n  8-Fluoro-3-methyl-1-oxo-2-(5-oxo-pyrrolidin-2-ylmethyl)-1,2-dihydro-isoquinoline-4-carboxylic acid [(S)-cyclopropyl-(3-fluoro-phenyl)-methyl]-amide
4o  8-Fluoro-3-methyl-1-oxo-2-piperidin-3-ylmethyl-1,2-dihydro-isoquinoline-4-carboxylic acid [(S)-cyclopropyl-(3-fluoro-phenyl)-methyl]-amide
4p  8-Fluoro-2-(2-hydroxy-ethyl)-3-methyl-1-oxo-1,2-dihydro-isoquinoline-4-carboxylic acid [(S)-cyclobutyl-(3-fluoro-phenyl)-methyl]-amide
4q  8-Fluoro-3-methyl-1-oxo-2-(R)-tetrahydro-furan-3-yl-1,2-dihydro-isoquinoline-4-carboxylic acid [(S)-cyclobutyl-(3-fluoro-phenyl)-methyl]-amide
4r  8-Fluoro-3-methyl-1-oxo-2-(S)-tetrahydro-furan-3-yl-1,2-dihydro-isoquinoline-4-carboxylic acid [(S)-cyclobutyl-(3-fluoro-phenyl)-methyl]-amide
4s  8-Fluoro-3-methyl-1-oxo-2-(tetrahydro-pyran-4-yl)-1,2-dihydro-isoquinoline-4-carboxylic acid [(S)-cyclobutyl-(3-fluoro-phenyl)-methyl]-amide
4t  2-Ethoxy-8-fluoro-3-methyl-1-oxo-1,2-dihydro-isoquinoline-4-carboxylic acid [(S)-cyclobutyl-(3-fluoro-phenyl)-methyl]-amide
4u  8-Fluoro-3-methyl-1-oxo-2-propoxy-1,2-dihydro-isoquinoline-4-carboxylic acid [(S)-cyclobutyl-(3-fluoro-phenyl)-methyl]-amide
4v  2-Ethoxy-8-fluoro-3-methyl-1-oxo-1,2-dihydro-isoquinoline-4-carboxylic acid [(S)-cyclopropyl-(3-fluoro-phenyl)-methyl]-amide
4w  8-Fluoro-3-methyl-1-oxo-2-propoxy-1,2-dihydro-isoquinoline-4-carboxylic acid [(S)-cyclopropyl-(3-fluoro-phenyl)-methyl]-amide
4x  2-Allyl-8-fluoro-3-methyl-1-oxo-1,2-dihydro-isoquinoline-4-carboxylic acid [(S)-cyclobutyl-(3-fluoro-phenyl)-methyl]-amide
4y  2-Allyl-8-fluoro-3-methyl-1-oxo-1,2-dihydro-isoquinoline-4-carboxylic acid [(S)-cyclopropyl-(3-fluoro-phenyl)-methyl]-amide
4z  8-Fluoro-3-methyl-1-oxo-2-prop-2-ynyl-1,2-dihydro-isoquinoline-4-carboxylic acid [(S)-cyclobutyl-(3-fluoro-phenyl)-methyl]-amide
4aa  8-Fluoro-3-methyl-1-oxo-2-prop-2-ynyl-1,2-dihydro-isoquinoline-4-carboxylic acid [(S)-cyclopropyl-(3-fluoro-phenyl)-methyl]-amide
4ab  2-Cyclopropylmethyl-8-fluoro-3-methyl-1-oxo-1,2-dihydro-isoquinoline-4-carboxylic acid [(S)-cyclobutyl-(3-fluoro-phenyl)-methyl]-amide
5a  8-Fluoro-3-methyl-1-oxo-2-(S)-1-pyrrolidin-2-ylmethyl-1,2-dihydro-isoquinoline-4-carboxylic acid [(S)-cyclobutyl-(3-fluoro-phenyl)-methyl]-amide
5b  8-Fluoro-3-methyl-1-oxo-2-(R)-1-pyrrolidin-3-ylmethyl-1,2-dihydro-isoquinoline-4-carboxylic acid [(S)-cyclobutyl-(3-fluoro-phenyl)-methyl]-amide
5c  8-Fluoro-3-methyl-1-oxo-2-(S)-1-pyrrolidin-3-ylmethyl-1,2-dihydro-isoquinoline-4-carboxylic acid [(S)-cyclobutyl-(3-fluoro-phenyl)-methyl]-amide
5d  8-Fluoro-3-methyl-1-oxo-2-(R)-1-pyrrolidin-2-ylmethyl-1,2-dihydro-isoquinoline-4-carboxylic acid [(S)-cyclobutyl-(3-fluoro-phenyl)-methyl]-amide
5e  8-Fluoro-3-methyl-1-oxo-2-(S)-1-pyrrolidin-2-ylmethyl-1,2-dihydro-isoquinoline-4-carboxylic acid [(S)-cyclopropyl-(3-fluoro-phenyl)-methyl]-amide
5f  8-Fluoro-3-methyl-1-oxo-2-(R)-1-pyrrolidin-2-ylmethyl-1,2-dihydro-isoquinoline-4-carboxylic acid [(S)-cyclopropyl-(3-fluoro-phenyl)-methyl]-amide
5g  8-Fluoro-3-methyl-1-oxo-2-(R)-pyrrolidin-3-yl-1,2-dihydro-isoquinoline-4-carboxylic acid [(S)-cyclopropyl-(3-fluoro-phenyl)-methyl]-amide
5h  8-Fluoro-3-methyl-1-oxo-2-(S)-pyrrolidin-3-yl-1,2-dihydro-isoquinoline-4-carboxylic acid [(S)-cyclopropyl-(3-fluoro-phenyl)-methyl]-amide
6a  8-Fluoro-1-oxo-3-piperazin-1-ylmethyl-2-propyl-1,2-dihydro-isoquinoline-4-carboxylic acid [(S)-cyclopropyl-(3-fluoro-phenyl)-methyl]-amide
6b  8-Fluoro-1-oxo-3-piperazin-1-ylmethyl-2-propyl-1,2-dihydro-isoquinoline-4-carboxylic acid [(S)-cyclobutyl-(3-fluoro-phenyl)-methyl]-amide
6c  3-(4-tert-Butyl-piperazin-1-ylmethyl)-8-chloro-1-oxo-2-propyl-1,2-dihydro-isoquinoline-4-carboxylic acid [(S)-cyclopropyl-(3-fluoro-phenyl)-methyl]-amide
6d  8-Chloro-1-oxo-3-(2-oxo-pyrrolidin-1-ylmethyl)-2-propyl-1,2-dihydro-isoquinoline-4-carboxylic acid [(S)-cyclopropyl-(3-fluoro-phenyl)-methyl]-amide
6e  8-Fluoro-1-oxo-3-(2-oxo-pyrrolidin-1-ylmethyl)-2-propyl-1,2-dihydro-isoquinoline-4-carboxylic acid [(S)-cyclopropyl-(3-fluoro-phenyl)-methyl]-amide
6f  3-(4-tert-Butyl-piperazin-1-ylmethyl)-8-fluoro-1-oxo-2-propyl-1,2-dihydro-isoquinoline-4-carboxylic acid [(S)-cyclopropyl-(3-fluoro-phenyl)-methyl]-amide 6g 3-((2R,5S)-2,5-Dimethyl-piperazin-1-ylmethyl)-8-fluoro-1-oxo-2-(3,3,3-trifluoro-propyl)-1,2-dihydro-isoquinoline-4-carboxylic acid [(S)-cyclopropyl-(3-fluorophenyl)-methyl]-amide 7a 8-Fluoro-3-methyl-2-((S)-1-methyl-pyrrolidin-2-ylmethyl)-1-oxo-1,2-dihydro-isoquinoline-4-carboxylic acid [(S)-cyclopropyl-(3-fluoro-phenyl)-methyl]-amide 7b 2-((S)-1-Ethyl-pyrrolidin-2-ylmethyl)-8-fluoro-3-methyl-1-oxo-1,2-dihydro-isoquinoline-4-carboxylic acid [(S)-cyclopropyl-(3-fluoro-phenyl)-methyl]-amide 7c 8-Fluoro-3-methyl-1-oxo-2-((S)-1-propyl-pyrrolidin-2-ylmethyl)-1,2-dihydro-isoquinoline-4-carboxylic acid [(S)-cyclopropyl-(3-fluoro-phenyl)-methyl]-amide 7d 2-((S)-1-Acetyl-pyrrolidin-2-ylmethyl)-8-fluoro-3-methyl-1-oxo-1,2-dihydro-isoquinoline-4-carboxylic acid [(S)-cyclopropyl-(3-fluoro-phenyl)-methyl]-amide 7e 8-Fluoro-3-methyl-2-((R)-1-methyl-pyrrolidin-2-ylmethyl)-1-oxo-1,2-dihydro-isoquinoline-4-carboxylic acid [(S)-cyclopropyl-(3-fluoro-phenyl)-methyl]-amide 7f 2-((R)-1-Ethyl-pyrrolidin-2-ylmethyl)-8-fluoro-3-methyl-1-oxo-1,2-dihydro-isoquinoline-4-carboxylic acid [(S)-cyclopropyl-(3-fluoro-phenyl)-methyl]-amide 7g 8-Fluoro-3-methyl-1-oxo-2-((R)-1-propyl-pyrrolidin-2-ylmethyl)-1,2-dihydro-isoquinoline-4-carboxylic acid [(S)-cyclopropyl-(3-fluoro-phenyl)-methyl]-amide 7h 2-((R)-1-Acetyl-pyrrolidin-2-ylmethyl)-8-fluoro-3-methyl-1-oxo-1,2-dihydro-isoquinoline-4-carboxylic acid [(S)-cyclopropyl-(3-fluoro-phenyl)-methyl]-amide 7i 8-Fluoro-3-methyl-2-((R)-1-methyl-pyrrolidin-3-yl)-1-oxo-1,2-dihydro-isoquinoline-4-carboxylic acid [(S)-cyclopropyl-(3-fluoro-phenyl)-methyl]-amide 7j 8-Fluoro-3-methyl-2-((S)-1-methyl-pyrrolidin-2-ylmethyl)-1-oxo-1,2-dihydro-isoquinoline-4-carboxylic acid [(S)-cyclobutyl-(3-fluoro-phenyl)-methyl]-amide 7k 2-((S)-1-Ethyl-pyrrolidin-2-ylmethyl)-8-fluoro-3-methyl-1-oxo-1,2-dihydro-isoquinoline-4-carboxylic acid [(S)-cyclobutyl-(3-fluoro-phenyl)-methyl]-amide 7l 8-Fluoro-3-methyl-2-((R)-1-methyl-pyrrolidin-2-ylmethyl)-1-oxo-1,2-dihydro-isoquinoline-4-carboxylic acid [(S)-cyclobutyl-(3-fluoro-phenyl)-methyl]-amide 8a 2-Ethylamino-8-fluoro-3-methyl-1-oxo-1,2-dihydro-isoquinoline-4-carboxylic acid [(S)-1-(4-fluoro-phenyl)-propyl]-amide 8b 2-Ethylamino-8-fluoro-3-methyl-1-oxo-1,2-dihydro-isoquinoline-4-carboxylic acid [(S)-cyclobutyl-(4-fluoro-phenyl)-methyl]-amide 8c 8-Fluoro-3-methyl-1-oxo-2-propylamino-1,2-dihydro-isoquinoline-4-carboxylic acid [(S)-cyclobutyl-(3-fluoro-phenyl)-methyl]-amide 9a 8-Fluoro-3-fluoromethyl-1-oxo-2-propylamino-1,2-dihydro-isoquinoline-4-carboxylic acid [(S)-cyclobutyl-(3-fluoro-phenyl)-methyl]-amide 10a 8-Fluoro-2-(3-fluoro-propylamino)-3-methyl-1-oxo-1,2-dihydro-isoquinoline-4-carboxylic acid [(S)-cyclobutyl-(3-fluoro-phenyl)-methyl]-amide 10b 8-Fluoro-2-(2-fluoro-ethylamino)-3-methyl-1-oxo-1,2-dihydro-isoquinoline-4-carboxylic acid [(S)-cyclobutyl-(3-fluoro-phenyl)-methyl]-amide 10c 2-(2,2-Difluoro-ethylamino)-8-fluoro-3-methyl-1-oxo-1,2-dihydro-isoquinoline-4-carboxylic acid [(S)-cyclobutyl-(3-fluoro-phenyl)-methyl]-amide 10d 8-Fluoro-3-methyl-1-oxo-2-prop-2-ynylamino-1,2-dihydro-isoquinoline-4-carboxylic acid [(S)-cyclobutyl-(3-fluoro-phenyl)-methyl]-amide 11a 2-Ethylamino-8-hydroxy-3-methyl-1-oxo-1,2-dihydro-isoquinoline-4-carboxylic acid ((S)-cyclopropyl-phenyl-methyl)-amide Further, the compounds of the invention may exist in unsolvated as well as in solvated forms in which the solvent molecules are selected from pharmaceutically acceptable solvents such as water, ethanol and the like. In general, such solvated forms are considered equivalent to the unsolvated forms for the purposes of this invention.

The compounds of the present invention may have one or more asymmetric centres and it is intended that any optical isomers (i.e. enantiomers or diastereomers), in the form of separated, pure or partially purified optical isomers and any mixtures thereof including racemic mixtures, i.e. a mixture of stereoisomers, are included within the scope of the invention. In particular, when A represents CH or $CR^1$, A may be an asymmetrical centre giving rise to two optical isomers, an R form and an S form. In one embodiment, the compounds of the present invention have the S form.

In a particular embodiment, the compounds of the present invention have the following absolute configuration at A, A being CH

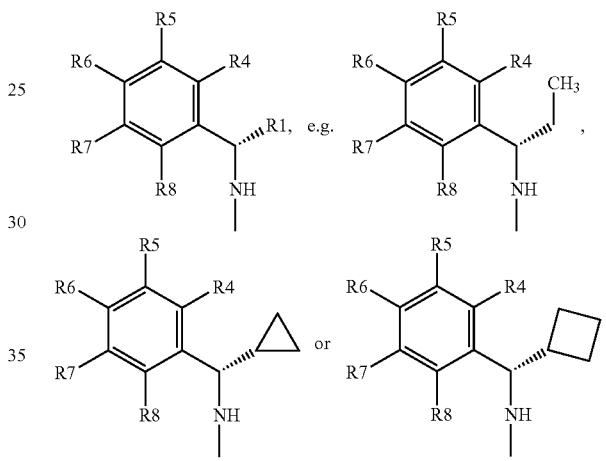

In this context is understood that when specifying the enantiomeric form, then the compound is in enantiomeric excess, e.g. essentially in a pure, mono-enantiomeric form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography of an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

NK3 receptor antagonists have been implicated in various diseases in addition to psychosis and schizophrenia discussed above. Langlois et al in *J. Pharm. Exp. Ther.*, 299, 712-717, 2001, concludes that NK3 antagonists may be applicable in CNS diseases in general, and in anxiety and depression in particular. Yip et al in *Br. J. Phar.*, 122, 715-722, 1997 further implicates NK3 antagonists in diverse brain functions, such as cortical processing, learning and memory, neuroendocrine and behavioral regulation. Additional studies have shown that NKB and NK3 receptors are involved in pain, and that NK3 antagonists have an antinociceptive and analgesic effect [Fioramonti, *Neurogastroenterol. Motil.*, 15, 363-369, 2003]. Mazelin et al in *Life Sci.*, 63, 293-304, 1998 show that NK3 antagonists have an effect in gut inflammation and concludes that such antagonists may be used in the treatment of irritable bowel syndrome (IBS). In addition, NK3 antagonists have in in vivo models been demonstrated to be useful in the treatment of airway related diseases, such as asthma, airway hyperresponsiveness, cough, and bronchorestriction [Daoui, *Am. J. Respir. Crit. Care Med.*, 158, 42-48, 1998]. Maubach et al in *Neurosci.*, 83, 1047-1062, 1998 show that NKB and the NK3 agonist senktide increase the frequency and duration of epileptiform discharges, and thus by inference that NK3 antagonists have a anticonvulsive potential. Finally, Kernel et al in *J. Neurosci.*, 22, 1929-1936, 2002, suggests the use of NK3 antagonists in the treatment of Parkinson's Disease.

Accordingly, clinical, pre-clinical, in vivo and in vitro studies support that NK3 receptor antagonists are of relevance for the treatment or prevention of various disorders including psychosis, schizophrenia, depression, anxiety, cognitive impairment, obesity, Alzheimer's disease, Parkinson's disease, pain, convulsions, cough, asthma, airway hyperresponsiveness, microvascular hypersensitivity, bronchoconstriction, gut inflammation, inflammatory bowel syndrome, PTSD, dementia and agitation and delirium in the elderly.

Schizophrenia is classified into subgroups. The paranoid type is characterised by delusions and hallucinations and absence of thought disorder, disorganized behavior and affective flattening. The disorganized type, which is also named 'hebephrenic schizophrenia' in the ICD, in which thought disorder and flat affect are present together. The catatonic type, in which prominent psychomotor disturbances are evident, and symptoms may include catatonic stupor and waxy flexibility. The undifferentiated type in which psychotic symptoms are present but the criteria for paranoid, disorganized, or catatonic types have not been met. The symptoms of schizophrenia normally manifest themselves in three broad categories, i.e. positive, negative and cognitive symptoms. Positive symptoms are those, which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making. The current antipsychotics are fairly successful in treating the positive symptoms but fare less well for the negative and cognitive symptoms. Contrary to that, NK3 antagonists have been shown clinically to improve on both positive and negative symptoms in schizophrenics [*Am. J. Psychiatry*, 161, 975-984, 204], and according to the above discussion they are also expected to deliver an effect on the cognitive symptoms.

Cognitive impairment include a decline in cognitive functions or cognitive domains, e.g. working memory, attention and vigilance, verbal learning and memory, visual learning and memory, reasoning and problem solving e.g. executive function, speed of processing and/or social cognition. In particular, cognitive impairment may indicate deficits in attention, disorganized thinking, slow thinking, difficulty in understanding, poor concentration, impairment of problem solving, poor memory, difficulties in expressing thoughts and/or difficulties in integrating thoughts, feelings and behaviour, or difficulties in extinction of irrelevant thoughts.

Imaging methods such as positron emission tomography (PET) have become important techniques in the clinical development of drugs. Compounds, with high affinity for the relevant target labeled with short-lived radionuclides are administrated e.g. intravenously to animals such as humans for PET measurements. The conventional strategy is to examine the inhibition of the signal of the labeled compound (PET ligand) by an unlabeled test compound. This will enable the determination of the correlation between the concentration of the test compound in plasma and the occupancy at the target in question. Such information is of critical importance for the dose finding in clinical development of drugs. The "effective amount" of a PET ligand is an amount adequate for obtaining a specific signal for the target in question. A specific signal is the difference between the signal obtained by the receptor bound PET ligand alone and the signal obtained by the receptor bound PET ligand in presence of a test compound binding to the target in question.

Preferably, a compound to be used in the treatment of a CNS disease is able to enter the brain in an adequate amount at an adequate rate i.e. the compound must possess properties allowing it to pass the blood brain barrier.

The ability of a compound to permeate the blood-brain barrier relies partly on the physico-chemical properties that influence the passive transport across the cell layer. Another factor influencing permeability across the BBB is efflux transport, e.g. mediated by the P-gp transporter located in the cell layer, which prevents certain compounds from entering the brain.

Furthermore, in order to minimize peripheral side effects, a high ratio between the steady-state brain and plasma concentration is desired to achieve a high CNS activity while maintaining minor amounts of compound in the plasma. To achieve that, it is mandatory that a certain fraction of the compound is free of binding to plasma proteins, i.e. a high plasma free fraction is beneficial.

Compounds of the present invention, in particular 2-alkyl-amino-isoquinolines (i.e. compounds of the present invention wherein Q is NH, such as wherein Q is NH; Y is optionally substituted $C_{1-6}$alkyl; X is $C_{1-6}$alkyl; $R^4$-$R^{12}$ is H or halogen; and A is CH) have been shown to possess excellent BBB permeability. This may be explained by the fact that in general, these compounds benefit from a high passive permeability as well as no or low affinity for the P-gp transporter. In addition to that, a high plasma free fraction is a common feature for these compounds, as shown in the examples.

In one embodiment, the invention provides compounds useful as PET ligands, i.e. defined by formula I' wherein each C can be the $^{11}C$ isotope and each F can be the $^{18}F$ isotope, wherein said compound comprises at least one of said isotopes; and pharmaceutically acceptable salts thereof.

In one embodiment the present invention provides radiolabeled compounds of formula I', in particular selected from the undermentioned list

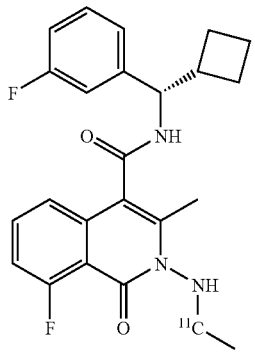

2-((1-$^{11}$C)-Ethylamino)-8-fluoro-3-methyl-1-oxo-1,2-dihydro-isoquinoline-4-carboxylic acid [(S)-cyclobutyl-(3-fluoro-phenyl)-methyl]-amide

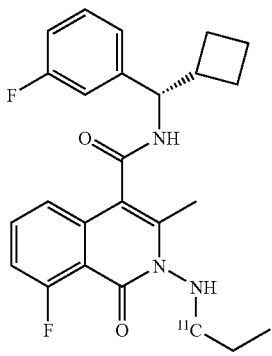

8-Fluoro-3-methyl-1-oxo-2-((1-$^{11}$C)-propylamino)-1,2-dihydro-isoquinoline-4-carboxylic acid [(S)-cyclobutyl-(3-fluoro-phenyl)-methyl]-amide

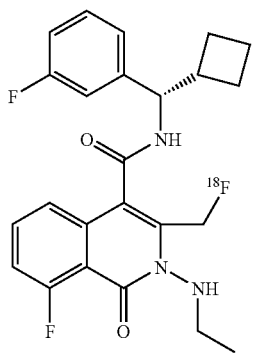

2-Ethylamino-8-fluoro-3-($^{18}$F)-fluoromethyl-1-oxo-1,2-dihydro-isoquinoline-4-carboxylic acid [(S)-cyclobutyl-(3-fluoro-phenyl)-methyl]-amide

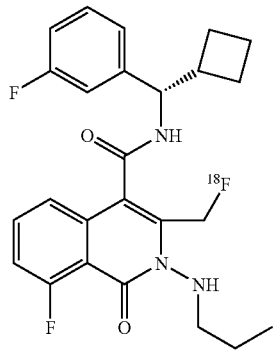

8-Fluoro-3-($^{18}$F)-fluoromethyl-1-oxo-2-propylamino-1,2-dihydro-isoquinoline-4-carboxylic acid [(S)-cyclobutyl-(3-fluoro-phenyl)-methyl]-amide

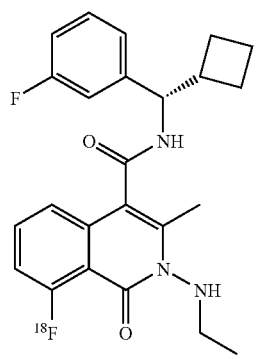

2-Ethylamino-8-($^{18}$F)-fluoro-3-methyl-1-oxo-1,2-dihydro-isoquinoline-4-carboxylic acid [(S)-cyclobutyl-(3-fluoro-phenyl)-methyl]-amide

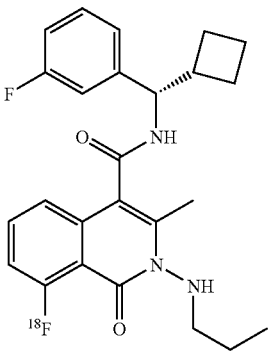

21

8-($^{18}$F)-Fluoro-3-methyl-1-oxo-2-propylamino-1,2-dihydro-isoquinoline-4-carboxylic acid [(S)-cyclobutyl-(3-fluoro-phenyl)-methyl]-amide

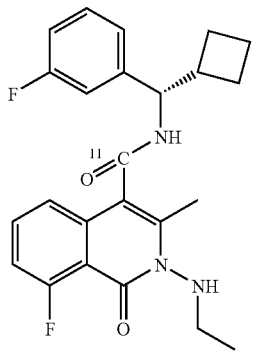

2-Ethylamino-8-fluoro-3-methyl-1-oxo-1,2-dihydro-isoquinoline-4-($^{11}$C)-carboxylic acid [(S)-cyclobutyl-(3-fluoro-phenyl)-methyl]-amide

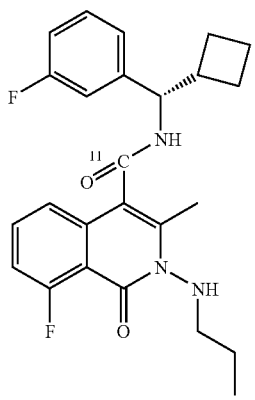

8-Fluoro-3-methyl-1-oxo-2-propylamino-1,2-dihydro-isoquinoline-4-($^{11}$C)-carboxylic acid [(S)-cyclobutyl-(3-fluoro-phenyl)-methyl]-amide

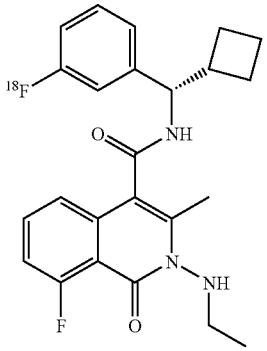

22

2-Ethylamino-8-fluoro-3-methyl-1-oxo-1,2-dihydro-isoquinoline-4-carboxylic acid [(S)-cyclobutyl-(3-($^{18}$F)-fluoro-phenyl)-methyl]-amide

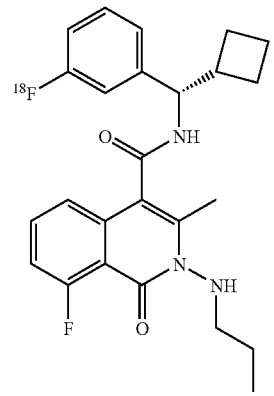

8-Fluoro-3-methyl-1-oxo-2-propylamino-1,2-dihydro-isoquinoline-4-carboxylic acid [(S)-cyclobutyl-(3-($^{18}$F)-fluoro-phenyl)-methyl]-amide

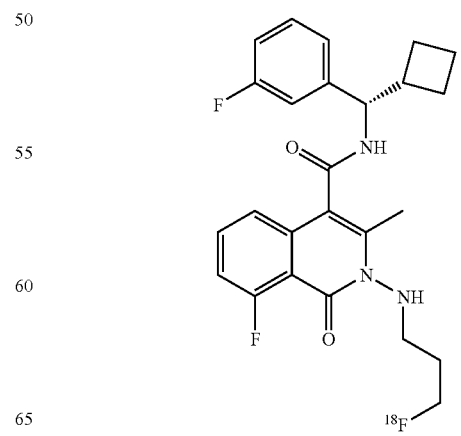

8-Fluoro-2-(3-($^{18}$F)-fluoro-propylamino)-3-methyl-1-oxo-1,2-dihydro-isoquinoline-4-carboxylic acid [(S)-cyclobutyl-(3-fluoro-phenyl)-methyl]-amide

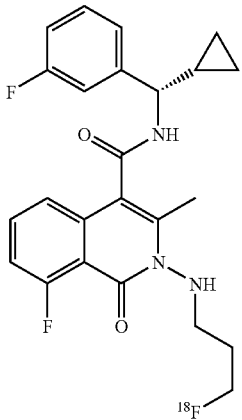

8-Fluoro-2-(3-($^{18}$F)-fluoro-propylamino)-3-methyl-1-oxo-1,2-dihydro-isoquinoline-4-carboxylic acid [(S)-cyclopropyl-(3-fluoro-phenyl)-methyl]-amide

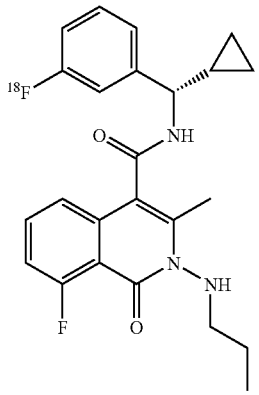

8-Fluoro-3-methyl-1-oxo-2-propylamino-1,2-dihydro-isoquinoline-4-carboxylic acid [(S)-cyclopropyl-(3-($^{18}$F)-fluoro-phenyl)-methyl]-amide In one embodiment, the present invention relates to the use of a PET ligand of the present invention for determination of the binding occupancy of an NK3 ligand at the NK3 receptor.

In one embodiment, the present invention relates to a method for determining binding occupancy at the NK3 receptor of an NK3 ligand by use of a PET ligand of the present invention.

In one embodiment, the present invention relates to the compounds of the present invention for use in therapy.

In one embodiment, the present invention relates to a method of treating a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizotypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; inflammatory bowel syndrome; PTDS; dementia and agitation and delerium in the elderly the method comprising the administration of a therapeutically effective amount of a compound of the present invention to a patient in need thereof.

In one embodiment, the present invention relates to a method for the treatment of schizophrenia, the method comprising the administration of a therapeutically effective amount of a compound of the present invention to a patient in need thereof. In particular, said treatment includes the treatment of the positive, negative and/or cognitive symptoms of schizophrenia.

In one embodiment, the present invention relates to a method of treating cognitive impairment, the method comprising the administration of a therapeutically effective amount of a compound of the present invention to a patient in need thereof. In particular, said cognitive impairment is manifested as a decline in working memory, attention and vigilance, verbal learning and memory, visual learning and memory, reasoning and problem solving e.g. executive function, speed of processing and/or social cognition.

The antipsychotic effect of typical and atypical anti-psychotics, in particular D2 antagonists is exerted via an inhibition of the post-synaptic D2 receptors. Pre-synaptic D2 autoreceptors, however, are also affected by the administration of these compounds giving rise to an increase in the dopamine neuron firing rate, which, in fact, counteracts the antipsychotic effects. The increased firing rate continues until the effect of the pre-synaptic auto-receptors is blocked (the depolarization block), typically after approximately 3 weeks of chronic treatment with typical or atypical anti-psychotics. This model explains the up to 3 weeks delay of clinical effect normally seen when D2 antagonist treatment is initiated. NK3 antagonists seem to inhibit the increase in the dopamine neuron firing mediated by the pre-synaptic D2 auto-receptors brought about by D2 antagonists, wherefore the combined administration of NK3 antagonists (e.g. compounds of the present invention) and D2 antagonists is expected to give rise to a faster onset of the clinical effect. Moreover, D2 antagonists are known to increase prolactin levels, which may give rise to serious side effects, such as osteoporosis. It is known that NK3 agonists give rise to an increase in prolactin from which it may be deduced that a NK3 antagonist will lower an increased prolactin level, i.e. bring about a normalisation of the prolactin level. A combined use of NK3 antagonists (e.g. compounds of the present invention) and D2 antagonists may thus address some of the safety issues associated with D2 antagonists administration. Similarly, NK3 antagonists (e.g. compounds of the present invention) may be administered together with antagonists/inverse agonists/negative modulators/partial agonists of one or more of the targets dopamine D2 receptor, dopamine D3 receptor, dopamine D4 receptor, phosphodiesterase PDE10, serotonin 5-HT$_{1A}$ receptor, serotonin 5-HT$_{2A}$ receptor, serotonin 5-HT$_6$ receptor, adrenergic alpha 2 receptor, cannabinoid type 1 receptor, histamine H3 receptor, cyclooxygenases, sodium channels or glycine transporter GlyT1; or with agonists/positive modulators/partial agonists of one or more of the targets serotonin 5-HT$_{2c}$ receptor, KCNQ channels, NMDA receptor, AMPA receptor, nicotinic alpha-7 receptor, muscarinic M1 receptor, muscarinic M4 receptor, metabotropic glutamate receptor mGluR2, metabotropic glutamate receptor mGluR5, dopamine D1 receptor or dopamine D5 receptor.

Such combined administration of compounds of the present invention and other anti-psychotic compounds may be sequential or concomitant. Examples of D2 antagonists or partial agonists include haloperidol, chlorpromazine, sulpirid, risperidone, ziprasidon, olanzapine, quetiapin, clozapine and aripiprazole.

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 1-1000 mg/day of a compound of the present invention, such as 1-500 mg/day, such as 1-100 mg/day or 1-50 mg/day.

In one embodiment, the present invention relates to the use of the compounds of the present invention in the manufacture of a medicament for the treatment of a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizotypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; inflammatory bowel syndrome, PTSD; dementia and agitation and delirium in the elderly.

In one embodiment, the present invention relates to the use of a compound of the present invention in the manufacture of a medicament for the treatment of schizophrenia. In particular, said treatment includes the treatment of the positive, negative and/or cognitive symptoms of schizophrenia.

In one embodiment, the present invention relates to the use of a compound of the present invention in the manufacture of a medicament for the treatment of cognitive impairment. In particular, said cognitive impairment is manifested as a decline in working memory, attention and vigilance, verbal learning and memory, visual learning and memory, reasoning and problem solving e.g. executive function, speed of processing and/or social cognition.

In one embodiment, the present invention relates to a compound of the present invention for use in the treatment of a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizotypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; inflammatory bowel syndrome; PTSD; dementia and agitation and delirium in the elderly.

In one embodiment, the present invention relates to a compound of the present invention for use in the treatment of schizophrenia. In particular, said treatment includes the treatment of the positive, negative and/or cognitive symptoms of schizophrenia.

In one embodiment, the present invention relates to a compound of the present invention for use in the treatment of cognitive impairment. In particular, said cognitive impairment is manifested as a decline in working memory, attention and vigilance, verbal learning and memory, visual learning and memory, reasoning and problem solving e.g. executive function, speed of processing and/or social cognition.

The compounds of the present invention may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, cremes, gels, inhalants, dermal patches, implants, etc.

Conveniently, the compounds of the invention are administered in a unit dosage form containing said compounds in an amount of about 0.1 to 500 mg, such as 1 mg, 5 mg, 10 mg, 50 mg, 100 mg, 150 mg, 200 mg or 250 mg of a compound of the present invention.

For parenteral routes such as intravenous, intrathecal, intramuscular and similar administration, typically doses are in the order of about half the dose employed for oral administration.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. The pharmaceutical compositions formed by combining the compound of the invention and the pharmaceutical acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by the compression of the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

In one embodiment, the invention relates to a pharmaceutical composition comprising a compound of the present invention together with a second anti-psychotic agent. In one embodiment, said second anti-psychotic agent is selected from antagonists/inverse agonists/negative modulators/partial agonists of the targets dopamine D2 receptor, dopamine D3 receptor, dopamine D4 receptor, phosphodiesterase PDE10, serotonin $5\text{-}HT_{1A}$ receptor, serotonin $5\text{-}HT_{2A}$ receptor, serotonin $5\text{-}HT_6$ receptor, adrenergic alpha 2 receptor, cannabinoid type 1 receptor, histamine H3 receptor, cyclooxygenases, sodium channels or glycine transporter GlyT1; or from agonists/positive modulators/partial agonists of the targets serotonin $5\text{-}HT_{2C}$ receptor, KCNQ channels, NMDA receptor, AMPA receptor, nicotinic alpha-7 receptor, muscarinic M1 receptor, muscarinic M4 receptor, metabotropic glutamate receptor mGluR2, metabotropic glutamate receptor mGluR5, dopamine D1 receptor or dopamine D5 receptor. Particular examples of such anti-psychotics include haloperidol, chlorpromazine, sulpirid, risperidone, ziprasidon, olanzapine, quetiapine, clozapine and aripoprazole.

In one embodiment, the invention relates to a pharmaceutical kit comprising a container containing a compound of the present invention and a separate container containing an anti-psychotic drug, such as typical anti-psychotics, atypical anti-psychotics, antagonists/inverse agonists/negative modulators/partial agonists of one or more of the targets dopamine D2 receptor, dopamine D3 receptor, dopamine D4 receptor, phosphodiesterase PDE10, serotonin $5\text{-}HT_{1A}$ receptor, serotonin $5\text{-}HT_{2A}$ receptor, serotonin $5\text{-}HT_6$ receptor, adrenergic alpha 2 receptor, cannabinoid type 1 receptor, histamine H3 receptor, cyclooxygenases, sodium channels or glycine transporter GlyT1; or with agonists/positive modulators/partial agonists of one or more of the targets serotonin $5\text{-}HT_{2C}$ receptor, KCNQ channels, NMDA receptor AMPA receptor, nicotinic alpha-7 receptor, muscarinic M1 receptor, muscarinic M4 receptor, metabotropic glutamate receptor mGluR2, metabotropic glutamate receptor mGluR5, dopamine D1 receptor or dopamine D5 receptor.

Particular examples of such anti-psychotics include haloperidol, chlorpromazine, sulpirid, risperidone, ziprasidon, olanzapine, quetiapine, clozapine and aripiprazole.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or a particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Synthetic Routes

The compounds of the present invention of the general formula I, wherein $R^1\text{-}R^{12}$, A, X, Q, and Y are as defined above can be prepared by the methods outlined in the following reaction schemes and examples. In the described methods it is possible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples.

In the intermediate compounds of the general formulae II-XXXI, $R^1$-$R^{12}$, A, X, Q, and Y are as defined under formula I.

For compounds, which can exist as a mixture or equilibrium between two or more tautomers, only one tautomer is represented in the schemes, although it may not be the most stable tautomer. For compounds, which can exist in enantiomeric, stereoisomeric or geometric isomeric forms their geometric configuration is specified; otherwise the structure represents a mixture of stereoisomers. Such compounds include, but not limited to 1,3-ketoesters or enamines of the general formula IV and VII, which can exist in equilibrium between keto or enol forms and the latter may also exist in isomeric Z- and E-forms as well-known to chemists skilled in the art. Such compounds also include compounds of the present invention of the general formula I, which may exist as a mixture of atropisomers due to restricted rotation around carbon-carbon single bonds similar to atropisomerism in ortho, ortho-disubstituted biaryl compounds also well-known to the person skilled in the art.

Starting materials of the general formulae II, III, VI, XI, XX, and XXI are either obtained from commercial sources as summarized in the Table 2 or they can be readily prepared by standard methods or their modifications described in the literature.

2-Bromobenzoic acids of the general formula II are coupled with keto-esters of the general formula III in the presence of a strong base such as sodium hydride and copper or copper salts such as copper (I) bromide in a suitable solvent such as 1,4-dioxane, acetonitrile or an excess of the above keto-esters at suitable temperature such as reflux or at 70° C. with the formation of compounds of the general formula IV (Scheme 1). Such arylation reaction is well known in general as copper-catalyzed Ullmann-type coupling reaction (review: S. V. Ley, A. W. Thomas *Angew. Chem. Int. Ed.* 2003, 42, 5400). Also, in this particular case when the coupling reaction involves activated methylene compounds such as compounds of the general formula IV in the presence of copper or copper salts the reaction is known as the Hurtley reaction (W. R. H. Hurtley *J. Chem. Soc.* 1929, 1870).

The obtained compounds of the general formula IV are then condensed with amino compounds of the general formula VI with or without appropriate solvent under the heating conditions with the formation of isoquinolinones of the general formula VIII via intermediate formation of enamines of the general formula VII which are usually not separated from the reaction mixture. Alternatively, the enamines of the general formula VII can be obtained from amino compounds of the general formula VI in the presence of the appropriate dehydrating agent such as tetraethoxysilane under heating conditions or at ambient temperature in the presence of a catalytic amount of acid such as acetic acid. Then, the cyclisation reaction with the formation of isoquinolinones of the general formula VIII can be carried out under the heating conditions as mentioned above or at ambient temperature in the presence of an appropriate coupling reagent such as EDC/HOBT (Scheme 1).

Furthermore, isoquinolinones of the general formula VIII can be obtained directly from the starting 2-bromobenzoic acids of the general formula II and deprotonated enamines of the general formula V in a modified one-pot procedure involving Hurtley reaction performed at 70° C. with the formation of the compounds of the general formula VII and subsequent cyclisation performed at higher temperature. Enamines of the general formula V are readily available from ketoesters III and amino compounds VI under conditions described above for preparation of enamines of the general formula VII (Scheme 1).

Compounds of the general formula VIII are readily hydrolyzed to acids of the general formula IX under conditions for ester hydrolysis well known to chemists skilled in the art. Finally, the subsequent coupling with amines (A=C) or hydrazines (A=N) of the general formula XI leads to the formation of the compounds of the invention of the general formula I (Scheme 1). Such coupling reactions usually performed via activation of the acid with an appropriate coupling or activation reagent such as but not limited to thionyl chloride with the formation of corresponding acid chloride or in the presence EDC/HOBT. Hydrazides of the general formula I (A=N) where R1=H can be converted to disubstituted hydrazides of the same general formula where R1 is not hydrogen by acylation, alkylation or arylation reactions with appropriate acylation or alkylation reagents such as but not limited to acid chlorides, carbamoyl chlorides, chloroformates or alkylhalogenides.

Compounds of the general formula I where X is methyl can be converted to the compounds of the general formula XII by regioselective bromination reaction in the presence of bromination reagent such as bromine. Then the bromine atom can be substituted by various nucleophiles of the general formula X'—H or X'⁻ with the formation of the compounds of the invention of the general formula I as shown in Scheme 2. Those skilled in the art will readily appreciate that many nitrogen, carbon and sulphur nucleophiles such as but not limited to amines, aromatic amines, amides, heterocycles, alcohols, phenols, cyanides or thiols are commercially or readily available in the neutral or in the deprotonated anionic form required for such transformation.

If necessary, further derivatisation or transformation can be performed in the substituents $R^4$-$R^{12}$ and X using standard methods of organic synthesis known to the person of ordinary skill in the art.

Scheme 1

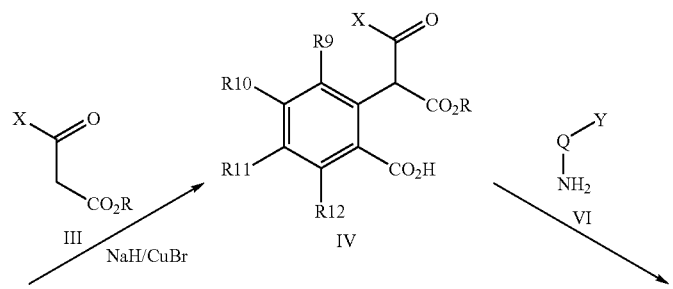

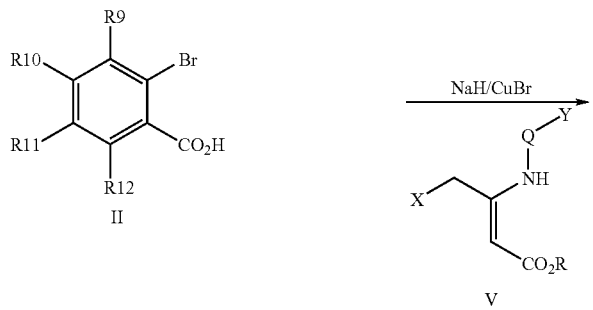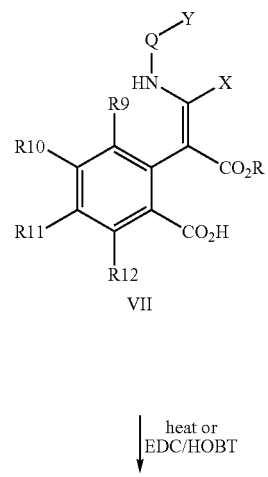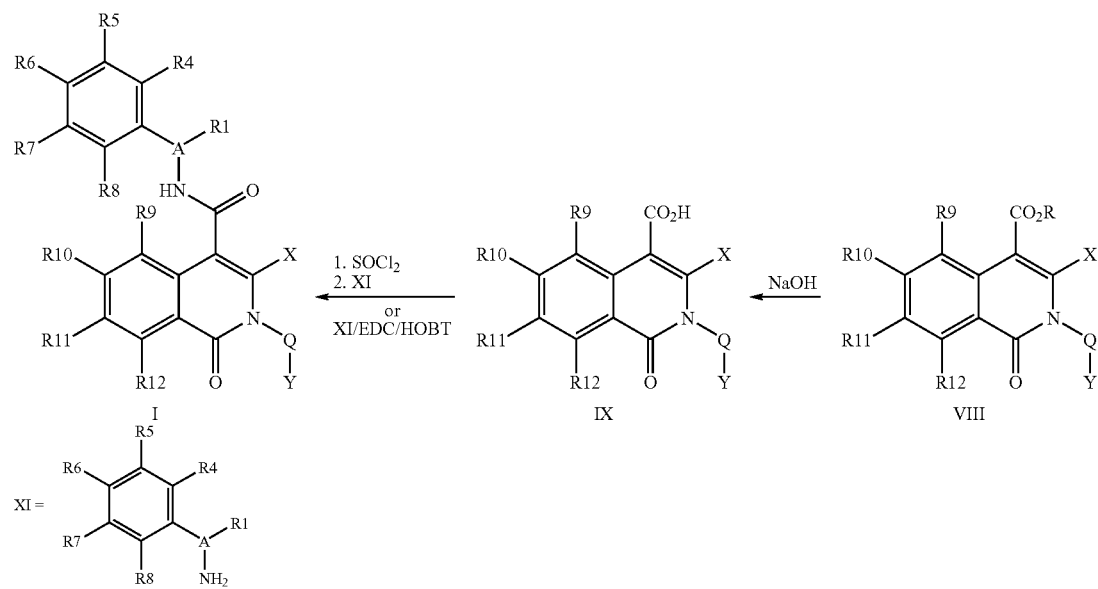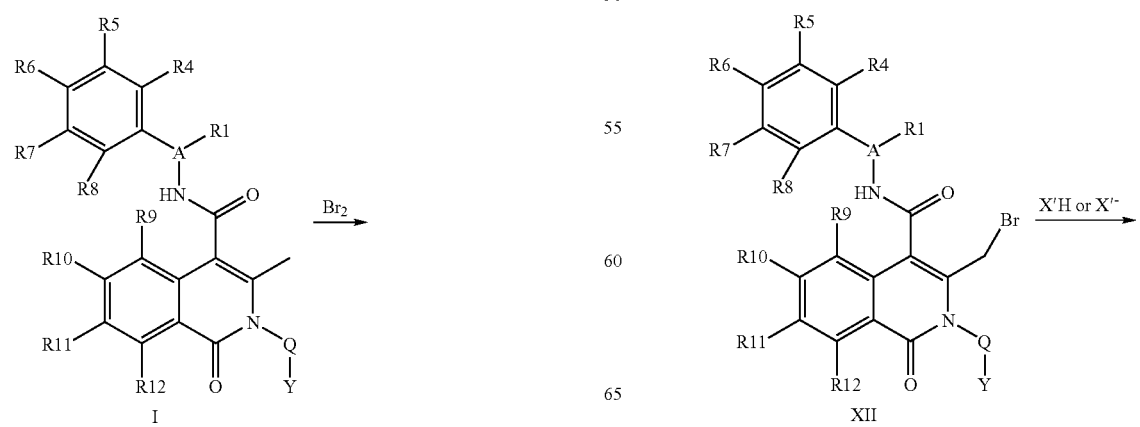
Scheme 2

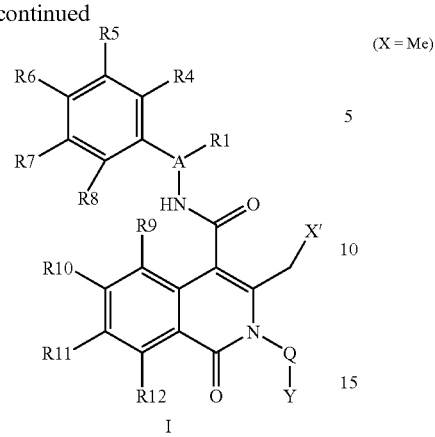
(X = Me)
I
Scheme 3. Synthesis of homophthalic anhydrides
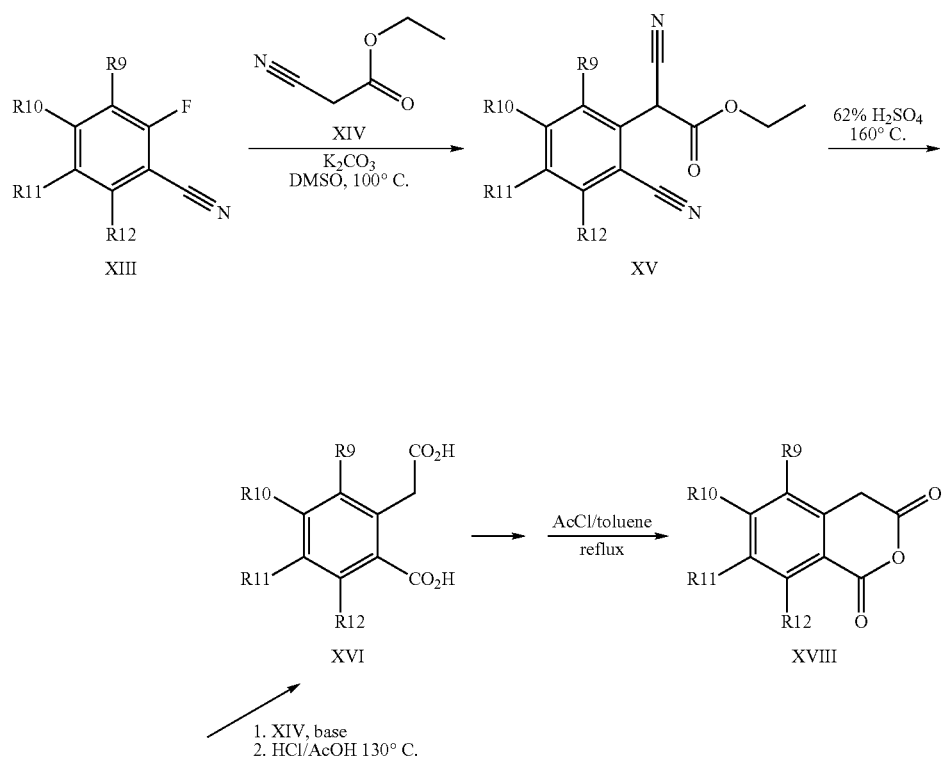
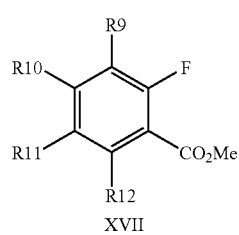
XVII

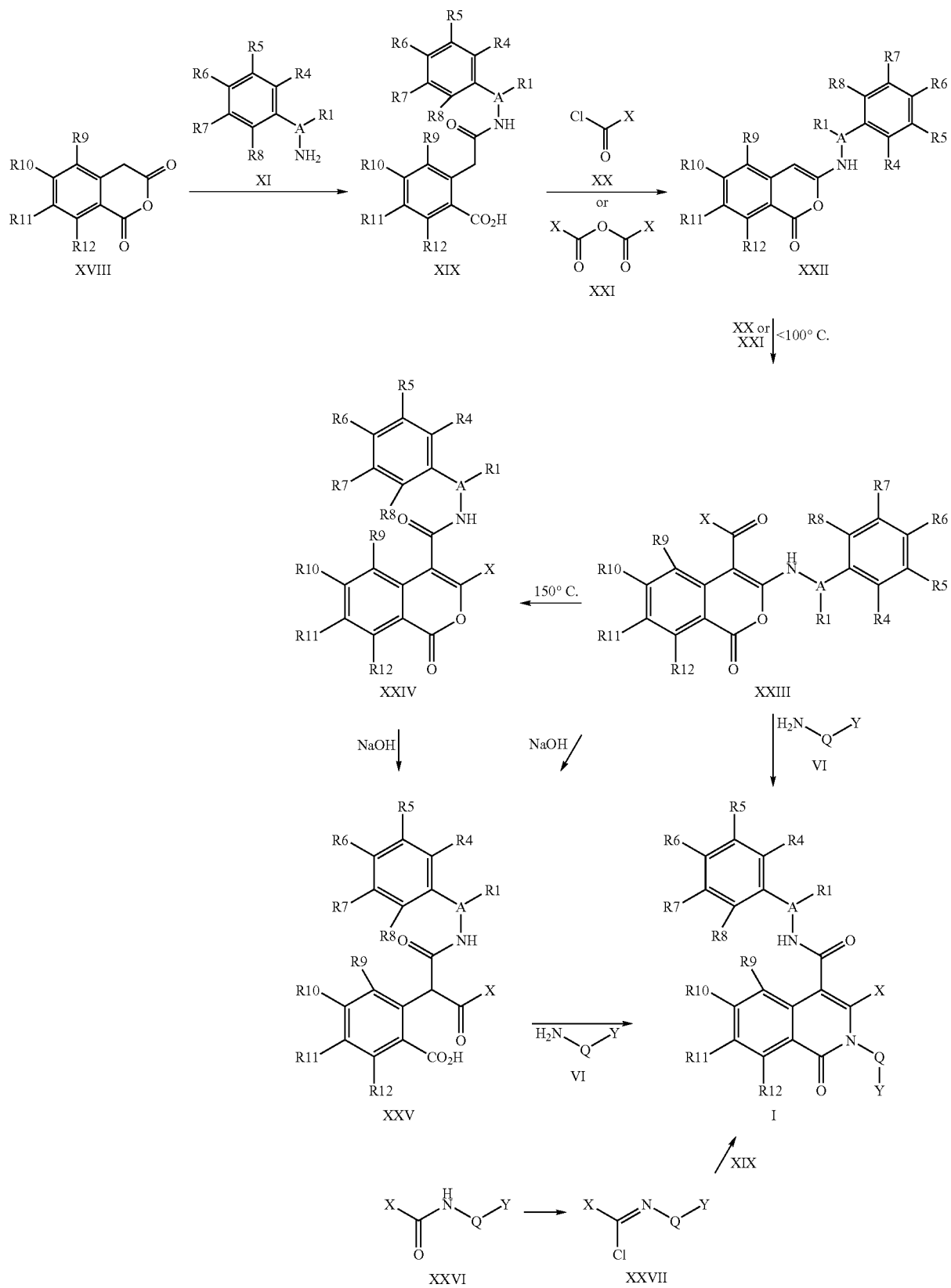

Scheme 5
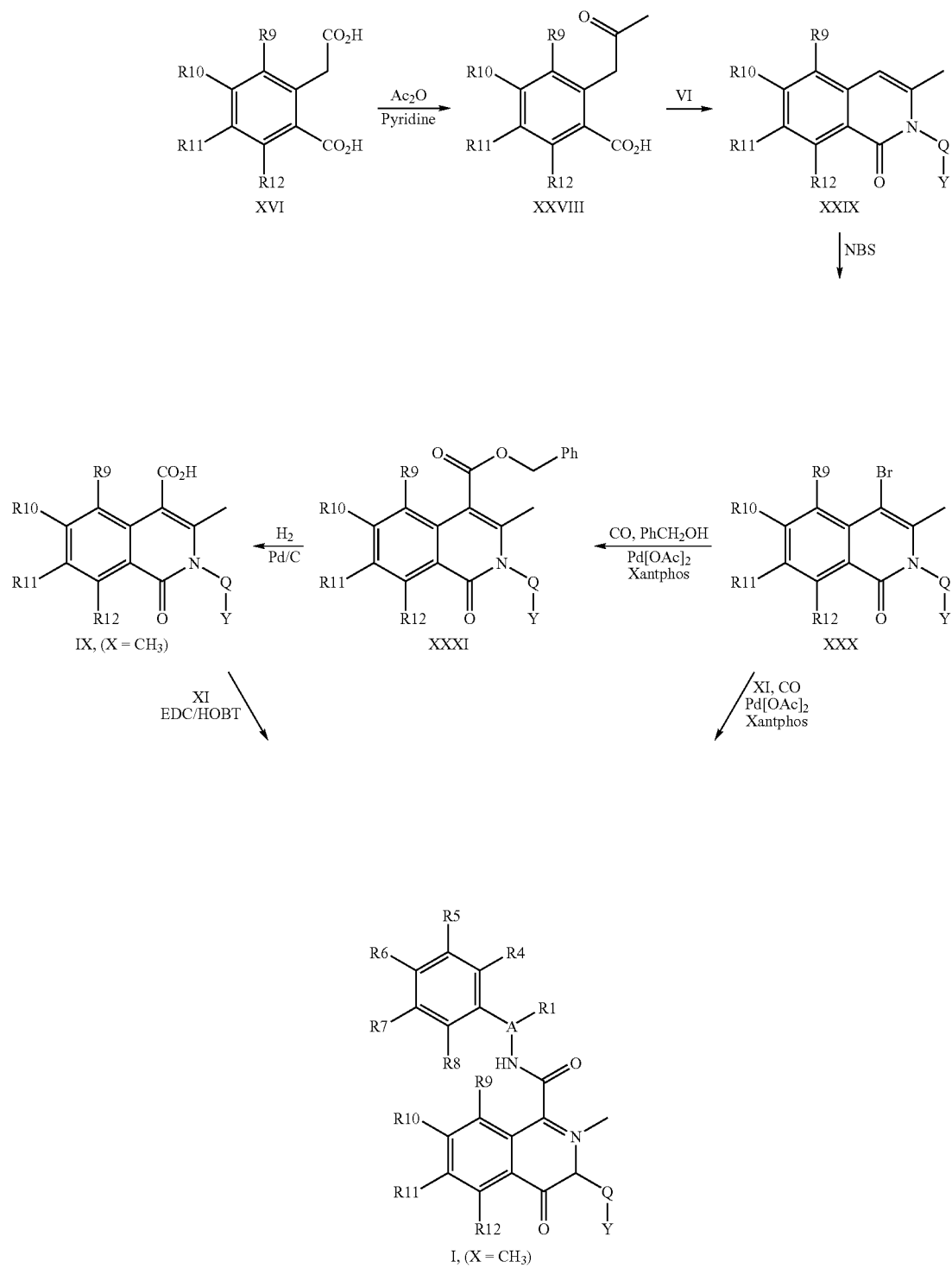
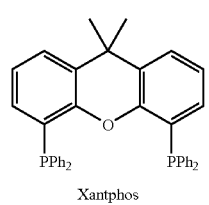
Xantphos

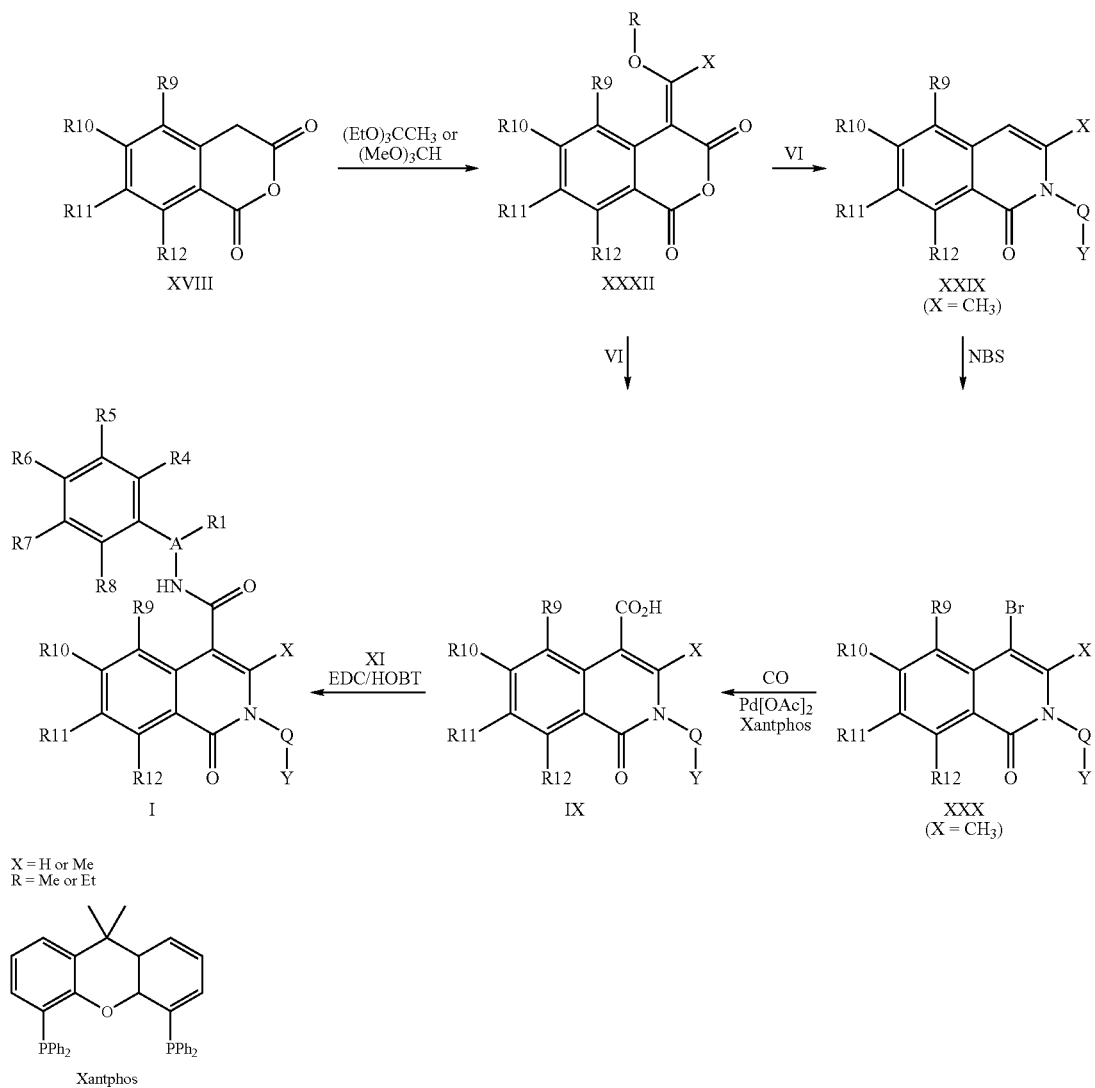
Scheme 6
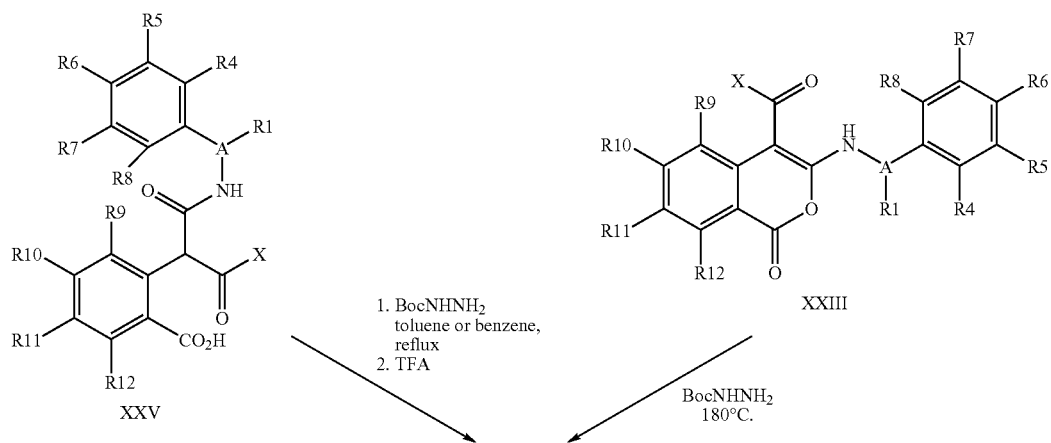
Scheme 7

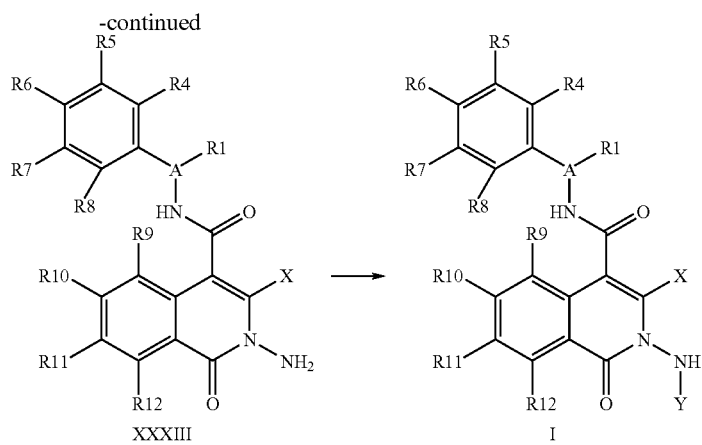

Alternatively, compounds of the general formula I can be prepared starting from substituted homophthalic anhydrides of the general formula XVIII as shown in Scheme 4. Homophthalic anhydrides are either commercially available or can be prepared as shown in Scheme 3 starting from corresponding fluorobenzonitriles or fluorobenzoates of the general formula XIII and XVII, respectively. They undergo aromatic nucleophilic substitution reaction with ethyl cyanoacetate XIV in the presence of base such as potassium carbonate or cesium carbonate under heating conditions in appropriate solvent such as dimethylsulfoxide. The coupling products are hydrolyzed in the presence of strong acids such as sulfuric or hydrochloric acids in water under heating conditions with the formation of diacids of the general formula XVI. Finally, the diacids are converted into the homophthalic anhydrides of the general formula XVIII in the presence of dehydrating agent such as but not limited to acetyl chloride without a solvent or in the appropriate solvent such as toluene under heating conditions such as reflux.

Homophthalic anhydrides of the general formula XVIII can be regioselectively converted into the acid-amides of the general formula XIX at room temperature or under heating conditions in the appropriate solvent such as acetonitrile. Then they are treated with appropriate acid anhydrides or acid chlorides of the general formula XX and XXI, respectively, in the absence or presence of base such as triethyl amine and DMAP in the appropriated solvent, usually in acetonitrile, at room temperature or under mild heating conditions (T<+100° C.). This transformation first provides intermediate ketene-aminals of the general formula XXII, which undergo further acylation reaction with the formation of ketene-aminals of the general formula XXIII. Further heating at higher temperature such as at +150° C. leads to the rearrangement with the formation of amides of the general formula XIV. Compounds of the general formula XXIII and XXIV can be readily hydrolyzed at ambient temperature with an appropriate base such as sodium hydroxide in aqueous methanol or aqueous tetrahydrofurane as a solvent. The obtained keto-acids of the general formula XXV or ketene-aminals of the general formula XXIII are converted to the final compounds of the invention of the general formula I by condensation with amino compounds of the general formula VI under the same conditions as described above for condensation with keto-acids of the general formula IV. In some cases, this condensation can be performed with amino compounds bearing protective groups on the additional nitrogen present in the molecule (scheme 7).

Then the protective group is removed and this nitrogen can be further derivatised e.g. by a reductive alkylation as shown in scheme 7.

Alternatively, acid-amides of the general formula XIX can be converted directly to the compounds of the invention of the general formula I by condensation with appropriate imidoyl chlorides of the general formula XXVII which are readily available from corresponding amide of the general formula XXVI, which are easily prepared by well-known coupling between amino compounds of the general formula VI and corresponding carboxylic acids or their anhydrides or acid chlorides of the general formula XX and XXI, respectively.

In addition to the above methods, carbonylation reaction, in particular, the three-component coupling of an aryl halide, carbon monoxide, and a nucleophile, such as amine or alcohol (Schoenberg, A.; Bartoletti, I.; Heck, R. F. *J. Org. Chem.* 1974, 39, 3318; Schoenberg, A.; Heck, R. F. *J. Org. Chem.* 1974, 39, 3327) can be used in a key step as illustrated in scheme 5. Thus, diacids of the general formula XVI are converted into keto-acids of the general formula XXVIII in one-pot acylation—decarboxylation reaction in acetic anhydride (in the case of acetic anhydride, the substituent X is Me) and in the presence of pyridine followed by condensation with amino compounds of the general formula VI with formation of isoquinolinones of the formula XXIX. They are regioselectively brominated with N-bromosuccinimide with formation of bromides of the general formula XXX. The aminocarbonylation reaction with bromides of the general formula XXX in the presence of amines of the general formula XI under an atmosphere of carbon monoxide promoted by a catalyst, for example palladium acetate—Xanthphos (Kranenburg, M.; van der Burgt, Y. E. M.; Kamer, P. C. J.; van Leeuwen, P. W. N. M. *Organometallics* 1995, 14, 3081) leads to the formation of compounds of the invention of the general formula I where X is Me. Alternatively, carbonylation reaction in the presence of alcohols such as benzyl alcohol under the same conditions leads to formation of benzyl esters of the general formula XXXI, which are readily converted into acids of the general formula IX by palladium catalyzed hydrogenation reaction followed by condensation with amines of the general formula XI as described above (see scheme I).

Alternatively, homophthalic anhydrides of the general formula XVIII are converted into enolethers of the general formula XXXII by refluxing in ortho-esters such as triethyl orthoacetate or trimethyl orthoformate. Depending on the substituent X (X=Me or H) and the amino compound of the general formula VI, the reaction with VI under heating conditions in the appropriate solvent such as ethanol or acetonitrile may provide either acids of the general formula IX or decarboxylated compounds of the general formula XXIX. The latter can be converted into acids of the general formula IX as described above (scheme 5) by bromination and carbonylation reactions. As also described above, acids of the general formula IX are readily converted into compounds of the invention.

Scheme 8

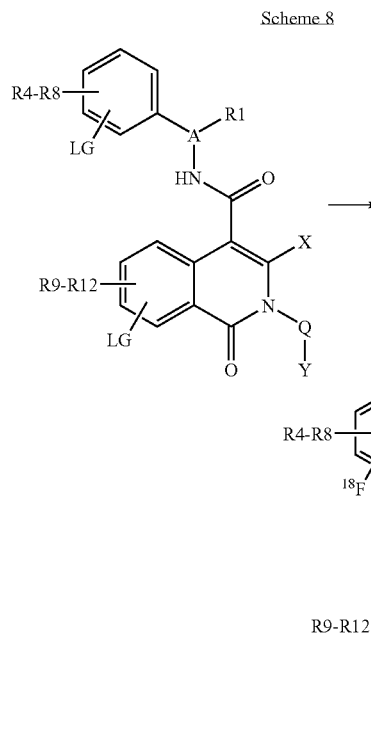

where one or two of R4-R12 are a leaving group (LG) such as but not limited to fluoride, chloride, bromide, nitro, tertiary amine or iodoarene.

Fluorine-18 labelled compounds of formula Ia can be prepared by substitution of a leaving group (LG) with fluoride-18 anions as shown in scheme 8.

Scheme 9

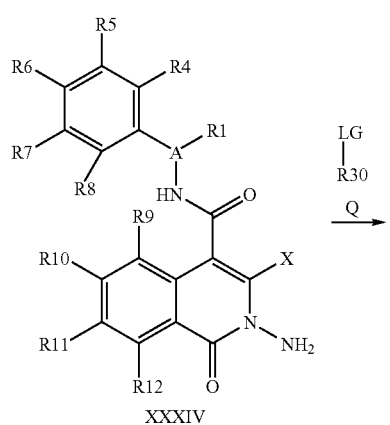

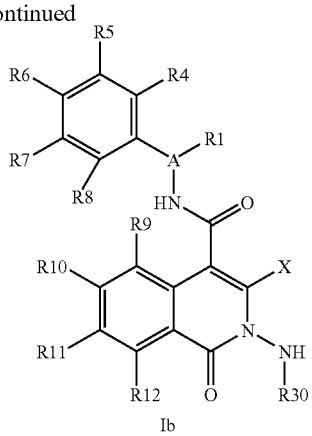

where LG is a leaving group such as but not limited to chloride, bromide or trifluoromethylsulfonate and R30 is a C2-4 alkyl, where one carbon atom is a $^{11}C$-isotope, or the $C_{2-4}$ alkyl is substituted with 1-2 $^{18}F$-isotopes.

Isotope labelled compounds of formula Ib can be prepared by reaction of compounds of formula XXXIV with isotope labelled alkylating reagents such as compounds of formula Q as shown in scheme 9.

Scheme 10

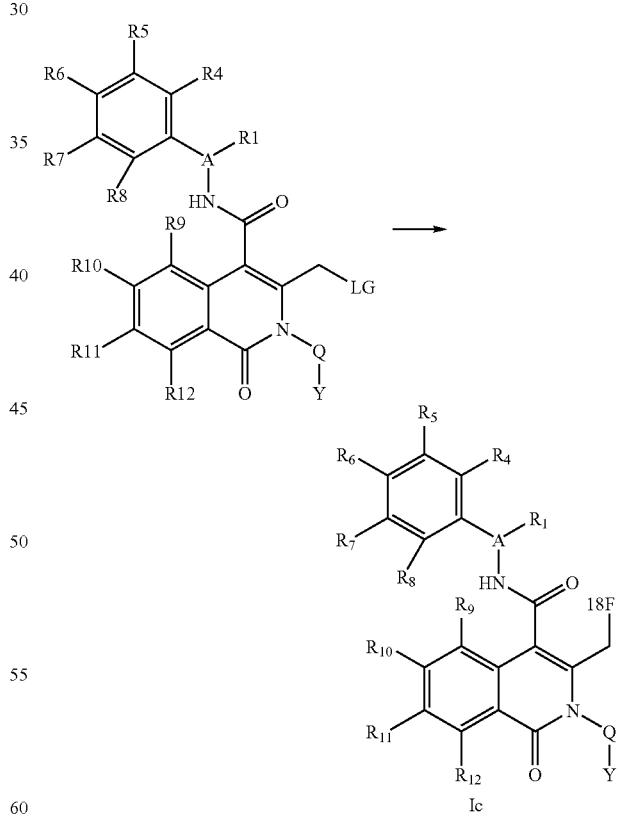

where LG is a leaving group such as but not limited to chloride, bromide or trifluoromethylsulfonate.

Fluorine-18 labelled compounds of formula Ic can be prepared by substitution of a leaving group (LG) with fluoride-18 anions as shown in scheme 10.

Scheme 11

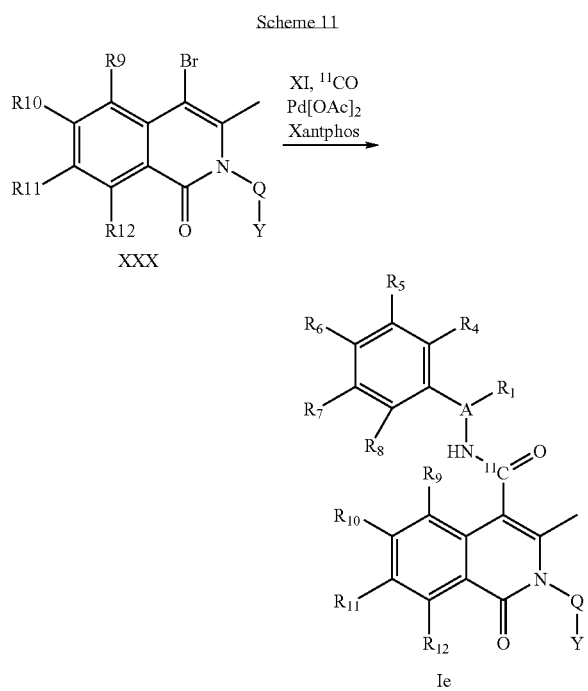

Carbon-11 labelled compounds of formula Ie can be prepared by the aminocarbonylation reaction with bromides of the general formula XXX in the presence of amines of the general formula XI under an atmosphere of carbon-11 monoxide promoted by a catalyst, for example palladium acetate—as shown in scheme 11.

EXAMPLES

Analytical LC-MS, method A (used in most cases unless noted otherwise): data were obtained on a Sciex API 150EX analytical LC/MS system equipped with Applied Biosystems API150EX single qaudrupole mass spectrometer and atmospheric pressure photo ionisation (APPI) ion source, Shimadzu LC10ADvp LC pumps (3×), Shimadzu SPD-M20A photodiode array detector, SEDERE Sedex 85—low temperature Evaporative Light Scattering Detector (ELSD), Shimadzu CBM-20A system controller, Gilson 215 autosampler and Gilson 864 degasser controlled by Analyst Software. Column: 30×4.6 mm Waters Symmetry C18 column with 3.5 µm particle size; Injection Volume: 15 µL; Column temperature: 60° C.; Solventsystem: A=water/trifluoroacetic acid (100:0.05) and B=water/acetonitrile/trifluoroacetic acid (5:95:0.035); Method: Linear gradient elution with 10% B to 100% B in 2.4 minutes then with 10% B in 0.4 minutes and with a flow rate of 3.3 mL/minute. The retention times ($t_R$) are expressed in minutes based on UV-trace at 254 nm.

Analytical LC-MS, method B: data were obtained on a Sciex API300 analytical LC/MS system equipped with Applied Biosystems API300 triple qaudrupole mass spectrometer with atmospheric pressure photo ionisation (APPI) ion source, Shimadzu LC10ADvp LC pumps (3×), Shimadzu SPD-M20A photodiode array detector, Polymer Labs PL-ELS 2100—low temperature Evaporative Light Scattering Detector (ELSD), Shimadzu SCL10A VP system controller, Gilson 215 autosampler and Gilson 864 degasser controlled by Analyst Software. Column: Symmetry C18 3.5 µm, 4.6× 30 mm 30×4.6 mm; Injection Volume: 5 µL; Column temperature: 60° C.; Solventsystem: A=water/trifluoroacetic acid (100:0.05) and B=water/acetonitrile/trifluoroacetic acid (5:95:0.035); Method: Linear gradient elution with 10% B to 100% B in 1.45 minutes then with 10% B in 0.55 minutes and with a flow rate of 5.5 mL/minute:

| Time, min. | % B |
|---|---|
| 0.00 | 10.0 |
| 1.45 | 100.0 |
| 1.55 | 10.0 |
| 2.0 | 10.0 |

The retention times ($t_R$) are expressed in minutes based on UV-trace at 254 nm.

Analytical LC-MS, method C: The same conditions as analytical LC-MS, method A but with the following modifications: Solvent B: Methanol with 0.035% TFA; Flow: 3.0 ml/min; Gradient: 0.01 min 17% B (v/v); 0.27 min 28% B; 0.53 min 39% B; 0.80 min 50% B; 1.07 min 59% B; 1.34 min 68% B; 1.60 min 78% B; 1.87 min 86% B; 2.14 min 93% B; 2.38 min 100% B; 2.40 min 17% B; 2.80 min 17% B.

Preparative LC-MS purification was performed on the same Sciex API 150EX system equipped with Gilson 333 and 334 pumps, Shimadzu LC10ADvp pump, Gilson UV/VIS 155 UV detector, Gilson 233XL autosampler, Gilson FC204 fraction, Gilson 506C system interface, Gilson 864 degasser, DIY flowsplitter (approx. 1:1000), and LC Packings Accurate flowsplitter (1:10.000@140 ml/min). The MS and fraction collector was controlled by Masschrom software (Macintosh PC), the LC system was controlled by Unipoint software. For a small scale (<20 mg) purification fractions were collected in 4 ml vials using Symmetry C18 5 µm, 10×50 mm column, injection volume of 0-300 µL, flow rate of 5.7 ml/min and duration of 8 min. Gradient:

| Time, min. | % B |
|---|---|
| 0.00 | 10.0-50.0 (variable, depending on the sample) |
| 7.00 | 100.0 |
| 7.10 | 10.0-50.0 |
| 8.00 | 10.0-50.0 |

LC—High resolution MS was performed on Bruker Daltonics micrOTOF instrument with electrospray ion source and time-of-flight mass detector.

$^1$H NMR spectra were recorded at 500.13 MHz on a Bruker Avance DRX-500 instrument at T=303.3 K. $^{13}$C NMR and $^{19}$F NMR were recorded on the same instrument. Variable temperature $^1$H NMR spectra were recorded at 250 MHz on a Bruker Avance DPX-250 instrument. Deuterated dimethyl sulfoxide (DMSO-$d_6$, 99.8% D) was used as solvent unless noted otherwise. Tetramethylsilane was used as internal reference standard unless noted otherwise. Chemical shift values are expressed in ppm-values relative to tetramethylsilane unless noted otherwise. The following abbreviations or their combinations are used for multiplicity of NMR signals: s=singlet, d=doublet, t=triplet, q=quartet, qui=quintet, h=heptet, dd=double doublet, ddd=double double doublet, dt=double triplet, dq=double quartet, tt=triplet of triplets, m=multiplet and br=broad or broad singlet.

Microwave experiments were performed in sealed process vials or reactors using an Emrys Synthesizer or Emrys Optimizer EXP from Personal Chemistry or a Milestone Microsynth instrument from Milestone. When a reaction was heated in a microwave instrument, it was cooled to 25° C. before the next process step.

Preparation of Intermediates

Synthesis of homophthalic anhydrides of the general formula XVIII:

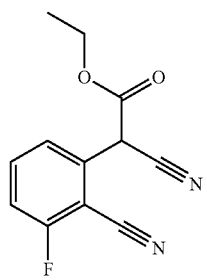

Cyano-(2-cyano-3-fluoro-phenyl)-acetic acid ethyl ester

A mixture of cyanoacetic acid ethyl ester (26.7 mL, 251 mmol), 2,6-difluorobenzonitrile (33.2 g, 239 mmol) and potassium carbonate (82.5 g, 597 mmol) in dimethyl sulfoxide (120 mL) was stirred at +55° C. for 16 hours and poured into ice-water mixture (ca. 400 mL). It was acidified with conc. aq. HCl with caution ($CO_2$ evolution) and extracted with ethyl acetate (600 ml). The organic phase was washed with brine (100 mL) and evaporated to give 55.1 g of a pale yellow solid that was used in the next step without further purification. $^1$H NMR (500 MHz, $CDCl_3$): 1.35 (t, J=7.0 Hz, 3H), 4.34 (m, 2H), 5.13 (s, 1H), 7.33 (t, J=8.4 Hz, 1H), 7.57 (d, J=7.9 Hz, 1H), 7.33 (dd, J=7.9 Hz, J=13.9 Hz, 1H).

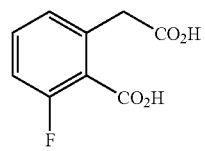

2-Carboxymethyl-6-fluoro-benzoic acid

A mixture of 62% sulfuric acid (2:1 conc. $H_2SO_4$ in water, 400 ml) and cyano-(2-cyano-3-fluoro-phenyl)-acetic acid ethyl ester (52.0 g, 224 mmol) was stirred at +150° C. overnight (16 hours). The reaction mixture was poured into ice (ca. 500 g) and 10.8 N aq. NaOH (500 mL) was added with cooling. The mixture was extracted with ethyl acetate (3×500 mL) and the combined organic solution was washed with brine, dried over $MgSO_4$ and evaporated to give 40.28 g of crude product that was used in the next step without further purification. The analytical sample was prepared by recrystallisation from toluene-ethyl acetate. $^1$H NMR (500 MHz, DMSO-$d_6$): 3.4 (br, $CO_2H+H_2O$), 3.77 (s, 2H), 7.17 (d, J=7.9 Hz, 1H), 7.2 (overlapping t (unres. dd), 1H), 7.45 (dd, J=7.9 Hz, J=13.9 Hz, 1H), 12.95 (br, $CO_2H$).

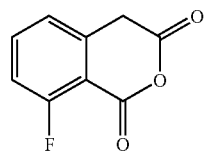

8-Fluoro-isochroman-1,3-dione

2-Carboxymethyl-6-fluoro-benzoic acid (130 mg, 0.65 mmol) in acetyl chloride (2 ml) was heated under microwave irradiation at 150° C. for 10 min then concentrated in vacuo to give the title product (120 mg, 100% yield). The compound is hydroscopic and slowly decomposes back to the starting diacid in wet solvents or under moisturized atmosphere. $^1$H NMR (500 MHz, DMSO-$d_6$): 4.29 (s, 2H), 7.27 (d, J=7.8 Hz, 1H), 7.34 (dd, J=8.5 Hz, J=11 Hz, 1H), 7.76 (dt, J=5.3 Hz, J=8 Hz, 1H).

The following homophthalic anhydrides were obtained analogously by the described above 3-step procedure from corresponding fluorobenzonitriles and ethyl cyanoacetate:

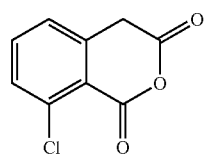

8-Chloro-isochroman-1,3-dione

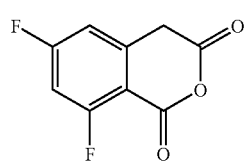

6,8-Difluoro-isochroman-1,3-dione

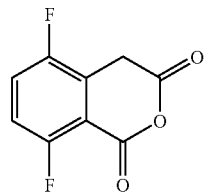

5,8-Difluoro-isochroman-1,3-dione

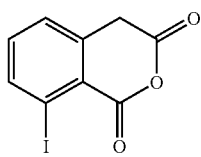

8-Iodo-isochroman-1,3-dione

Synthesis of chiral and racemic amines of the general formula XI:

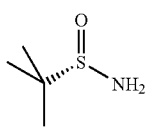

(S)-(−)-2-Methyl-2-propanesulfinamide

The title chiral auxiliary was prepared according to a described procedure for the (R)-(+)-enantiomer by D. J. Weix and J. A. Ellman *Organic Syntheses* 2005, 82, 157.

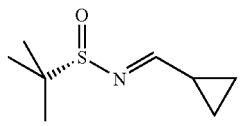

(S)-2-Methyl-2-propanesulfinic acid 1-cyclopropyl-methylideneamide

The title compound was prepared according to a general procedure described by G. Liu, D. A. Cogan, T. D. Owens, T. P. Tang, and J. A. Ellman *J. Org. Chem.* 1999, 64, 1278: A mixture of cyclopropanecarboxaldehyde (35.0 g, 0.5 mol), 2-methyl-2-propanesulfinic acid 1-cyclopropyl-methylideneamide (30 g, 0.25 mol) and anhydrous CuSO$_4$ (120 g, 0.75 mol) in CH$_2$Cl$_2$ (1500 mL) was stirred at room temperature overnight. The reaction mixture was filtered and evaporated to give the title compound (39 g, yield 95%), which was used in the next step without further purification.

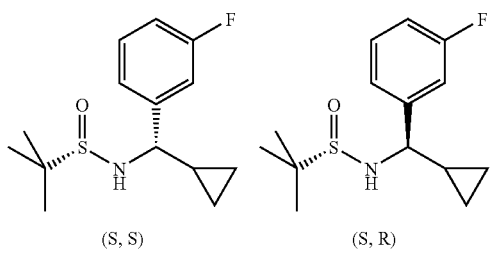

(S)-2-Methyl-2-propanesulfinic acid [(S)-cyclopropyl-(3-fluoro-phenyl)-methyl]-amide and (S)-2-Methyl-2-propanesulfinic acid [(R)-cyclopropyl-(3-fluoro-phenyl)-methyl]-amide The title compounds were obtained according to a general described procedure for 1,2-stereoselective addition of organometallic reagents to sulfinyl imines by D. A. Cogan, G. Liu, J. A. Ellman, *Tetrahedron* 1999, 55, 8883.

Procedure A: To anhydrous lithium chloride (1.7 g, 40 mmol) THF (20 ml) was added under nitrogen followed by slow addition of i-PrMgCl (22 mL, 2 M in THF) and the obtained mixture was stirred at r.t. overnight. The obtained i-PrMgCl.LiCl solution was added dropwise to a stirred solution of 1-bromo-3-fluorobenzene (5.6 g, 33 mmol) in THF (25 ml) at 0° C. and stirring continued for 2 hours. The obtained Grignard reagent was added to a solution of (S)-2-methyl-2-propanesulfinic acid 1-cyclopropyl-methylideneamide (2.5 g, 14 mmol) in CH$_2$Cl$_2$ (60 mL) at −48° C. The mixture was stirred at −48° C. for 5 hours and then at room temperature overnight. The reaction mixture was quenched by addition of aq. sat. NH$_4$Cl (50 mL) and extracted with CH$_2$Cl$_2$ (3×100 mL). The combined organic solution was dried (Na$_2$SO$_4$) and evaporated to give a crude mixture, which was purified by column chromatography on silica gel (EtOAc/petroleum ether=1/10). The obtained mixture of diastereoisomers was resolved by SFC to give the title (S,S)-isomer as the major product (1.5 g, yield 37.5%) and the title (S,R)-isomer (0.16 g, yield: 4.0%).

Procedure B: Alternatively, to a suspension of Mg (13.4 g, 0.55 mol) in 50 mL of anhydrous THF at 50° C. a solution of 1-bromo-3-fluorobenzene (89.0 g, 0.50 mol) was added dropwise. The mixture was stirred for 2 hours at +50° C. and then it was added dropwise to a solution of (S)-2-methyl-2-propanesulfinic acid 1-cyclopropyl-methylideneamide (78.0 g, 0.46 mol) in 100 mL of THF at 50-60° C. and stirred for 2 hours. It was quenched with aq. sat. NH$_4$Cl (100 ml), water (300 mL), filtered, and the both solid and filtrate were extracted with hot ethyl acetate (600 mL) and evaporated in vacuo. The residue was crystallized from a mixture of ethyl acetate and petroleum ether (1:1, 200 mL) at −20° C. to give 80 g of the title (S,S)-isomer as a white powder, 66% yield, de 100% according to chiral HPLC. $^1$H NMR (CDCl$_3$, 400 MHz, TMS=0 ppm): 7.34-7.28 (m, 1H), 7.16-7.12 (m, 2H), 7.00-6.96 (m, 1H), 3.68 (dd, J=8.8 Hz, 3.2 Hz, 1H), 3.52 (s, 1H), 1.42 (s, 9H), 1.15-1.08 (m, 1H), 0.84-0.75 (m, 1H), 0.69-0.61 (m, 1H), 0.55-0.46 (m, 1H), 0.28-0.21 (m, 1H).

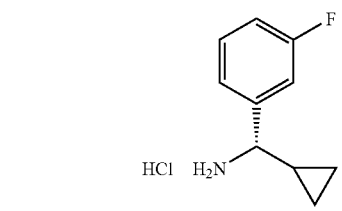

(S)-(+)-C—[C-Cyclopropyl-C-(3-fluoro-phenyl)-methylamine hydrochloride

To a saturated solution of HCl in anhydrous dioxane (400 ml) (S)-2-methyl-2-propanesulfinic acid [(S)-cyclopropyl-(3-fluoro-phenyl)-methyl]-amide (80 g, 0.3 mol) was added at 0° C. After stirring at r.t. for 1 hour, the reaction mixture was evaporated in vacuo. The residue was washed with anhydrous ether (2×100 ml) and dried in vacuo to give 56 g of the title compound as a white solid, yield 93%, ee 100% according to chiral HPLC. $[\alpha]_D^{20}$=+52.69 (c=10 mg/mL, CH$_3$OH). $^1$H NMR (CD$_3$OD, 400 MHz, TMS=0): 7.44-7.39 (m, 1H), 7.25-7.19 (m, 2H), 7.12-7.07 (m, 1H), 3.56 (d, J=10.0 Hz, 1H), 1.37-1.28 (m, 1H), 0.78-0.75 (m, 1H), 0.61-0.55 (m, 2H), 0.39-0.36 (m, 1H).

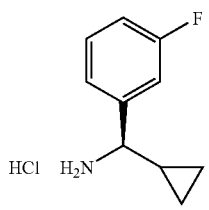

(R)-(−)-C—[C-Cyclopropyl-C-(3-fluoro-phenyl)]-methylamine hydrochloride

The title compound was prepared according to the above identical procedure from (S)-2-methyl-2-propanesulfinic acid [(R)-cyclopropyl-(3-fluoro-phenyl)-methyl]-amide (0.16 g, 0.6 mmol) to give 0.116 g of the title compound as a white solid. $[\alpha]_D^{20} = -49.18$ (c=10 mg/mL, $CH_3OH$), ee 100%. $^1H$ NMR ($CD_3OD$, 400 MHz, TMS=0): identical with (S)-enantiomer.

The following enantiomerically pure amine hydrochlorides were obtained analogously in three-step procedure starting from condensation of the corresponding aldehyde with chiral auxiliary, stereoselective Grignard addition where the mixture of diastereoisomers was resolved either by recrystallisation or by chromatography (SFC or column) and the major (S,S)-diastereoisomer was finally converted to a chiral amine with HCl.

| Structure (HCl salt) | Chemical name | $[\alpha]^{20}D$, (10 mg/ml) MeOH | ee (chiral HPLC) | $^1H$ NMR ($CD_3OD$, 400 MHz) |
|---|---|---|---|---|
| | C-((S)-C-Cyclobutyl-C-phenyl)-methylamine | +17.57 | 95.4 | 7.37-7.31 (m, 5H), 4.12 (d, J = 10.4 Hz, 1H), 2.84-2.75 (m, 1H), 2.21-2.13 (m, 1H), 1.99-1.64 (m, 5H). |
| | C-[(S)-C-Cyclobutyl-C-(3-fluoro-phenyl)]-methylamine | +19.45 | 100 | 7.48-7.44 (m, 1H), 7.24-7.15 (m, 3H), 4.26 (d, J = 10.4 Hz, 1H), 2.87-2.84 (m, 1H), 2.25-2.24 (m, 1H), 2.05-1.76 (m, 5H). |
| | C-[(S)-C-Cyclobutyl-C-(4-fluoro-phenyl)]-methylamine | +26.98 | 100 | 7.45-7.41 (m, 2H), 7.18-7.14 (m, 2H), 4.22 (d, J = 10.6 Hz, 1H), 2.89-2.81 (m, 1H), 2.28-2.21 (m, 1H), 2.05-1.71 (m, 5H). |
| | C-[(S)-C-Cyclopropyl-C-(3,4-difluoro-phenyl)]-methylamine | +44.26 | 96 | 7.50-7.32 (m, 3H), 3.62 (d, J = 10.4 Hz, 1H), 1.38 (m, 1H), 0.86 (m, 1H), 0.68 (m, 1H), 0.62 (m, 1H), 0.45 (m, 1H) |
| | C-[(S)-C-Cyclobutyl-C-(3,4-difluoro-phenyl)]-methylamine | +27.22 | >99 | 7.41-7.32 (m, 2H), 7.25 (m, 1H), 4.26 (d, J = 10.4 Hz, 1H), 2.48 (m, 1H), 2.24 (m, 1H), 2.05-1.72 (m, 5H) |
| | (S)-1-(4-Fluoro-phenyl)-propylamine | +14.83 | 98.7 | 7.53-7.50 (m, 2H), 7.24-7.19 (m, 2H), 4.21 (dd, J = 9.2 Hz, 5.6 Hz, 1H), 2.13-1.91 (m, 2H), 0.89 (t, J = 7.2 Hz, 3H). |
| | C-[(S)-C-Cyclopropyl-C-(4-fluoro-phenyl)]-methylamine | +47.25 | 98.9 | 7.50-7.46 (m, 2H), 7.19-7.14 (m, 2H), 3.56 (d, J = 10.0 Hz, 1H), 1.40-1.31 (m, 1H), 0.83-0.76 (m, 1H), 0.67-0.54 (m, 2H), 0.40-0.31 (m, 1H) |

Synthesis of acid-amides of the general formula XIX:

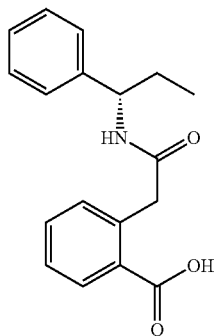

2-[((S)-1-Phenyl-propylcarbamoyl)-methyl]-benzoic acid

A mixture of homophthalic anhydride (810 mg, 5 mmol) and (S)-(−)-1-phenylpropylamine (676 mg, 5 mmol) in acetonitrile (15 ml) was heated under microwave irradiation at +150° C. for 15 min. White precipitate was collected by filtration, washed with heptane and dried in vacuo to give pure title compound in 72% yield (1.065 g). Alternatively, to a stirred solution of homophthalic anhydride (16.214 g, 0.1 mol) in acetonitrile (100 ml) (S)-(−)-1-phenylpropylamine (13.83 g, 0.102 mol) was added dropwise (exothermic reaction) and the obtained reaction mixture was refluxed for 5 min. It was allowed to cool and the product was isolated by filtration as above to give 23.4 g of colourless solid, 79% yield. LC-MS (m/z) 298.5 (MH$^+$); $t_R$=1.11. $^1$H NMR (500 MHz, DMSO-$d_6$): 0.84 (t, J=7.3 Hz, 3H), 1.67 (quintet, J=7.3 Hz, 2H), 3.85 (d of AB system, J=15.1 Hz, 1H), 3.95 (d of AB system, J=15.1 Hz, 1H), 4.66 (q, J=7.6 Hz, 1H), 7.2 (unres. m, 1H), 7.25-7.34 (m, 5H), 7.45 (t, J=7.3 Hz, 1H), 7.8 (d, J=7.8 Hz, 1H), 8.39 (br. d, J=7.7 Hz, 1H, NH).

The following compounds were obtained analogously from corresponding homophthalic anhydrides and amines of the general formula XVIII and XI, respectively. The reactions were usually run at room temperature and the products were isolated by extraction or filtration and used in the next steps without further purification.

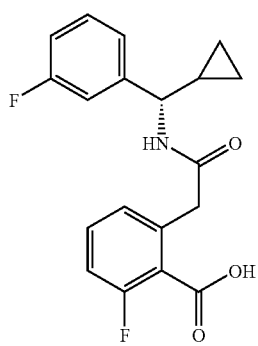

2-({[(S)-Cyclopropyl-(3-fluoro-phenyl)-methyl]-carbamoyl}-methyl)-6-fluoro-benzoic acid LC-MS (m/z) 346.2 (MH$^+$); $t_R$=1.14. $^1$H NMR (500 MHz, DMSO-$d_6$): 0.35 (m, 1H), 0.39 (m, 1H), 0.5 (m, 2H), 1.12 (m, 1H), 3.68 & 3.74 (two d of AB system, J=15.2 Hz, 2H, CH$_2$), 4.25 (t, J=8.5 Hz, 1H), 7.05 (dt, J=2.2, 8.05 Hz, 1H), 7.13 (d, J=8.1 Hz, 1H), 7.16-7.21 (m, 2H), 7.35 (m, 1H), 7.42 (m, 1H), 8.66 (d, J=8.2 Hz, 1H, NH), 13.44 (br., CO$_2$H).

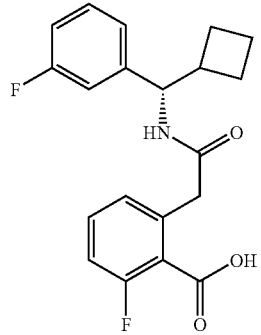

2-({[(S)-Cyclobutyl-(3-fluoro-phenyl)-methyl]-carbamoyl}-methyl)-6-fluoro-benzoic acid LC-MS (m/z) 360.2 (MH$^+$); $t_R$=1.31.

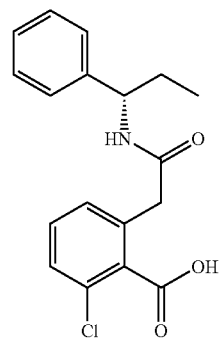

2-Chloro-6-[((S)-1-phenyl-propylcarbamoyl)-methyl]-benzoic acid

LC-MS (m/z) 332.2 (MH$^+$); $t_R$=1.19. $^1$H NMR (500 MHz, DMSO-$d_6$): 0.84 (t, J=7.3 Hz, 3H), 1.68 (quintet, J=7.3 Hz, 2H), 3.54 & 3.61 (two d of AB system, J=15.3 Hz, 2H, CH$_2$), 4.67 (q, J=7.5 Hz, 1H), 7.19-7.4 (m, 8H), 8.48 (d, J=8.3 Hz, 1H, NH), 13.64 (br., CO$_2$H).

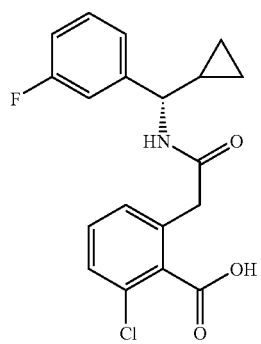

55

2-Chloro-6-({[(S)-cyclopropyl-(3-fluoro-phenyl)-methyl]-carbamoyl}-methyl)-benzoic acid

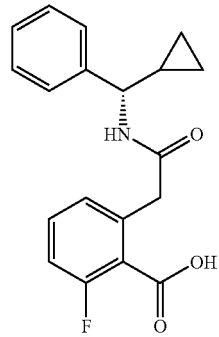

2-{[((S)-Cyclopropyl-phenyl-methyl)-carbamoyl]-methyl}-6-fluoro-benzoic acid

LC-MS (m/z) 328.4 (MH$^+$); $t_R$=1.12.

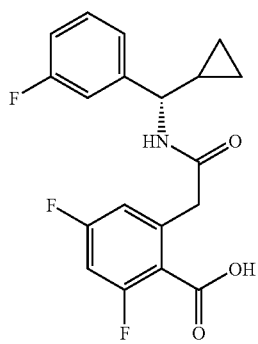

2-({[(S)-Cyclopropyl-(3-fluoro-phenyl)-methyl]-carbamoyl}-methyl)-4,6-difluoro-benzoic acid

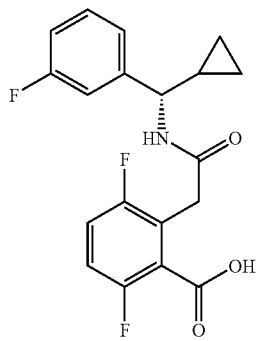

56

2-({[(S)-Cyclopropyl-(3-fluoro-phenyl)-methyl]-carbamoyl}-methyl)-3,6-difluoro-benzoic acid

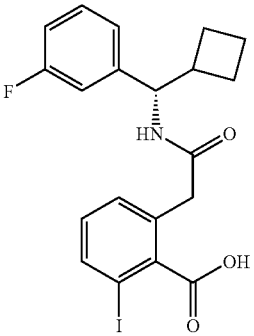

2-({[(S)-Cyclobutyl-(3-fluoro-phenyl)-methyl]-carbamoyl}-methyl)-6-iodo-benzoic acid Synthesis of compounds of the general formula XXIII:

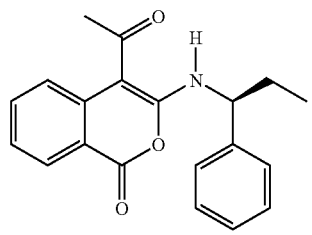

4-Acetyl-3-((S)-1-phenyl-propylamino)-isochromen-1-one

A mixture of 2-[((S)-1-phenyl-propylcarbamoyl)-methyl] benzoic acid (10 g), acetic anhydride (50 ml), and N,N-dimethylaminopyridine (100 mg) was heated at gentle reflux (T$_{max}$=+124° C.) for 7 min and evaporated in vacuo at +50° C. to give the title compound as a yellow-brown solid (11.1 g, purity 98% by NMR). LC-MS (m/z) 322.3 (MH$^+$); $t_R$=1.72. $^1$H NMR (500 MHz, DMSO-d$_6$): 0.89 (t, J=7.2 Hz, 3H), 1.86-1.97 (m, 2H), 2.56 (s, 3H), 4.95 (q, J=7.1 Hz, 1H, CH—NH), 7.26 (t, J=7.5 Hz, 1H), 7.29 (unres. m, 1H), 7.36-7.41 (unres m., 3H), 7.71 (t, J=7.5 Hz, 1H), 7.75 (d, J=8.3 Hz, 1H), 7.98 (d, J=7.8 Hz, 1H), 11.53 (d, J=7.6 Hz, 1H, NH). $^{13}$C APT NMR (125 MHz, DMSO-d$_6$, δ(DMSO-d$_6$)=39.87 ppm): 10.68 (CH$_3$), 30.0 (CH$_2$), 31.57 (CH$_3$), 57.01 (CH), 92.44 (C), 114.88 (C), 124.2 (CH), (CH), 124.26 (CH), 126.65 (CH), 127.8 (CH), 129.05 (CH), 129.93 (CH), 135.71 (CH), 138.68 (C), 141.86 (C), 158.51 (C), 160.55 (C), 194.82 (C, MeCO).

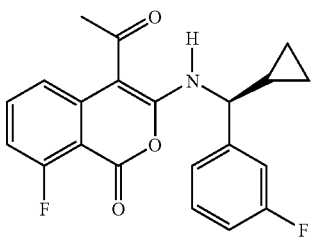

4-Acetyl-3-{[(S)-cyclopropyl-(3-fluoro-phenyl)-methyl]-amino}-8-fluoro-isochromen-1-one A mixture of 2-({[(S)-cyclopropyl-(3-fluoro-phenyl)-methyl]-carbamoyl}-methyl)-6-fluoro-benzoic acid (12.92 g, 37.41 mmol) and acetic anhydride (100 mL, 1 mol) was stirred at +65° C. for 20 hours and evaporated in vacuo (65° C., 10 mbar, 2 hours) to give the title compound as a thick brown oil, which was used in the next step without purification (14.30 g, yield 103.5%, purity 95% according to $^1$H NMR). LC-MS (m/z) 370.1 (MH$^+$); $t_R$=1.65. $^1$H NMR (500 MHz, DMSO-d$_6$): 0.45-0.59 (m, 3H), 0.64 (m, 1H), 1.41 (m, 1H), 2.53 (s, 3H), 4.36 (t unres. dd), 1H), 7.03 (dd, J=8.3, 10.7 Hz, 1H), 7.12 (dt, J=1.9, 8.5 Hz, 1H), 7.27 (d, J=10.2 Hz, 1H), 7.3 (d, J=7.8 Hz, 1H), 7.42 (q, J=7.8 Hz, 1H), 7.53 (d, 8.5 Hz, 1H), 7.7 (m, 1H), 11.3 (d, J=7.3 Hz, 1H, NH).

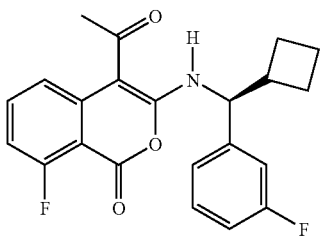

4-Acetyl-3-{[(S)-cyclobutyl-(3-fluoro-phenyl)-methyl]-amino}-8-fluoro-isochromen-1-one LC-MS (m/z) 384.4 (MH$^+$); $t_R$=1.82.

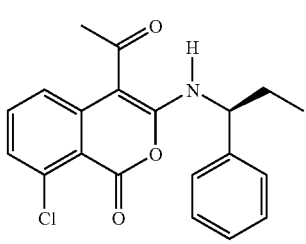

4-Acetyl-8-chloro-3-((S)-1-phenyl-propylamino)-isochromen-1-one

2-Chloro-6-[((S)-1-phenyl-propylcarbamoyl)-methyl]-benzoic acid (11.4 g) and acetic anhydride (50 ml) were heated at 103° C. for 60 min and evaporated to give 12.45 g of brown oil (purity ca 95% according to $^1$H NMR). LC-MS (m/z) 355.2 (MH$^+$); $t_R$=1.82. Analytically pure sample was prepared by recrystallisation (9 g from 30 ml of hot MeCN) to give the title compound (4.41 g) as a pale yellow solid after cooling (dry ice—EtOH bath) and filtration. LC-MS (m/z) 355.2 (MH$^+$; $t_R$=1.82. $^1$H NMR (500 MHz, DMSO-d$_6$): 0.88 (t, J=7.4 Hz, 3H), 1.92 (m, 2H), 2.5 (s, 3H), 4.92 (q, J=7.3 Hz, 1H, CH—NH), 7.27-7.33 (m, 2H), 7.39 (d unres. m), J=4.3 Hz, 4H), 7.59-7.66 (m, 2H), 11.11 (d, J=7.8 Hz, 1H, NH).

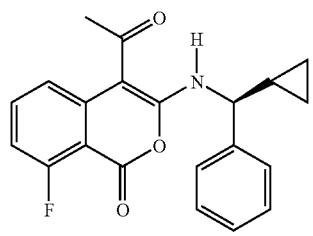

4-Acetyl-3-[((S)-cyclopropyl-phenyl-methyl)-amino]-8-fluoro-isochromen-1-one

LC-MS (m/z) 352.6 (MH$^+$); $t_R$=1.62. $^1$H NMR (500 MHz, DMSO-d$_6$): 0.48 (m, 2H), 0.54 (m, 1H), 0.64 (m, 1H), 1.39 (m, 1H), 2.53 (s, 3H), 4.39 (t unres. dd), 1H), 7.04 (dd, J=8.2, 10.8 Hz, 1H), 7.3 (t, J=7.3 Hz, 1H), 7.39 (t, J=7.6 Hz, 2H), 7.43 (d, J=7.3 Hz, 2H), 7.53 (d, 8.5 Hz, 1H), 7.7 (m, 1H), 11.39 (d, J=7.5 Hz, 1H, NH).

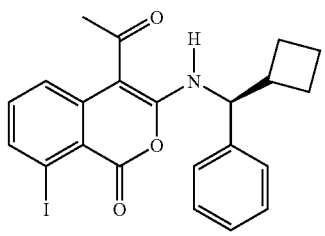

4-Acetyl-3-{[(S)-cyclobutyl-(3-fluoro-phenyl)-methyl]-amino}-8-iodo-isochromen-1-one

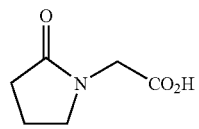

(2-Oxo-pyrrolidin-1-yl)-acetic acid

A mixture of 2-pyrrolidone (2.66 ml, 34 mmol) and NaH (60% in oil, 1.25 g, 31.3 mmol) in THF (75 ml) was stirred until gas evolution ceased (30 min). tert-Butyl 2-bromoacetate (4.45 ml, 30 mmol) was added and stirred at r.t. overnight then partitioned between water (200 ml) and ethyl acetate (200 ml) to give intermediate 2-(oxo-pyrrolidin-1-yl)-acetic acid tert-butyl ester (5.8 g). It was dissolved in acetic acid (40 ml) and cone. aq. HCl (6 ml) with gas evolution observed. After stirring at r.t. for 2 hours it was evaporated and recrystallized from toluene/ethanol to give 2.58 g of the title compound (60% yield). $^1$H NMR (500 MHz, DMSO-d$_6$):

1.95 (quintet, J=7.7 Hz, 2H), 2.24 (t, J=8.1 Hz, 2H), 3.38 (m, overalapping with H₂O (3.35 ppm), 2H), 3.91 (s, 2H), 12.77 (br., 1H).

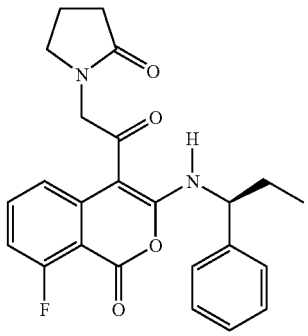

1-{2-[8-Fluoro-1-oxo-3-((S)-1-phenyl-propylamino)-1H-isochromen-4-yl]-2-oxo-ethyl}-pyrrolidin-2-one To a solution of 2-oxo-pyrrolidin-1-yl-acetic acid (1.56 g, 10.9 mmol) in 1,2-dichloroethane (40 ml) oxalyl chloride (0.95 ml, 10.9 mmol) and DMF (1 drop) were added with gas evolution observed. After stirring at r.t. for 1 hour, 2-fluoro-6-[((S)-1-phenyl-propylcarbamoyl)-methyl]-benzoic acid (1.56 g, 4.95 mmol), triethylamine (2.1 ml, 14.9 mmol) and DMAP (85 mg, 0.1 eq.) were added and stirred at r.t. overnight. It was partitioned between mixture of 0.2 M aq. HCl (100 ml)—brine (100 ml) and ethyl acetate (250 ml), washed with water and evaporated to give 1.89 g of crude title compound used in the next step without further purification.

¹H NMR (500 MHz, DMSO-d₆, selected resonances): 4.51 & 4.58 (two d of AB system, J=16.3 Hz, N—CH₂—CO), 4.99 (q, J=7.5 Hz, 1H, CH—NH), 11.31 (d, J=7.9 Hz, 1H, NH).

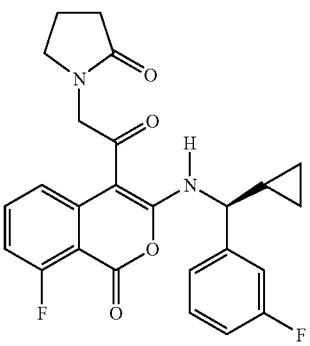

1-[2-(3-{[(S)-Cyclopropyl-(3-fluoro-phenyl)-methyl]-amino}-8-fluoro-1-oxo-1H-isochromen-4-yl)-2-oxo-ethyl]-pyrrolidin-2-one The title compound was prepared analogously and purified by flash chromatography on SiO₂. LC-MS (m/z) 453.3 (MH⁺); t$_R$=1.48.

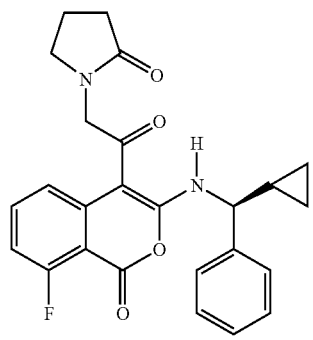

1-(2-{3-[((S)-Cyclopropyl-phenyl-methyl)-amino]-8-fluoro-1-oxo-1H-isochromen-4-yl}-2-oxo-ethyl)-pyrrolidin-2-one The title compound was prepared analogously. LC-MS (m/z) 435.3 (MH⁺); t$_R$=1.43.

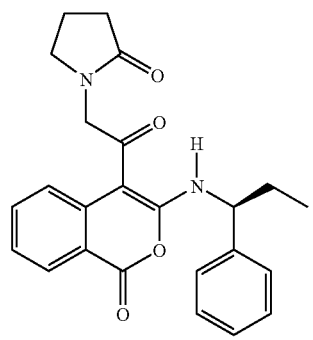

1-{2-Oxo-2-[1-oxo-3-((S)-1-phenyl-propylamino)-1H-isochromen-4-yl]-ethyl}-pyrrolidin-2-one The title compound was prepared analogously. LC-MS (m/z) 405.6 (MH⁺); t$_R$=1.47.

Hydrolysis of compounds of the general formula XXIII into compounds of the general formula XXV:

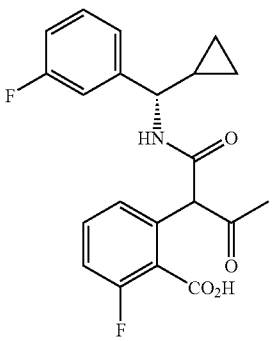

2-(1-{[(S)-Cyclopropyl-(3-fluoro-phenyl)-methyl]-carbamoyl}-2-oxo-propyl)-6-fluoro-benzoic acid 4-Acetyl-3-{[(S)-cyclopropyl-(3-fluoro-phenyl)-methyl]-amino}-8-fluoro-2-benzopyran-1-one (14.30 g, 38.72 mmol)

was dissolved in a mixture of tetrahydrofuran (50 mL) and methanol (50 mL) and placed on an ice/water bath with stirring. NaOH (1 M in $H_2O$, 100 ml) was added and stirring continued for 1 hour. The cold bath removed and the mixture was allowed to warm to r.t. (20° C.) during 1 hour. The reaction mixture was poured into ice-water mixture (200 g+200 ml), followed by slow addition of 2 M aq. HCl (200 mL) and extracted with ethyl acetate (200 mL), washed with sat. aq. NaCl, dried ($Na_2SO_4$), filtered and evaporated to give the title compound (14.65 g, yield 97.7%) as a pale brown foam. The crude product was used in the next step without further purification. LC-MS (m/z) 388.3 ($MH^+$); $t_R$=1.2. $^1H$ NMR (500 MHz, DMSO-$d_6$): a mixture of tautomers and diastereoisomers.

The following compounds were prepared analogously:

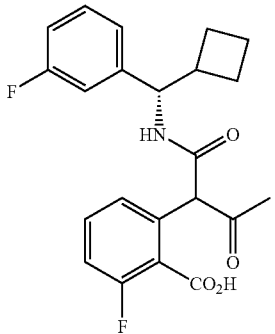

2-(1-{[(S)-Cyclobutyl-(3-fluoro-phenyl)-methyl]-carbamoyl}-2-oxo-propyl)-6-fluoro-benzoic acid LC-MS (m/z) 402.2 ($MH^+$); $t_R$=1.36.

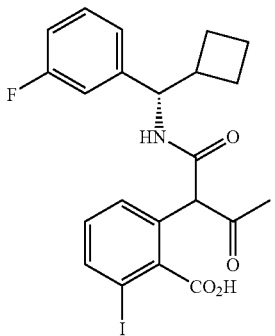

2-(1-{[(S)-Cyclobutyl-(3-fluoro-phenyl)-methyl]-carbamoyl}-2-oxo-propyl)-6-iodo-benzoic acid Synthesis of compounds of the general formula XXIV and XXV: Compounds of general formula XXIV obtained analogously as described above for compounds of general formula XXIII but at higher temperature (150° C., 15 min) and they are usually hydrolyzed to compounds of the general formula XXV without isolation and characterization, so only two examples of compounds XXIV are given below.

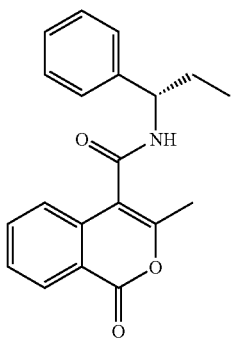

3-Methyl-1-oxo-1H-isochromene-4-carboxylic acid ((S)-1-phenyl-propyl)-amide

The title compound was purified by flash chromatography on $SiO_2$. LC-MS (m/z) 322.1 ($MH^+$); $t_R$=1.27. $^1H$ NMR (500 MHz, $CDCl_3$): 1.03 (t, J=7.3 Hz, 3H), 1.91-2.06 (complex m, 2H, $CH_2$), 2.19 (s, 3H), 5.11 (q, J=7.8 Hz, 1H), 7.06 (br. d, J=8.3 Hz, 1H, NH), 7.22-7.33 (m, 3H), 7.36-7.43 (m, 4H), 7.54 (t, J=7.6 Hz, 1H), 7.95 (d, J=7.8 Hz, 1H). $^1H$ NMR (500 MHz, DMSO-$d_6$): 0.92 (t, J=7.3 Hz, 3H), 1.76 (m, 2H), 2.18 (s, 3H), 4.93 (q, J=8.3 Hz, 1H), 7.21-7.41 (m, 6H), 7.59 (t, J=7.7 Hz, 1H), 7.82 (t, J=7.2 Hz, 1H), 8.17 (d, J=7.8 Hz, 1H), 9.1 (br. d, J=8.4 Hz, 1H, NH).

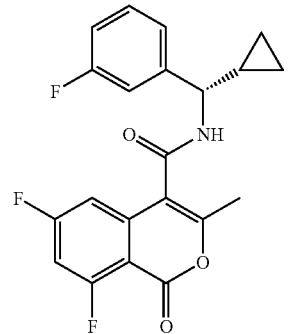

6,8-Difluoro-3-methyl-1-oxo-1H-isochromene-4-carboxylic acid [(S)-cyclopropyl-(3-fluoro-phenyl)-methyl]-amide The title compound was purified by flash chromatography on $SiO_2$. LC-MS (m/z) 388.4 ($MH^+$); $t_R$=1.39.

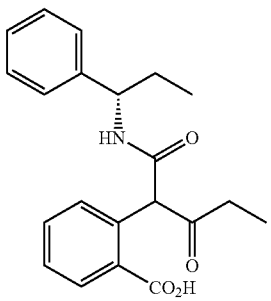

2-[2-Oxo-1-((S)-1-phenyl-propylcarbamoyl)-butyl]-benzoic acid

A sealed mixture of 2-[((S)-1-phenyl-propylcarbamoyl)-methyl]-benzoic acid (409 mg, 1.38 mmol), propionic anhydride (10 ml) and 4-N,N-dimethylaminopyridine (15 mg) was heated under microwave irradiation at 150° C. for 20 min and partitioned between 1M HCl (50 ml) and ethyl acetate (100 ml). The organic layer was washed with sat. aq. $NaHCO_3$ (2×50 ml) and brine and concentrated in vacuo. To the obtained residue methanol (25 ml) tetrahydrofurane (25 ml) and 2M aq. NaOH (50 ml) was added and stirred at r.t. for 1 hour. The organic volatiles were removed in vacuo and the pH was adjusted to 1 with 3M aq. HCl. The crude title product (495 mg) was separated by extraction with ethyl acetate (150 ml) and used in the next step without further purification. $^1$H NMR (500 MHz, DMSO-$d_6$): a mixture of tautomers and diastereoisomers.

The following compounds were obtained analogously:

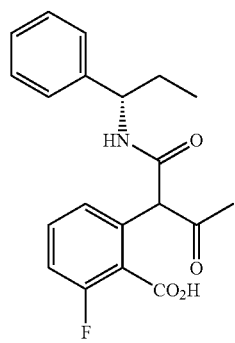

2-Fluoro-6-[2-oxo-1-((S)-1-phenyl-propylcarbamoyl)-propyl]-benzoic acid

LC-MS (m/z) 358.4 (MH$^+$); $t_R$=1.17.

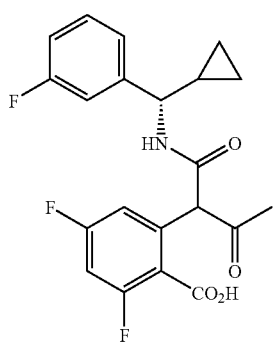

2-(1-{[(S)-Cyclopropyl-(3-fluoro-phenyl)-methyl]-carbamoyl}-2-oxo-propyl)-4,6-difluoro-benzoic acid LC-MS (m/z) 406.7 (MH$^+$); $t_R$=1.3.

Synthesis of compounds of the general formula XXXIII (scheme 7):

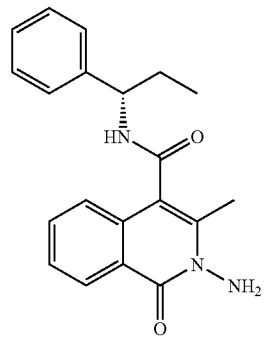

2-Amino-3-methyl-1-oxo-1,2-dihydro-isoquinoline-4-carboxylic acid ((S)-1 phenyl-propyl)-amide A solution of 4-acetyl-3-((S)-1-phenyl-propylamino)-2-benzopyran-1-one (4.330 g, 13.47 mmol) and tert-butyl carbazate (1.959 g, 14.82 mmol) in acetonitrile (20 mL) was heated under microwave irradiation at 140° C. for 30 min. LC-MS the formation of the intermediate [3-methyl-1-oxo-4-((S)-1-phenyl-propylcarbamoyl)-1H-isoquinolin-2-yl]-carbamic acid tert-butyl ester as a major component ($t_R$=1.36, UV 60%, ELSD 95%.). Then it was heated under microwave irradiation at 180° C. for total of 30 min (caution: $CO_2$ gas formation; the reaction mixture was cooled automatically three times then the excess $CO_2$ was released by puncture before heating continued to keep the pressure below the maximum limit of 20 bar). After cooling, the excess $CO_2$ was carefully removed by puncture with needle, then by gentle shaking, then with stirring, then under sonication (caution: very intensive gas evolution). White precipitate formed, which was filtered, washed with acetonitrile and water to give pure title compound (3.07 g; Yield=67.9%). LC-MS (m/z) 336.6 (MH$^+$); $t_R$=1.04. $^1$H NMR (250 MHz, 70° C., DMSO-$d_6$, DMSO-$d_5$=2.5 ppm): 0.96 (t, J=7.3 Hz, Me of Et), 1.7-1.96 (m, 2H, diastereotopic $CH_2$ of Et), 2.38 (s, 3H, Me), 5.0 (q (unres. dt), J (d)=6.8, J (t)=8.1, 1H, CH—NH), 5.82 (br. s, 2H, $NH_2$), 7.27 (tm, J (t)=6.7 Hz, J (m)=ca 1.5 Hz, 1H), 7.32-7.49 (m, 6H), 7.61 (t (unresolved tdd), J (t)=8.1 Hz, J (d)=1 Hz, J (d)<1 Hz, 1H), 8.25 (dd, J=8 Hz, J=0.8 Hz, 1H), 8.68 (br. d, J=8.1 Hz, 1H, NHCO).

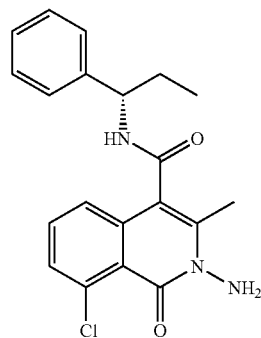

2-Amino-8-chloro-3-methyl-1-oxo-1,2-dihydro-iso-
quinoline-4-carboxylic acid ((S)-1-phenyl-propyl)-
amide LC-MS (m/z) 370.2 (MH⁺); $t_R$=1.2.

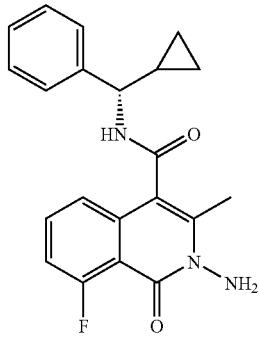

2-Amino-8-fluoro-3-methyl-1-oxo-1,2-dihydro-iso-
quinoline-4-carboxylic acid ((S)-cyclopropyl-phe-
nyl-methyl)-amide LC-MS (m/z) 366.5 (MH⁺); $t_R$=1.1.

2-Amino-1-oxo-3-(2-oxo-pyrrolidin-1-ylmethyl)-1,
2-dihydro-isoquinoline-4-carboxylic acid ((S)-1-
phenyl-propyl)-amide LC-MS (m/z) 419.7 (MH⁺); $t_R$=1.06.

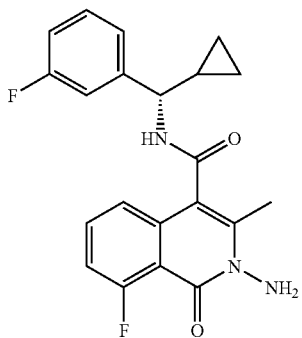

2-Amino-8-fluoro-3-methyl-1-oxo-1,2-dihydro-iso-
quinoline-4-carboxylic acid [(S)-cyclopropyl-(3-
fluoro-phenyl)-methyl]-amide LC-MS (m/z) 384.4 (MH⁺); $t_R$=1.15.

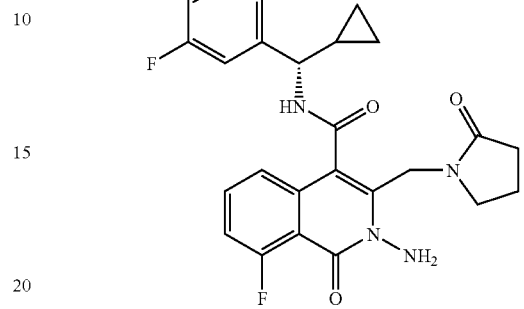

2-Amino-8-fluoro-1-oxo-3-(2-oxo-pyrrolidin-1-ylm-
ethyl)-1,2-dihydro-isoquinoline-4-carboxylic acid
[(S)-cyclopropyl-(3-fluoro-phenyl)-methyl]-amide LC-MS (m/z) 467.4 (MH⁺); $t_R$=1.12.

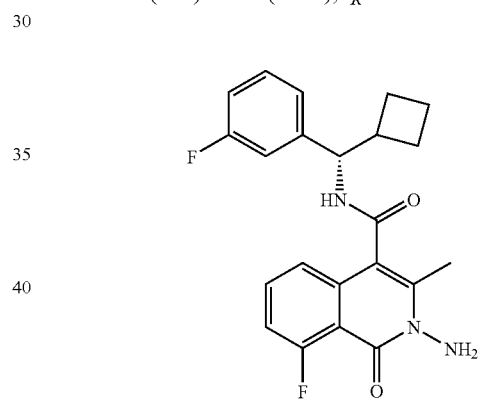

2-Amino-8-fluoro-3-methyl-1-oxo-1,2-dihydro-iso-
quinoline-4-carboxylic acid [(S)-cyclobutyl-(3-
fluoro-phenyl)-methyl]-amide A solution of 2-(1-{[(S)-cyclobutyl-(3-fluoro-phenyl)-me-thyl]-carbamoyl}-2-oxo-propyl)-6-fluoro-benzoic acid (2.148 g, 5.351 mmol) and tert-butyl carbazate (1.628 g, 12.32 mmol) in benzene (100 mL) was stirred under reflux for 20 hours. LC-MS indicated the formation of (4-{[(S)-Cy-clobutyl-(3-fluoro-phenyl)-methyl]-carbamoyl}-8-fluoro-3-methyl-1-oxo-1H-isoquinolin-2-yl)-carbamic acid tert-butyl ester ($t_R$=1.54, UV 39%, ELSD 80%, m/z 398.4 (major), 442.5, 498.7 (MH+)). The reaction mixture was rotovaped. The residue was dissolved in 1,2-dichloroethane (15 ml) and TFA (15 ml) was added. After 60 min it was evaporated, partitioned between sat. aq. NaHCO₃ and ethyl acetate, evaporated to give a crude residue of the title compound (1.7 g) that was used in the next step without purification. LC-MS (m/z) 398.0 (MH⁺), $t_R$=1.24.

The following compound was prepared analogously:

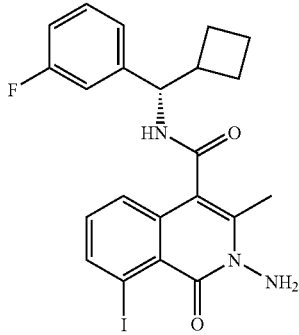

2-Amino-8-iodo-3-methyl-1-oxo-1,2-dihydro-isoquinoline-4-carboxylic acid [(S)-cyclobutyl-(3-fluoro-phenyl)-methyl]-amide

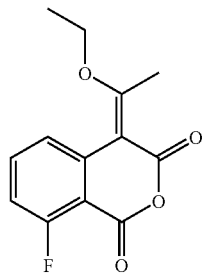

4-[1-Ethoxy-eth-(E)-ylidene]-8-fluoro-isochroman-1,3-dione

A suspension of 8-fluoro-isochroman-1,3-dione (7.125 g, 39.55 mmol) and triethyl orthoacetate (50.0 mL, 273 mmol) was heated to a gentle reflux during 5 min and reflux continued for 10 min. It was allowed to cool to r.t. with formation of crystalline product. It was cooled further on dry ice-EtOH bath, filtered, washed with cold ethanol (3×15 ml) and dried in vacuo (50° C., 30 min) to give 4.600 g of the title compound as a pink solid. The supernatant was evaporated and the purple oil residue was quenched with ethanol (20 ml) with formation of crystalline product, separated by filtration to give 693 mg more of the title product, total yield 53.5%. LC-MS (m/z) 251.2 (MH$^+$), $t_R$=1.05. $^1$H NMR (500 MHz, DMSO-d$_6$): 1.41 (t, J=7.0 Hz, 3H, Me of Et), 2.68 (s, 3H, Me), 4.46 (q, J=7.0 Hz, 2H, CH$_2$ of Et), 7.21 (dd, J=8.5 Hz, 10.7 Hz, 1H, C(7)-H), 7.72 (dt, J (d)=5.9 Hz, J (t)=8.3 Hz, 1H, C (6)-H), 8.08 (d, J=8.3 Hz, 1H, C (5)-H). $^{19}$F NMR (470.59 MHz): −110.2 ppm (dd, J=5.9 Hz, 10.7 Hz). $^{13}$C APT (125.76 MHz, DMSO-d$_6$=39.89 ppm): 14.8 (CH$_3$ of Et), 17.97 (CH$_3$), 66.79 (CH$_2$), 99.71 (C4), 109.04 (d, J=7.9 Hz, C9), 114.04 (d, J=20.6 Hz, CH, C7), 123.43 (d, J=3.3 Hz, CH, C5), 136.28 (d, J=10.5 Hz, CH, C6), 137.43 (s, C3=O), 157.22 (d, J=4.3 Hz, C1=O), 161.77 (C), 162.19 (d, J=262 Hz, C8), 178.45 (=C—OEt).

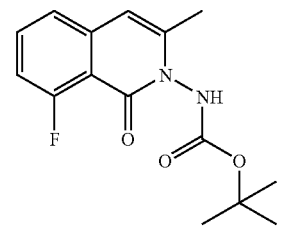

(8-Fluoro-3-methyl-1-oxo-1H-isoquinolin-2-yl)-carbamic acid tert-butyl ester

A suspension of 4-[1-Ethoxy-eth-(E)-ylidene]-8-fluoro-2-benzopyran-1,3-dione (5.25 g, 21.0 mmol), tert-butyl carbazate (3.43 g, 26.0 mmol) in ethanol (25.0 mL, 428 mmol) was heated under reflux for 30 min with intensive gas formation. The obtained clear purple solution was allowed to cool to r.t. with formation of white precipitate, cooled on dry ice—ethanol bath, filtered, washed with cold ethanol (3×10 ml) to give 3.436 g of the pure title product. Supernatant was quenched with water (200 ml), sat. aq. NaHCO$_3$ (50 ml) and diisopropyl ether (ca 20 ml), shaked, then quenched with heptane (100 ml) and sonicated. White precipitated was separated from this bilayer system by filtration to give 470 mg more of the title product; total yield 63.7%. LC-MS (m/z) 293.0 (traces, MH+), fragments: 237.3, 193.2 (major, M-Boc), 176.3. $^1$H NMR (500 MHz, DMSO-d$_6$), 88:12 mixture of rotamers A and B: 1.29 (s, 1.1H, tBu of B), 1.47 (s, 7.9H, tBu of A), 2.21 (s, 2.6H, Me of A), 2.21 (s, 0.4H, Me of B), 6.52 (s, 1H, C4-H), 7.17 (dd, J=8.3 Hz, J (H—F)=11.6 Hz, 1H, C7-H), 7.36 (d, J=7.9 Hz, 1H, C5-H), 7.68 (dt, J=7.8 Hz, J (H—F)=4.9 Hz, 1H, C6-H), 9.33 (s, 0.12H, NH of B), 9.8 (s, 0.88H, NH of A). $^{13}$C APT NMR (125.76 MHz, dmso-d6=39.89 ppm): 18.96 (Me), 27.99 (tBu of B), 28.31 (tBu of A), 80.98 (C of tBu), 103.59 (C4-H), 112.81 (d, J=20.9 Hz, C7-H), 113.25 (d, J=5 Hz, C9), 122.03 (d, J=3.5 Hz, C5-H), 134.62 (d, J=9.9 Hz, C6-H), 139.64 (C10), 143.96 (C3), 155.39 (NHCO$_2$), 157.88 (d, J=4.5 Hz, C1=O), 161.77 (d, J=262 Hz, C8-F). $^{19}$F NMR (470.59 MHz): −111.47 (unres. dd, J=11 Hz, J<4 Hz, rotamer A), −111.35 (unres. dd, J=10.5 Hz, rotamer B). VT $^1$H NMR (T=353 K, 250 MHz): all doubled signals corresponding to rotamers A and B have coalesced.

The following compound was obtained analogously:

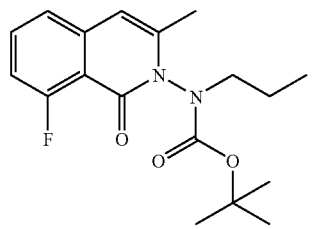

(8-Fluoro-3-methyl-1-oxo-1H-isoquinolin-2-yl)-propyl-carbamic acid tert-butyl ester (4-Bromo-8-fluoro-3-methyl-1-oxo-1H-isoquinolin-2-yl)-propyl-carbamic acid tert-butyl ester

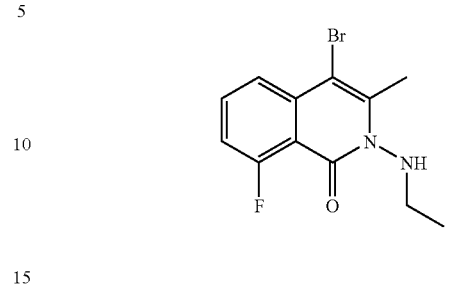

4-Bromo-2-ethylamino-8-fluoro-3-methyl-2H-isoquinolin-1-one

A solution of (4-bromo-8-fluoro-3-methyl-1-oxo-1H-isoquinolin-2-yl)-carbamic acid tert-butyl ester (100.0 mg, 0.2694 mmol) in trifluoroacetic acid (1 mL) was stirred at r.t. for 40 min and evaporated. LC-MS 07-07-2008 12-11-51.wiff:ca 2:1 mixture of the desired intermediate 2-amino-4-bromo-8-fluoro-3-methyl-2H-isoquinolin-1-one [B] ($t_R$=1.01, m/z MH$^+$271.3 & 273.3) and presumably its trifluoroacetyl derivative ($t_R$=1.19, m/z MH$^+$ 367.2 & 369.2). Alternatively, deprotection of BOC group was successfully carried out in conc. HCl solution in methanol under reflux (5 min). It was mixed with 2 ml methanol, 0.3 ml 20% KOH in water, refluxed for 5 min, allowed to cool and quenched with water (3 ml). The precipitate was filtered to 46.2 mg of pale yellow solid as 4:1 mixture of the above compounds. It was suspended in MeOH (3 ml), acetaldehyde (0.20 mL, 3.6 mmol) was added, followed by sodium cyanoborohydride (100.0 mg, 1.591 mmol) and acetic acid (0.4 mL, 7 mmol). It was stirred for 90 min and diluted with 5% aq. KOH (10 ml), allowed to stir for 20 min and filtered to give 20 mg of the title product. LC-MS (m/z) 299.4 & 301.4 (MH$^{3O}$), $t_R$=1.42. $^1$H NMR (CDCl$_3$, TMS=0 ppm): 1.21 (t, J=7.2 Hz, 3H, Et), 2.77 (overlapping s, 3H, Me), 2.68-3.2 (overlapping very br. d, 2H, Et), 5.89 (t, J=6.8 Hz, 1H, NH), 7.13 (dd, J=8.3, J (HF)=10.9, 1H, C7H), 7.63 (dt, J (d, H—F)=5.05 Hz, J (t)=8.1 Hz, 1H, C6H), 7.74 (d, J=8.3 Hz, 1H, C5H). $^{13}$C APT (CDCl$_3$=77.44 ppm): 13.0 (Me of Et), 19.95 (Me), 46.26 (CH$_2$), 99.72 (d, J C—F)=3.5 Hz, C), 113.78 (d, J (C—F)=21.7 Hz, C7H), 122.24 (d, J (C—F)=4.1 Hz, C5H), 134.03 (d, J (C—F)=10.2 Hz, C6H), 138.02 (C), 142.16 (C3), 158.7 (d, J (C—F)=4.6 Hz, C), 162.56 (d, J (C—F)=264 Hz, C8F). $^{19}$F NMR (CFCl$_3$=0 ppm): −110.92 (dd, J=4.5 Hz, J=10.9 Hz).

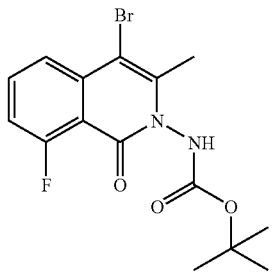

(4-Bromo-8-fluoro-3-methyl-1-oxo-1H-isoquinolin-2-yl)-carbamic acid tert-butyl ester A solution of (8-fluoro-3-methyl-1-oxo-1H-isoquinolin-2-yl)-carbamic acid tert-butyl ester (501.9 mg, 1.717 mmol) and N-bromosuccinimide (366.0 mg, 2.056 mmol) in N,N-dimethylformamide (5 mL) was stirred at r.t. for 60 min. It was poured into 50 ml ether, washed with 5% aq. NaHCO$_3$ two times, then with water 3 times, white precipitate formed, which was filtered and washed with ether to give 118 mg of the pure title product. Supernatant gave 490 mg more of the title product as a colourless solid; total yield 95.4%. LC-MS (m/z) 271.5 and 273.3 (major fragment, M-Boc), $t_R$=1.39. $^1$H NMR (500 MHz, CDCl$_3$) 1.51 (br. s, 9H, tBu), 2.64 (s, 3H, Me), 7.11 (dd, J=8.2 Hz, J=10.6 Hz, 1H, C7H), 3.67 (br. s, 1H, NH), 7.63 (dt, J (d)=4.95 Hz, J (t)=8.1 Hz, 1H, C6H), 7.68 (d, J=8.1 Hz, 1H, C5H). $^{19}$F NMR (470.59 MHz, CFCl3=0 ppm), 4:96 mixture of rotamers, −108.9 (br. s, 0.04F), −109.98 (br. s, 0.96F). $^{13}$C APT NMR (CDCl3=77.43 ppm): 20.15 (Me), 28.47 (tBu), 83.47 (C of tBu), 113.44 (C), 114.24 (d, J=21.4 Hz, C7H), 122.57 (d, J=4 Hz, C5H), 134.68 (d, J=10.3 Hz, C6H), 138.31 (s, C), 142.69 (s, C), 155.91 (C), 158.42 (C), 161.63 (s, C), 163.74 (s, C).

The following compound was obtained analogously:

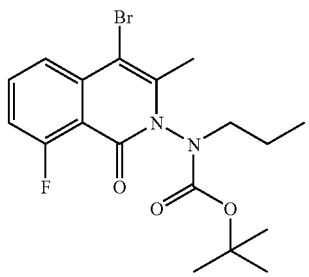

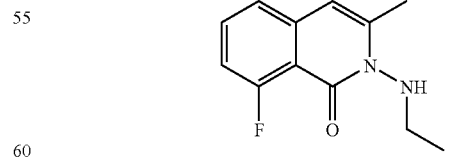

2-Ethylamino-8-fluoro-3-methyl-1-oxo-1,2-dihydro-isoquinoline-4-carboxylic acid

A stirred suspension of 4-bromo-2-ethylamino-8-fluoro-3-methyl-2H-isoquinolin-1-one (1.526 g, 4.847 mmol), palladium acetate (108.8 mg, 0.4847 mmol), 4,5-bis-diphenylphosphanyl-9,9-dimethyl-9H-xanthene (=Xantphos, 280.5 mg, 0.4847 mmol) and sodium carbonate (1.541 g, 14.54 mmol) in toluene (10 mL) was filled with carbon monoxide to 5 bars (6 times). It was stirred on hot oil bath (122° C., P=6 bar) for 19 hours, allowed to cool and the excess CO was released. It was quenched with 20 ml EtOH, filtered and partitioned between 3:1 Ether-EtOAc (3×100 ml) and 5% aq. NaHCO$_3$ (100 ml). Each organic layer was washed with 2×5 ml 5% aq. NaHCO$_3$. The organic solution contained crude unreacted starting material (865 mg). The combined aq. solution was acidified with 3M aq. HCl (pH=0) at 0° C., extracted with ethyl acetate (4×50 ml), each organic layer was washed with sat. aq. NaCl (2×5 ml). The combined org. solution was dried (Na$_2$SO$_4$) and rotovaped to give the pure title compound (190 mg; yield=15%) as a dark solid. LC-MS (m/z) 265.2 (MH$^+$), fragments: 221.4 (M—CO$_2$), 178.7 (M—CO$_2$-EtNH); t$_R$0.74. $^1$H NMR (500 MHz, DMSO-d$_6$): 1.09 (t, J=7.2 Hz, 3H, Me of Et), 2.51 (s, 3H, Me (overlapped with dmso-d5)), 2.9 (br., 2H, CH$_2$ of Et), 3.4 (very br., H$_2$O+ CO$_2$H), 6.18 (br., 1H, NH), 7.25 (dd, J=8.0 Hz, J (H—F)= 11.7 Hz, 1H, C7H), 7.44 (d, J=8.2 Hz, C5H), 7.74 (dt, J (d, H—F)=5.1 Hz, J (t)=8.2 Hz, 1H, C6H). $^{19}$F NMR (470 MHz, CFCl$_3$=0 ppm): −110.78 (dd, J=4.9 Hz, J=11.5 Hz). $^{13}$C APT (125 MHz, DMSO-d$_5$=39.87 ppm): 12.89 (Me of Et), 17.18 (Me), 44.69 (CH$_2$ of Et), 110.46 (s, C), 112.76 (d, J=5.8 Hz, C), 113.18 (d, J=21 Hz, C7H), 120.01 (d, J=3.6 Hz, C5H), 134.44 (d, J=9.9 Hz, C6H), 135.94 (C), 143.13 (C), 157.79 (d, J=4.8 Hz, C), 161.64 (d, J=262 Hz, C8-F), 168.57 (C).

The following compounds were obtained analogously:

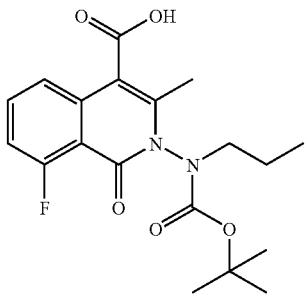

2-(tert-Butoxycarbonyl-propyl-amino)-8-fluoro-3-methyl-1-oxo-1,2-dihydro-isoquinoline-4-carboxylic acid

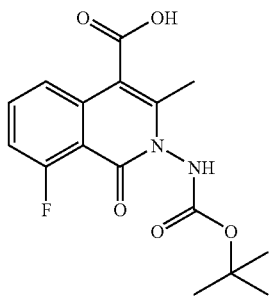

2-tert-Butoxycarbonylamino-8-fluoro-3-methyl-1-oxo-1,2-dihydro-isoquinoline-4-carboxylic acid

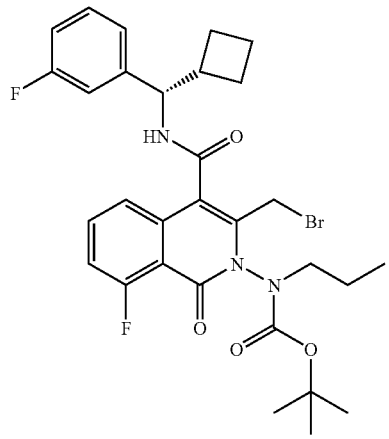

(3-Bromomethyl-4-{[(S)-cyclobutyl-(3-fluoro-phenyl)-methyl]-carbamoyl}-8-fluoro-1-oxo-1H-isoquinolin-2-yl)-propyl-carbamic acid tert-butyl ester (4-{[(S)-Cyclobutyl-(3-fluoro-phenyl)-methyl]carbamoyl}-8-fluoro-3-methyl-1-oxo-1H-isoquinolin-2-yl)-propyl-carbamicacid tert-butyl ester (0.2 g, 0.4 mmol; prepared as described in example 8), carbon tetrachloride (50 mL), N-bromosuccinimide (0.072 g, 0.41 mmol) and benzoyl peroxide (10 mg, 0.04 mmol) are warmed at 80° C. for 2 hours. The reaction mixture was cooled and washed with 10 ml of water. The organic phase was dried over MgSO4 and was rotovaped to give 0.3 g. crude product. The product was chromatographed on silica gel with Etac:Hept, 30:70 as eluent to give 0.15 g. the title compound as an oil.

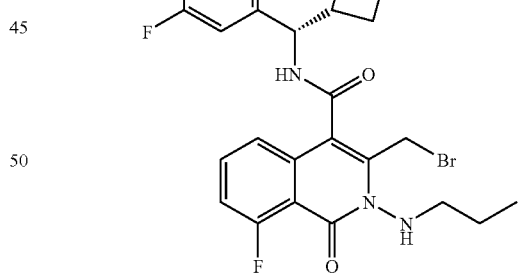

3-Bromomethyl-8-fluoro-1-oxo-2-propylamino-1,2-dihydro-isoquinoline-4-carboxylic acid [(S)-cyclobutyl-(3-fluoro-phenyl)-methyl]-amide 0.15 mg (3-Bromomethyl-4-{[(S)-cyclobutyl-(3-fluoro-phenyl)-methyl]-carbamoyl}-8-fluoro-1-oxo-1H-isoquinolin-2-yl)-propyl-carbamic acid tert-butyl ester was stirred at room temperature over night in 2 mL 1,2-dichloroethane and 2 mL trifluoroacetic acid. The reaction mixture was concentrated in vacuo to give the title compound.

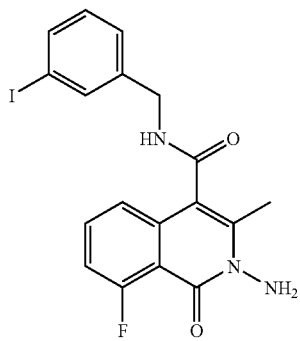

2-Amino-8-fluoro-3-methyl-1-oxo-1,2-dihydro-isoquinoline-4-carboxylic acid 3-iodo-benzylamide

[8-Fluoro-4-(3-iodo-benzylcarbamoyl)-3-methyl-1-oxo-1H-isoquinolin-2-yl]-carbamic acid tert-butyl ester in acetonitrile (prepared as described in example 8) was heated to remove the tert-butoxy carbonyl group as described in the synthesis of 2-amino-3-methyl-1-oxo-1,2-dihydro-isoquinoline-4-carboxylic acid ((S)-1-phenyl-propyl)-amide to give the title compound.

Compounds of the Invention

Example 1

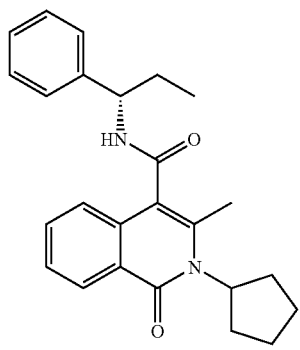

1a 2-Cyclopentyl-3-methyl-1-oxo-1,2-dihydro-isoquinoline-4-carboxylic acid ((S)-1-phenyl-propyl)-amide A mixture of 4-acetyl-3-((S)-1-phenyl-propylamino)-isochromen-1-one (60 mg) and cyclopentylamine (0.06 mL) in acetonitrile (0.2 mL) was heated under microwave irradiation at 170° C. for 15 min. The reaction mixture was partitioned between 2M HCl (3 mL) and ethyl acetate (3 mL). The organic phase was absorbed on $SiO_2$ and flash chromatographed (20 g $SiO_2$ column, gradient heptane-ethyl acetate, the product came out with 40% ethyl acetate) to give 18 mg of the title compound as a colourless solid. LC-MS (m/z) 389.5 (MH$^+$); $t_R$=1.52.

The following compounds were obtained analogously from corresponding ketene-aminals of the general formula XXIII and appropriate amino compound of the general formula VI:

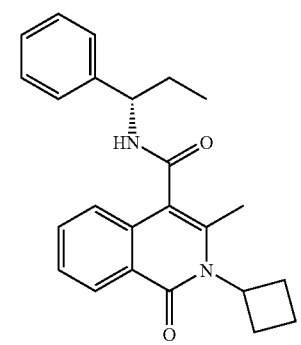

1b 2-Cyclopropyl-3-methyl-1-oxo-1,2-dihydro-isoquinoline-4-carboxylic acid ((S)-1-phenyl-propyl)-amide LC-MS (m/z) 361.5 (MH$^+$); $t_R$=1.25. $^1$H NMR (250 MHz, 70° C., DMSO-$d_6$): 0.8 (m, 2H, Cp), 0.95 (t, J=7.3 Hz, 3H, Me of Et), 1.19 (m, 2H, Cp), 2.41 (s, 3H, Me), 2.95 (m, 1H, Cp), 4.98 (q (unresolved dt), J (d)=6.8 Hz, J (t)=8.2 Hz, 1H, CH—NH), 7.21-7.45 (m, 7H), 7.58 (dt, J (d)=1.3 Hz, J (t)=7.7 Hz, 1H), 8.18 (dd, J=1.2 Hz, J=8.1 Hz, 1H), 8.62 (br. D, J=7.9 Hz, NH).

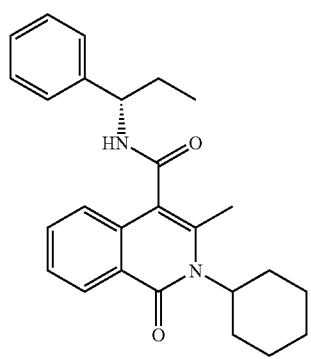

1c 2-Cyclobutyl-3-methyl-1-oxo-1,2-dihydro-isoquinoline-4-carboxylic acid ((S)-1-phenyl-propyl)-amide LC-MS (m/z) 375.3 (MH$^+$); $t_R$=1.43.

1d 2-Cyclohexyl-3-methyl-1-oxo-1,2-dihydro-isoquinoline-4-carboxylic acid ((S)-1-phenyl-propyl)-amide LC-MS (m/z) 403.1 (MH$^+$); $t_R$=1.6.

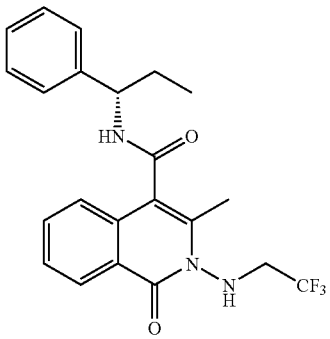

1e 3-Methyl-1-oxo-2-(2,2,2-trifluoro-ethylamino)-1,2-dihydro-isoquinoline-4-carboxylic acid ((S)-1-phenyl-propyl)-amide LC-MS (m/z) 418.8 (MH$^+$); $t_R$=1.45. $^1$H NMR (250 MHz, 70° C., DMSO-d$_6$): 0.95 (t, J=7.3 Hz, 3H, Me of Et), 1.72-1.91 (complex m, 2H, CH$_2$ of Et), 2.34 (s, 3H, Me), 3.81 (dq, J(H—F)=10.1 Hz, J=6.0 Hz, NHCH$_2$CF$_3$), 4.97 (q (unres dt), J (t)=8.2 Hz, J (d)=6.9 Hz, CHNH), 6.74 (t, J=5.9 Hz, 1H, NNH), 7.22-7.43 (m, 6H), 7.47 (t, J=7.6 Hz, 1H), 7.65 (t, J=7.6 Hz, 1H), 8.25 (d, J=7.8 Hz, 1H), 8.68 (br. d, J=8.5 Hz, 1H, NHCO).

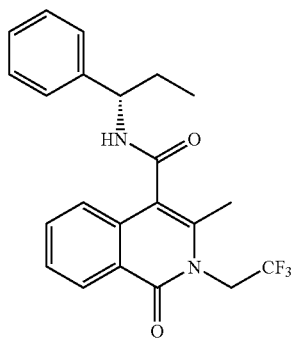

1f 3-Methyl-1-oxo-2-(2,2,2-trifluoro-ethyl)-1,2-dihydro-isoquinoline-4-carboxylic acid ((S)-1-phenyl-propyl)-amide LC-MS (m/z) 403.1 (MH$^+$); $t_R$=1.41.

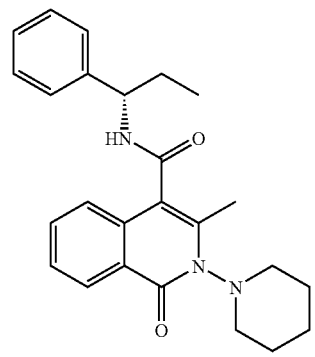

1g 3-Methyl-1-oxo-2-piperidin-1-yl-1,2-dihydro-isoquinoline-4-carboxylic acid ((S)-1-phenyl-propyl)-amide LC-MS (m/z) 404.5 (MH$^+$); $t_R$=1.63.

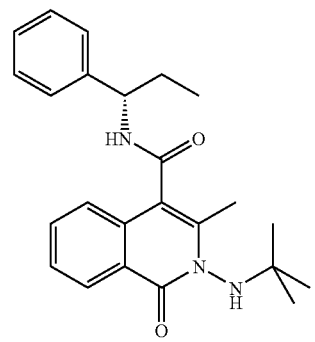

1 h 2-tert-Butylamino-3-methyl-1-oxo-1,2-dihydro-isoquinoline-4-carboxylic acid ((S)-1 phenyl-propyl)-amide The solution of tert-butylhydrazine for the reaction was obtained by shaking of tert-butylhydrazine hydrochloride with suspension of anhydrous Na$_2$CO$_3$ in acetonitrile at 50° C. followed by filtration. The reaction was run at 140° C. (15 min). LC-MS (m/z) 392.8 (MH$^+$); $t_R$=1.55.

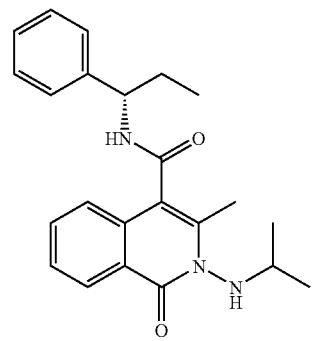

1i 2-Isopropylamino-3-methyl-1-oxo-1,2-dihydro-isoquinoline-4-carboxylic acid ((S)-1-phenyl-propyl)-amide Three regioisomers were observed in the reaction mixture with similar $t_R$ values (0.75, 0.76, and 0.77, HPLC method B; same Rf values by TLC), including the title product and two regioisomeric benzodiazepines. They were separated by flash chromatography (400 mg of reaction mixture on 70 g $SiO_2$ column, gradient heptane—ethyl acetate, products came out with 30-40% ethyl acetate) each fraction was analysed by LC-MS and only pure fractions were evaporated. LC-MS (m/z) 378.3 (MH$^+$); $t_R$=0.77 (method B); 1.46 (method A). $^1$H NMR (250 MHz, 70° C., DMSO-$d_6$): 0.96 (t, J=7.6 Hz, 3H, Me of Et), 1.05 (d, J=6.3 Hz, 6H, iPr), 1.72-1.93 (complex m, 2H, CH$_2$ of Et), 2.36 (s, 3H, Me), 3.42 (m, 1H, CH of iPr), 4.98 (q (unres dt), CHNH), 5.91 (d, J=5.1 Hz, 1H, NNH), 7.22-7.49 (m, 7H), 7.63 (t, 1H), 8.24 (d, J=8 Hz, 1H), 8.68 (br. d, J=7.9 Hz, 1H, NHCO).

1k 3-Methyl-1-oxo-2-propyl-1,2-dihydro-isoquinoline-4-carboxylic acid ((S)-1-phenyl-propyl)-amide LC-MS (m/z) 363.7 (MH$^+$); $t_R$=1.37.

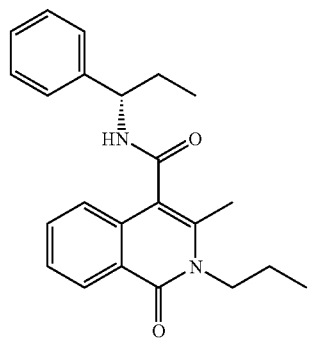

1l 2-Butyl-3-methyl-1-oxo-1,2-dihydro-isoquinoline-4-carboxylic acid ((S)-1 phenyl-propyl)-amide LC-MS (m/z) 377.6 (MH$^+$); $t_R$=1.48.

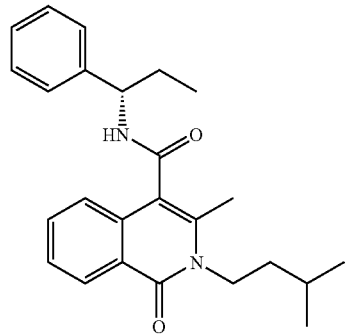

1m 3-Methyl-2-(3-methyl-butyl)-1-oxo-1,2-dihydro-isoquinoline-4-carboxylic acid ((S)-1 phenyl-propyl)-amide LC-MS (m/z) 391.8 (MH$^+$); $t_R$=1.58.

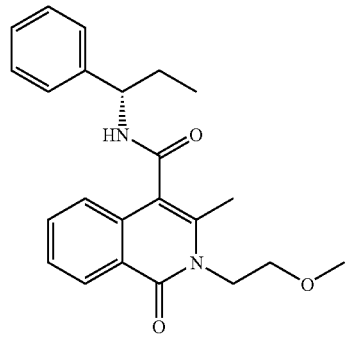

1n 2-(2-Methoxy-ethyl)-3-methyl-1-oxo-1,2-dihydro-isoquinoline-4-carboxylic acid ((S)-1-phenyl-propyl)-amide LC-MS (m/z) 379.6 (MH$^+$); $t_R$=1.25.

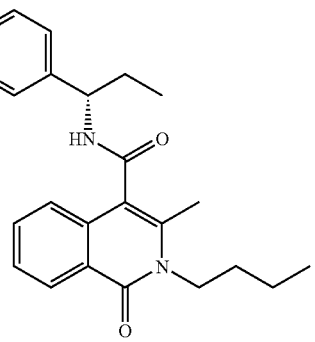
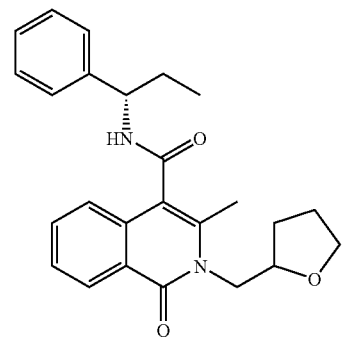

1o 3-Methyl-1-oxo-2-(tetrahydro-furan-2-ylmethyl)-1,2-dihydro-isoquinoline-4-carboxylic acid ((S)-1-phenyl-propyl)-amide LC-MS (m/z) 405.5 (MH$^+$); $t_R$=1.31.

1r 2-Butyl-3-methyl-1-oxo-1,2-dihydro-isoquinoline-4-carboxylic acid ((S)-1-phenyl-propyl)-amide Ethoxyamine hydrochloride was used in the condensation in the presence of diisopropylethylamine (1 eq.) at 150° C. for 15 min. LC-MS (m/z) 365.7 (WO; $t_R$=1.29.

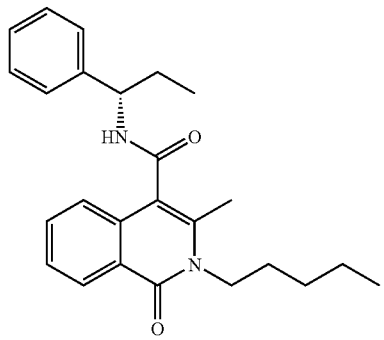

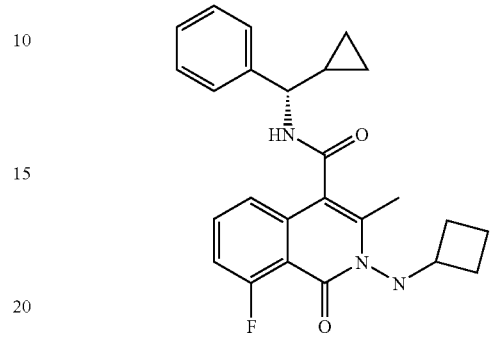

1p 3-Methyl-1-oxo-2-pentyl-1,2-dihydro-isoquinoline-4-carboxylic acid ((S)-1-phenyl-propyl)-amide LC-MS (m/z) 391.7 (MH$^+$); $t_R$=1.59.

1s 2-Cyclobutylamino-8-fluoro-3-methyl-1-oxo-1,2-dihydro-isoquinoline-4-carboxylic acid ((S)-cyclopropyl-phenyl-methyl)-amide LC-MS (m/z) 420.6 (MH$^+$); $t_R$=1.50.

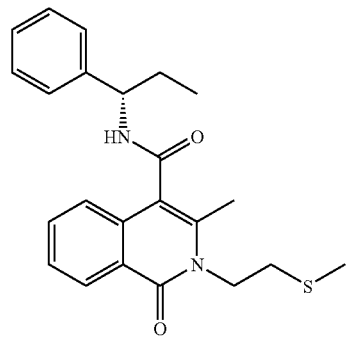

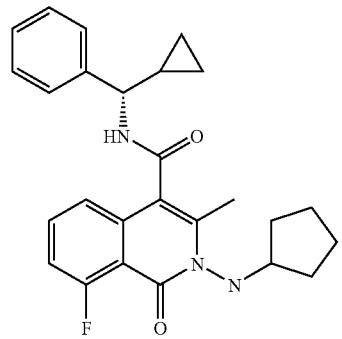

1q 3-Methyl-2-(2-methylsulfanyl-ethyl)-1-oxo-1,2-dihydro-isoquinoline-4-carboxylic acid ((S)-1-phenyl-propyl)-amide LC-MS (m/z) 395.0 (MH$^+$); $t_R$=1.37.

1t 2-Cyclopentylamino-8-fluoro-3-methyl-1-oxo-1,2-dihydro-isoquinoline-4-carboxylic acid ((S)-cyclopropyl-phenyl-methyl)-amide LC-MS (m/z) 434.4 (MH$^+$); $t_R$=1.59.

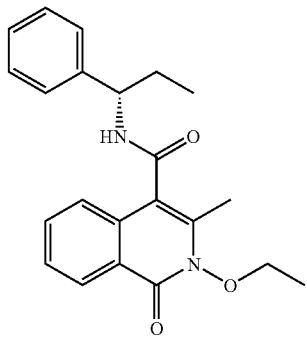

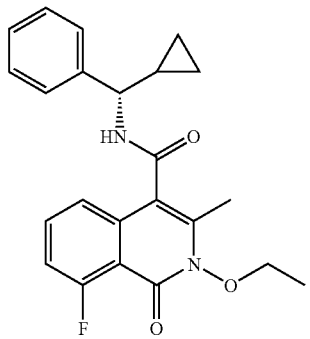

1u 2-Ethoxy-8-fluoro-3-methyl-1-oxo-1,2-dihydro-isoquinoline-4-carboxylic acid ((S)-cyclopropyl-phenyl-methyl)-amide LC-MS (m/z) 395.4 (MH$^+$); $t_R$=1.29.

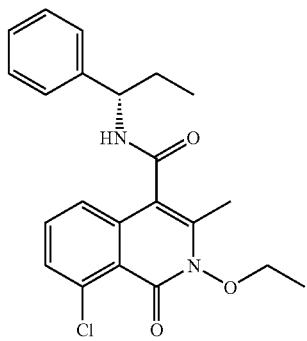

1v 8-Chloro-2-ethoxy-3-methyl-1-oxo-1,2-dihydro-isoquinoline-4-carboxylic acid ((S)-1-phenyl-propyl)-amide Ethoxyamine hydrochloride was used in the condensation in the presence of diisopropylethylamine (1 eq.) at 170° C. for 10 min. LC-MS (m/z) 399.3 (MH$^+$); $t_R$=1.39.

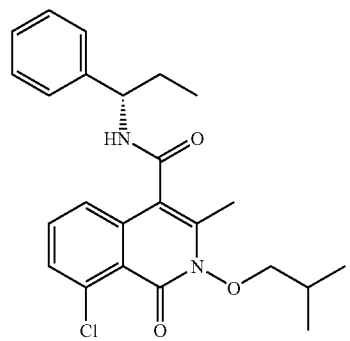

1w 8-Chloro-2-isobutoxy-3-methyl-1-oxo-1,2-dihydro-isoquinoline-4-carboxylic acid ((S)-1-phenyl-propyl)-amide O-iso-Butylhydroxylamine hydrochloride was used in the condensation in the presence of diisopropylethylamine (1 eq.) at 170° C. for 10 min. LC-MS (m/z) 427.1 (MH$^+$); $t_R$=1.61.

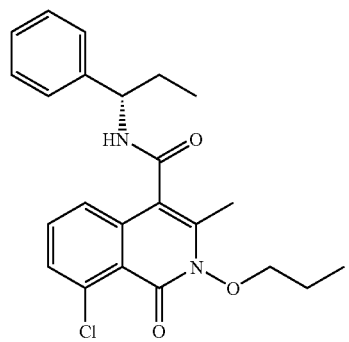

1x 8-Chloro-3-methyl-1-oxo-2-propoxy-1,2-dihydro-isoquinoline-4-carboxylic acid ((S)-1-phenyl-propyl)-amide 1-(Aminooxy)propane hydrochloride was used in the condensation in the presence of diisopropylethylamine (1 eq.) at 170° C. for 10 min. LC-MS (m/z) 413.1 (MH$^+$; $t_R$=1.5

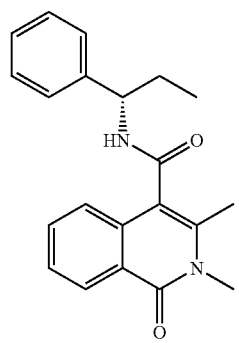

1y 2,3-Dimethyl-1-oxo-1,2-dihydro-isoquinoline-4-carboxylic acid ((S)-1 phenyl-propyl)-amide LC-MS (m/z) 335.4 (MH$^+$); $t_R$=1.16.

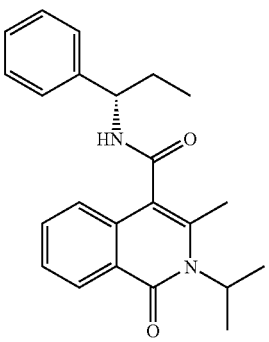

1z 2-Isopropyl-3-methyl-1-oxo-1,2-dihydro-isoquinoline-4-carboxylic acid ((S)-1-phenyl-propyl)-amide LC-MS (m/z) 363.5 (MH$^+$); $t_R$=1.37.

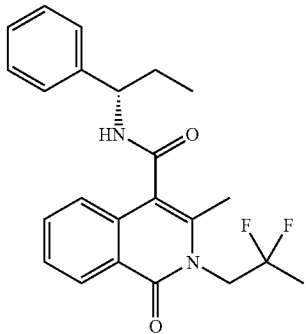

1aa 2-(2,2-Difluoro-propyl)-3-methyl-1-oxo-1,2-dihydro-isoquinoline-4-carboxylic acid ((S)-1-phenyl-propyl)-amide LC-MS (m/z) 399.3 (MH$^+$); $t_R$=1.38.

Example 2

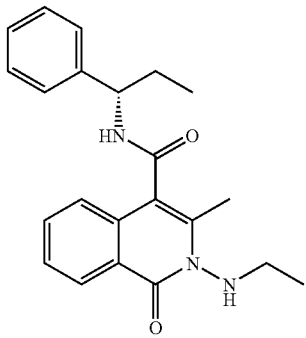

2a 2-Ethylamino-3-methyl-1-oxo-1,2-dihydro-isoquinoline-4-carboxylic acid ((S)-1-phenyl-propyl)-amide To a mixture of 2-amino-3-methyl-1-oxo-1,2-dihydro-isoquinoline-4-carboxylic acid ((S)-1-phenyl-propyl)-amide (3.04 g, 9.06 mmol) and sodium cyanoborohydride (1.00 g, 15.9 mmol) in methanol (25 mL), acetaldehyde (2.00 mL, 35.6 mmol) was added followed by dropwise addition of acetic acid (2.5 mL, 44 mmol) (caution: exothermic reaction with gas evolution). The obtained clear colorless solution was stirred at r.t. for 30 min. More sodium cyanoborohydride (1 g), acetaldehyde (1 ml), and acetic acid (2 ml) were added and stirring continued for 2 hour. LC-MS indicated a full conversion to the title product with formation of traces of the double alkylation product (UV 1.3%, $t_R$=1.5, m/z (MH$^+$) 392.4). The reaction mixture was partitioned between 5% aq. NaHCO$_3$ (100 ml, pH=7) and ethyl acetate (3×50 mL), the combined organic solutions were washed with water 3 times, and evaporated to give 3.2 g of colorless solid residue. The crude product was transferred into 100 g prepacked SiO$_2$ column with 1,2-dichloroethane and flash chromatographed with gradient 20% to 50% ethyl acetate in heptane. The title product came out with 40-50% ethyl acetate to give 2.73 g of colorless foam after evaporation and drying in high vacuo at 60° C. for 2 hours. LC-MS (m/z) 364.6 (MH$^+$); $t_R$=1.33. LC— high res. MS: calculated for C$_{22}$H$_{26}$N$_3$O$_2$ (MH$^+$) 364.2020. found 364.2006. $^1$H NMR (250 MHz, 70° C., DMSO-d$_6$, DMSO-d$_5$=2.5 ppm): 0.96 (t, J=7.3 Hz, 3H, Me of Et), 1.13 (t, J=7.3 Hz, 3H, Me of EtNH), 1.72-1.94 (m, 2H, CH$_2$ of Et), 2.38 (s, 3H, Me), 2.97 (quintet, J=7.1 Hz, 2H, CH$_2$ of EtNH), 5.0 (q (unres. dt), J=6.8 Hz, J=8.2 Hz, 1H, CHNHCO), 6.05 (t, J=6.6 Hz, 1H, NHEt), 7.27 (m, 1H), 7.31-7.5 (m, 5H), 7.62 (m, 1H), 8.26 (d, J=8 Hz, 1H, C8-H), 8.68 (br. d, J=8.1 Hz, 1H). $^{13}$C APT (125 MHz, 25° C., DMSO-d$_6$=39.88 ppm): 11.65 (CH$_3$ of Et), 12.99 (CH$_3$ of NHEt), 16.55 (br, CH$_3$), 29.58 (CH$_2$ of Et), 44.99 (CH$_2$ of NHEt), 55.29 (CHNHCO), 114.3 (C), 123.73 (br, CH), 123.82 (C), 126.4 (CH), 126.93 (CH of Ph), 127.21 (CH), 127.47 (C8-H), 128.64 (CH of Ph), 132.89 (br, CH), 134.3 (C), 139.21 (C3), 143.92 (C1 of Ph), 160.82 (CON), 166.12 (CONH).

The following compounds were obtained analogously by reductive alkylation with corresponding aldehyde:

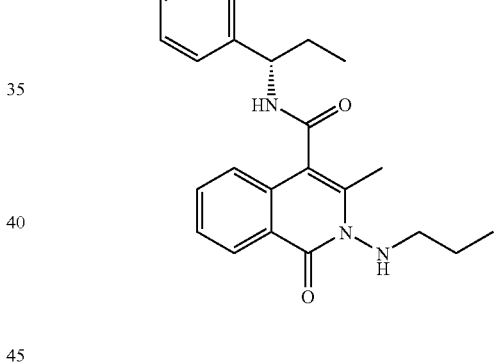

2b 3-Methyl-1-oxo-2-propylamino-1,2-dihydro-isoquinoline-4-carboxylic acid ((S)-1-phenyl-propyl)-amide LC-MS (m/z) 378.5 (MH$^+$); $t_R$=1.47.

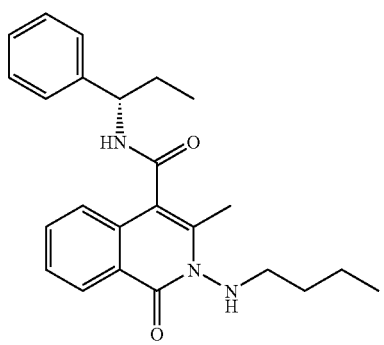

2c 2-Butylamino-3-methyl-1-oxo-1,2-dihydro-iso-quinoline-4-carboxylic acid ((S)-1-phenyl-propyl)-amide LC-MS (m/z) 392.8 (MH$^+$); $t_R$=1.59.

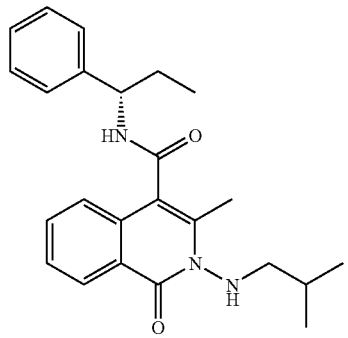

2d 2-Isobutylamino-3-methyl-1-oxo-1,2-dihydro-isoquinoline-4-carboxylic acid ((S)-1-phenyl-propyl)-amide LC-MS (m/z) 392.7 (MH$^+$); $t_R$=1.59.

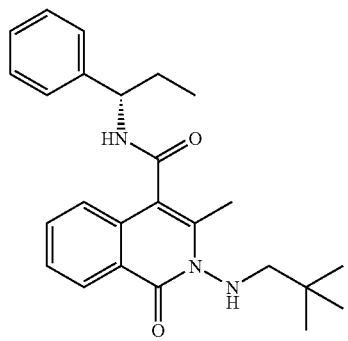

2e 2-(2,2-Dimethyl-propylamino)-3-methyl-1-oxo-1,2-dihydro-isoquinoline-4-carboxylic acid ((S)-1-phenyl-propyl)-amide LC-MS (m/z) 406.6 (MH$^+$); $t_R$=1.69.

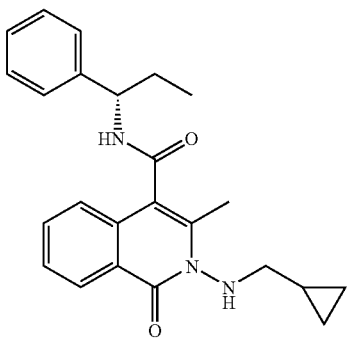

2f 2-(Cyclopropylmethyl-amino)-3-methyl-1-oxo-1,2-dihydro-isoquinoline-4-carboxylic acid ((S)-1-phenyl-propyl)-amide LC-MS (m/z) 390.6 (MH$^+$); $t_R$=1.47.

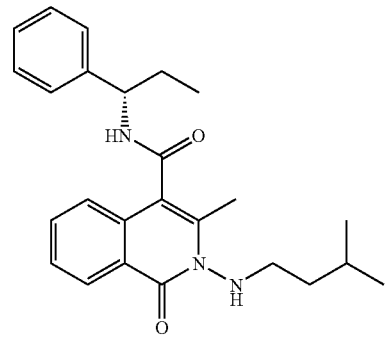

2g 2-(2,2-Dimethyl-propylamino)-3-methyl-1-oxo-1,2-dihydro-isoquinoline-4-carboxylic acid ((S)-1-phenyl-propyl)-amide LC-MS (m/z) 406.9 (MH$^+$); $t_R$=1.69.

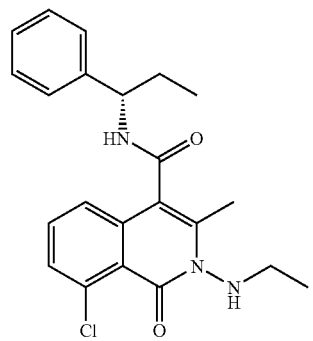

2h 8-Chloro-2-ethylamino-3-methyl-1-oxo-1,2-dihydro-isoquinoline-4-carboxylic acid ((S)-1-phenyl-propyl)-amide LC-MS (m/z) 398.0 (MH$^+$); $t_R$=1.46.

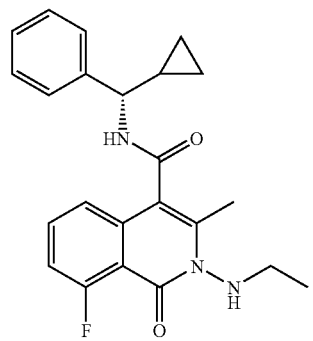

2i 2-Ethylamino-8-fluoro-3-methyl-1-oxo-1,2-dihy-
dro-isoquinoline-4-carboxylic acid ((S)-cyclopropyl-
phenyl-methyl)-amide LC-MS (m/z) 394.4 (MH$^+$); $t_R$=1.41.

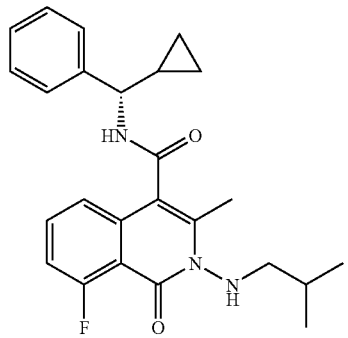

2j 8-Fluoro-2-isobutylamino-3-methyl-1-oxo-1,2-
dihydro-isoquinoline-4-carboxylic acid ((S)-cyclo-
propyl-phenyl-methyl)-amide LC-MS (m/z) 422.4 (MH$^+$); $t_R$=1.59.

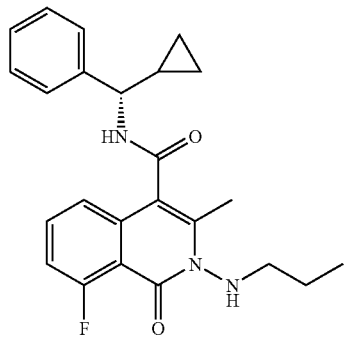

2k 8-Fluoro-3-methyl-1-oxo-2-propylamino-1,2-
dihydro-isoquinoline-4-carboxylic acid ((S)-cyclo-
propyl-phenyl-methyl)-amide LC-MS (m/z) 408.6 (MH$^+$); $t_R$=1.52.

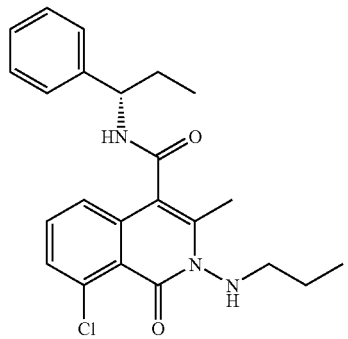

2l 8-Chloro-3-methyl-1-oxo-2-propylamino-1,2-
dihydro-isoquinoline-4-carboxylic acid ((S)-1-phe-
nyl-propyl)-amide LC-MS (m/z) 412.3 (MH$^+$); $t_R$=1.58.

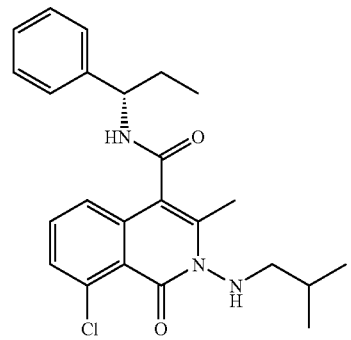

2m 8-Chloro-2-isobutylamino-3-methyl-1-oxo-1,2-
dihydro-isoquinoline-4-carboxylic acid ((S)-1-phe-
nyl-propyl)-amide LC-MS (m/z) 426.3 (MH$^+$); $t_R$=1.69.

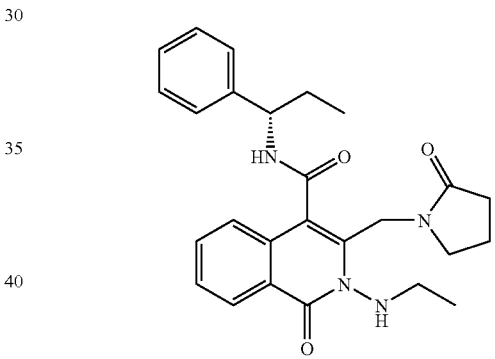

2n 2-Ethylamino-1-oxo-3-(2-oxo-pyrrolidin-1-ylm-
ethyl)-1,2-dihydro-isoquinoline-4-carboxylic acid
((S)-1-phenyl-propyl)-amide LC-MS (m/z) 447.7 (MH$^+$); $t_R$=1.22.

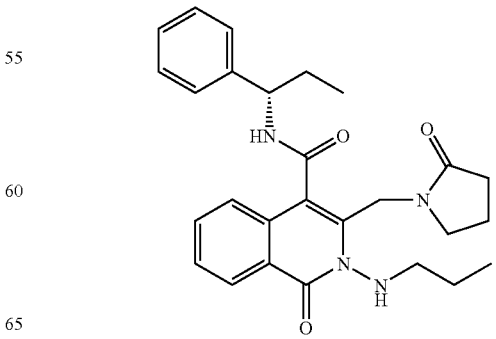

2o 1-Oxo-3-(2-oxo-pyrrolidin-1-ylmethyl)-2-propylamino-1,2-dihydro-isoquinoline-4-carboxylic acid ((S)-1-phenyl-propyl)-amide LC-MS (m/z) 461.6 (MH$^+$); $t_R$=1.32.

2p 2-Ethylamino-8-fluoro-3-methyl-1-oxo-1,2-dihydro-isoquinoline-4-carboxylic acid [(S)-cyclopropyl-(3-fluoro-phenyl)-methyl]-amide LC-MS (m/z) 412.4 (MH$^+$); $t_R$=1.38.

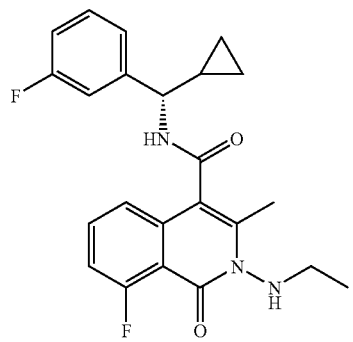

2q 8-Fluoro-3-methyl-1-oxo-2-propylamino-1,2-dihydro-isoquinoline-4-carboxylic acid [(S)-cyclopropyl-(3-fluoro-phenyl)-methyl]-amide LC-MS (m/z) 426.3 (MH$^+$); $t_R$=1.51.

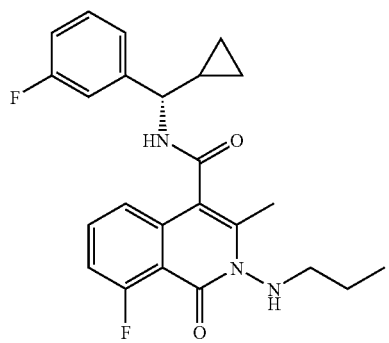

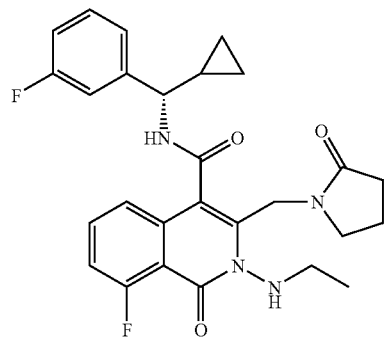

2r 2-Ethylamino-8-fluoro-1-oxo-3-(2-oxo-pyrrolidin-1-ylmethyl)-1,2-dihydro-isoquinoline-4-carboxylic acid [(S)-cyclopropyl-(3-fluoro-phenyl)-methyl]-amide LC-MS (m/z) 495.7 (MH$^+$); $t_R$=1.27.

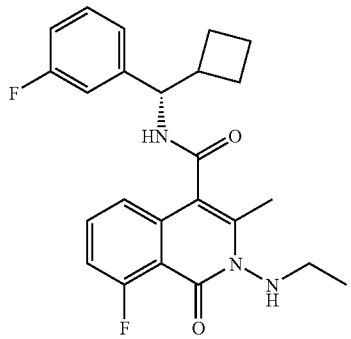

2s 2-Ethylamino-8-fluoro-3-methyl-1-oxo-1,2-dihydro-isoquinoline-4-carboxylic acid [(S)-cyclobutyl-(3-fluoro-phenyl)-methyl]-amide LC-MS (m/z) 426.3 (MH$^+$); $t_R$=1.47. LC-High Resolution MS calc. for $C_{24}H_{26}F_2N_3O_2$ 426.1988 (MH$^+$). found 426.1980.

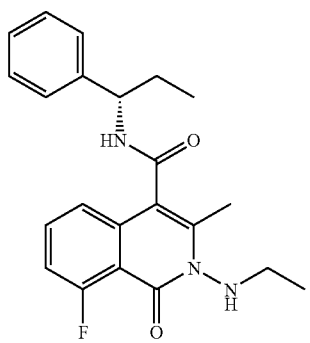

2t 2-Ethylamino-8-fluoro-3-methyl-1-oxo-1,2-dihydro-isoquinoline-4-carboxylic acid ((S)-1-phenyl-propyl)-amide LC-MS (m/z) 382.4 (MH$^+$); $t_R$=1.26.

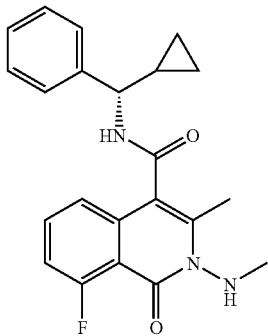

2u 8-Fluoro-3-methyl-2-methylamino-1-oxo-1,2-dihydro-isoquinoline-4-carboxylic acid ((S)-cyclopropyl-phenyl-methyl)-amide LC-MS (m/z) 380.4 (MH$^+$); $t_R$=1.17.

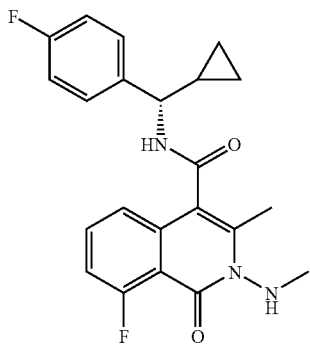

2v 8-Fluoro-3-methyl-2-methylamino-1-oxo-1,2-dihydro-isoquinoline-4-carboxylic acid [(S)-cyclopropyl-(4-fluoro-phenyl)-methyl]-amide LC-MS (m/z) 398.0 (MH$^+$); $t_R$=1.21.

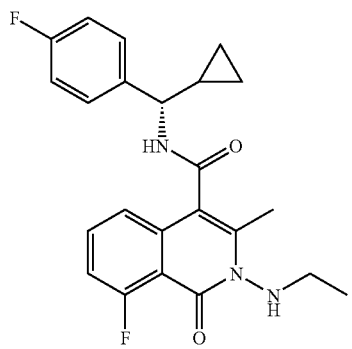

2w 2-Ethylamino-8-fluoro-3-methyl-1-oxo-1,2-dihydro-isoquinoline-4-carboxylic acid [(S)-cyclopropyl-(4-fluoro-phenyl)-methyl]-amide LC-MS (m/z) 412.3 (MH$^+$); $t_R$=1.32.

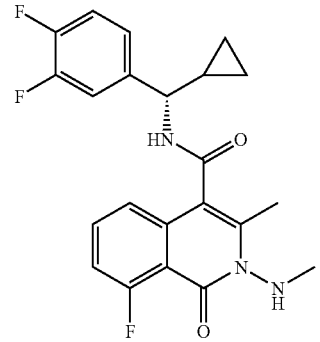

2x 8-Fluoro-3-methyl-2-methylamino-1-oxo-1,2-dihydro-isoquinoline-4-carboxylic acid [(S)-cyclopropyl-(3,4-difluoro-phenyl)-methyl]-amide LC-MS (m/z) 416.3 (MH$^+$); $t_R$=1.26.

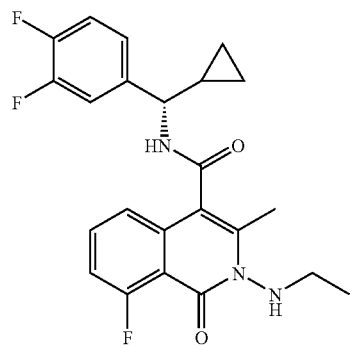

2y 2-Ethylamino-8-fluoro-3-methyl-1-oxo-1,2-dihydro-isoquinoline-4-carboxylic acid [(S)-cyclopropyl-(3,4-difluoro-phenyl)-methyl]-amide LC-MS (m/z) 430.3 (MH$^+$); $t_R$=1.37.

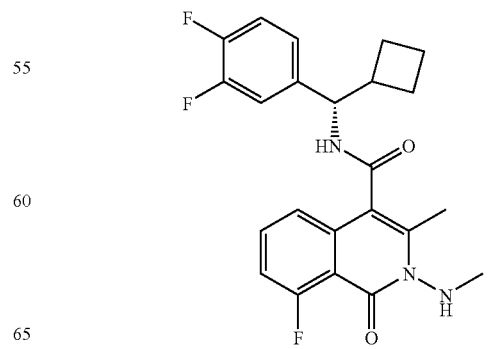

2z 8-Fluoro-3-methyl-2-methylamino-1-oxo-1,2-dihydro-isoquinoline-4-carboxylic acid [(S)-cyclobutyl-(3,4-difluoro-phenyl)-methyl]-amide LC-MS (m/z) 430.4 (MH⁺); $t_R$=1.39.

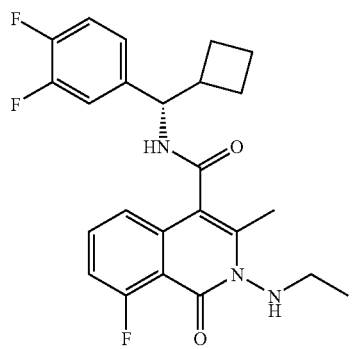

2aa 2-Ethylamino-8-fluoro-3-methyl-1-oxo-1,2-dihydro-isoquinoline-4-carboxylic acid [(S)-cyclobutyl-(3,4-difluoro-phenyl)-methyl]-amide LC-MS (m/z) 444.5 (MH⁺); $t_R$=1.5.

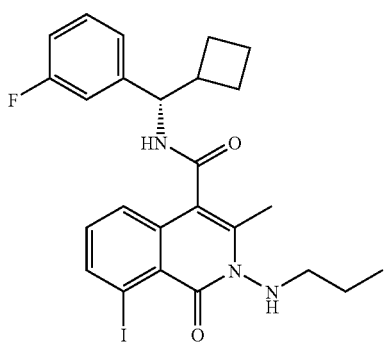

2ab 8-Iodo-3-methyl-1-oxo-2-propylamino-1,2-dihydro-isoquinoline-4-carboxylic acid [(S)-cyclobutyl-(3-fluoro-phenyl)-methyl]-amide LC-MS (method C) (m/z) 548.4 (MH⁺); $t_R$=1.86.

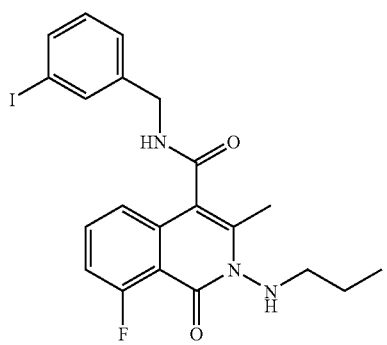

2ac 8-Fluoro-3-methyl-1-oxo-2-propylamino-1,2-dihydro-isoquinoline-4-carboxylic acid 3-iodo-benzylamide LC-MS (method C) (m/z) 494.4 (MH⁺); $t_R$=1.62.

Example 3

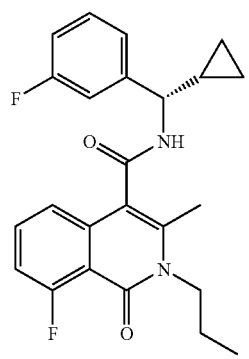

3a 8-Fluoro-3-methyl-1-oxo-2-propyl-1,2-dihydro-isoquinoline-4-carboxylic acid [(S)-cyclopropyl-(3-fluoro-phenyl)-methyl]-amide Oxalyl chloride (0.7 mL, 8 mmol) was added to N-propyl-acetamide (1.11 mL, 10 mmol) and 2,6-lutidine (1.39 mL, 12 mmol) in 50 mL 1,2-dichloroethane at 0° C. The reaction mixture was stirred at 0° C. for 30 minutes. 2-({[(S)-Cyclopropyl-(3-fluoro-phenyl)-methyl]-carbamoyl}-methyl)-6-fluoro-benzoic acid was added and the reaction mixture was refluxed for 20 hours. The reaction mixture was poured into 35 mL 1N HCl (aq.) and 50 mL brine. The mixture was extracted with ethyl acetate (250 mL). The organic phase was washed with brine, dried over MgSO₄ and concentrated in vacuo. The crude product was flash chromatographed on silica gel (gradient heptane-ethyl acetate) to give 344 mg of the title compound, yield 42%. LC-MS (m/z) 411.3 (MH+); $t_R$=1.34.

The following compounds were obtained analogously:

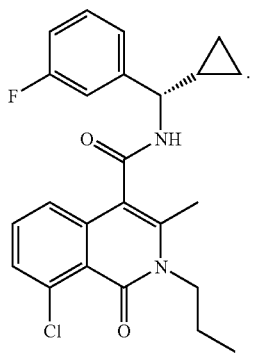

3b 8-Chloro-3-methyl-1-oxo-2-propyl-1,2-dihydro-isoquinoline-4-carboxylic acid [(S)-cyclopropyl-(3-fluoro-phenyl)-methyl]-amide LC-MS (m/z) 427.1 (MH+); $t_R$=1.52.

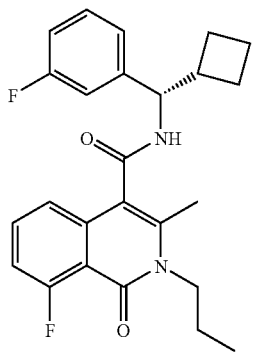

3c 8-Fluoro-3-methyl-1-oxo-2-propyl-1,2-dihydro-isoquinoline-4-carboxylic acid [(S)-cyclobutyl-(3-fluoro-phenyl)-methyl]-amide LC-MS (m/z) 425.0 (MH+); $t_R$=1.54.

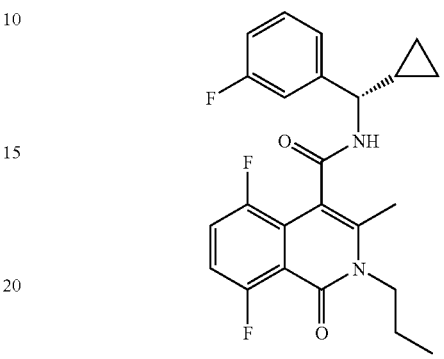

3d 5,8-Difluoro-3-methyl-1-oxo-2-propyl-1,2-dihydro-isoquinoline-4-carboxylic acid [(S)-cyclopropyl-(3-fluoro-phenyl)-methyl]-amide LC-MS (m/z) 429.2 (MH+); $t_R$=1.37

Example 4

The following compounds were obtained analogously as in example 1 by condensation between keto-acids of the general formula XXV and corresponding amino compounds of the general formula VI under microwave irradiation in acetonitrile at 170° C. The title compounds were purified by preparative LC-MS or by flash chromatography on silica gel:

| | Chemical name | Structure | $t_R$ (min)* | m/z (MH+) | MW |
|---|---|---|---|---|---|
| 4a | 8-Fluoro-2,3-dimethyl-1-oxo-1,2-dihydro-isoquinoline-4-carboxylic acid [(S)-cyclopropyl-(3-fluoro-phenyl)-methyl]-amide | 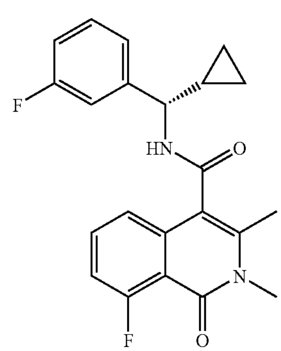 | 1.2 | 383.4 | 328.41 |

| | Chemical name | Structure | $t_R$ (min)* | m/z (MH⁺) | MW |
|---|---|---|---|---|---|
| 4b | 8-Fluoro-2-isopropyl-3-methyl-1-oxo-1,2-dihydro-isoquinoline-4-carboxylic acid [(S)-cyclopropyl-(3-fluoro-phenyl)-methyl]-amide | 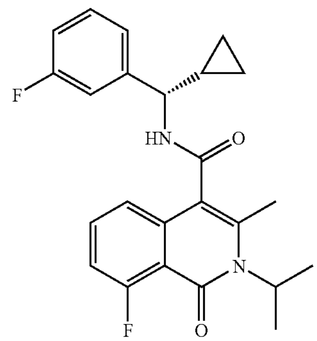 | 1.4 | 411.3 | 410.46 |
| 4c | 2-Cyanomethyl-8-fluoro-3-methyl-1-oxo-1,2-dihydro-isoquinoline-4-carboxylic acid [(S)-cyclopropyl-(3-fluoro-phenyl)-methyl]-amide | 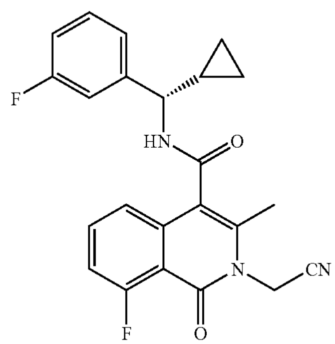 | 1.26 | 408.5 | 407.42 |
| 4d | 8-Fluoro-3-methyl-1-oxo-2-(3,3,3-trifluoro-propyl)-1,2-dihydro-isoquinoline-4-carboxylic acid [(S)-cyclopropyl-(3-fluoro-phenyl)-methyl]-amide | 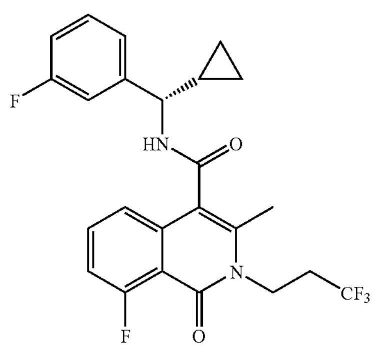 | 1.48 | 465.5 | 464.43 |
| 4e | 2-(2,2-Difluoro-propyl)-8-fluoro-3-methyl-1-oxo-1,2-dihydro-isoquinoline-4-carboxylic acid [(S)-cyclopropyl-(3-fluoro-phenyl)-methyl]-amide | 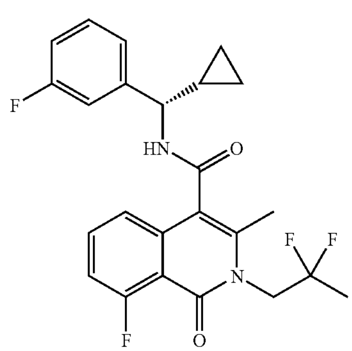 | 1.41 | 447.7 | 446.44 |

| | Chemical name | Structure | $t_R$ (min)* | m/z (MH+) | MW |
|---|---|---|---|---|---|
| 4f | 8-Fluoro-2-(2-methoxy-ethyl)-3-methyl-1-oxo-1,2-dihydro-isoquinoline-4-carboxylic acid [(S)-cyclopropyl-(3-fluoro-phenyl)-methyl]-amide | 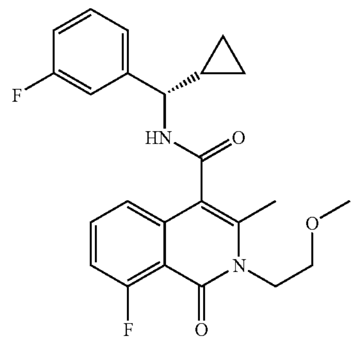 | 1.28 | 427.2 | 426.46 |
| 4g | 8-Fluoro-3-methyl-1-oxo-2-(2-pyrrolidin-1-yl-ethyl)-1,2-dihydro-isoquinoline-4-carboxylic acid [(S)-cyclopropyl-(3-fluoro-phenyl)-methyl]-amide | 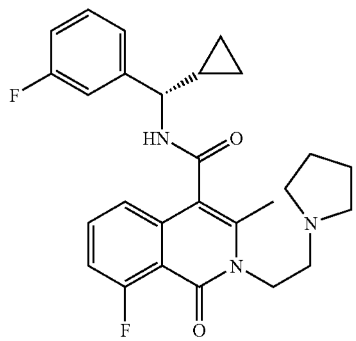 | 0.89 | 466.4 | 465.54 |
| 4h | 2-Allyl-3-methyl-1-oxo-1,2-dihydro-isoquinoline-4-carboxylic acid ((S-1-phenyl-propyl)-amide | 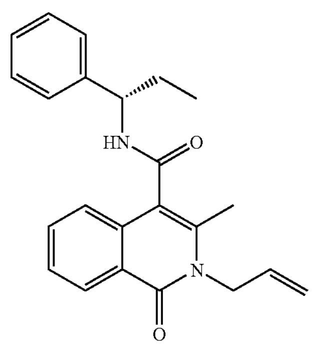 | 1.30 | 361.6 | 360.45 |
| 4i | 2-(3-Methoxy-propyl)-3-methyl-1-oxo-1,2-dihydro-isoquinoline-4-carboxylic acid ((S)-1-phenyl-propyl)-amide | 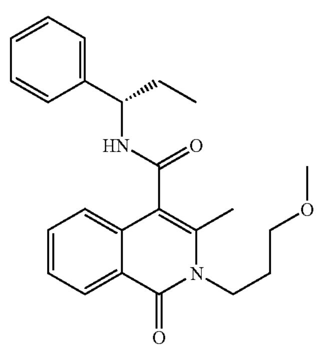 | 1.27 | 393.6 | 392.5 |

-continued

| | Chemical name | Structure | $t_R$ (min)* | m/z (MH⁺) | MW |
|---|---|---|---|---|---|
| 4j | 6,8-Difluoro-3-methyl-1-oxo-2-(3,3,3-trifluoro-propyl)-1,2-dihydro-isoquinoline-4-carboxylic acid [(S)-cyclopropyl-(3-fluoro-phenyl)-methyl]-amide | 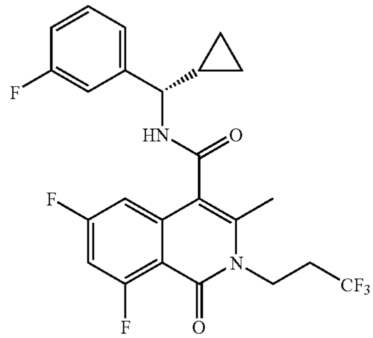 | 1.53 | 483.0 | 482.42 |
| 4k | 3-Methyl-1-oxo-2-prop-2-ynyl-1,2-dihydro-isoquinoline-4-carboxylic acid ((S)-1-phenyl-propyl)-amide | 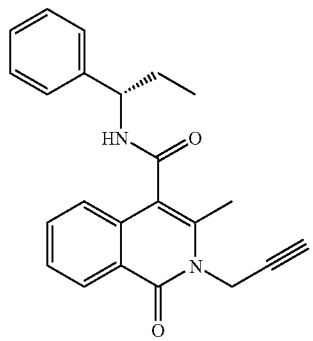 | 1.26 | 359.1 | 358.44 |
| 4l | 8-Fluoro-1-oxo-3-(2-oxo-pyrrolidin-1-ylmethyl)-2-(3,3,3-trifluoro-propyl)-1,2-dihydro-isoquinoline-4-carboxylic acid [(S)-cyclopropyl-(3-fluoro-phenyl)-methyl]-amide | 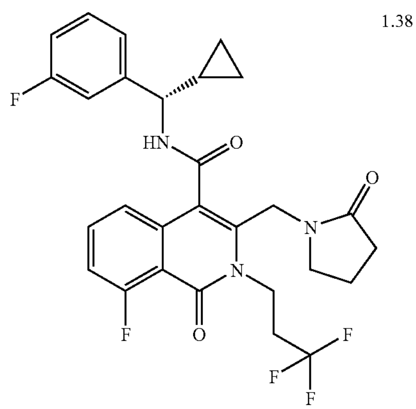 | 1.38 | 548.5 | 547.52 |
| 4m | 2-Cyclopropylmethyl-8-fluoro-3-methyl-1-oxo-1,2-dihydro-isoquinoline-4-carboxylic acid [(S)-cyclopropyl-(3-fluoro-phenyl)-methyl]-amide | 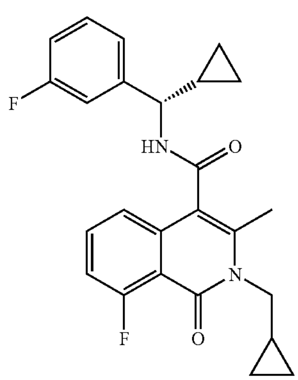 | 0.8 (B) | 423.0 | 422.47 |

-continued

| | Chemical name | Structure | $t_R$ (min)* | m/z (MH$^+$) | MW |
|---|---|---|---|---|---|
| 4n | 8-Fluoro-3-methyl-1-oxo-2-(5-oxo-pyrrolidin-2-ylmethyl)-1,2-dihydro-isoquinoline-4-carboxylic acid [(S)-cyclopropyl-(3-fluoro-phenyl)-methyl]-amide | 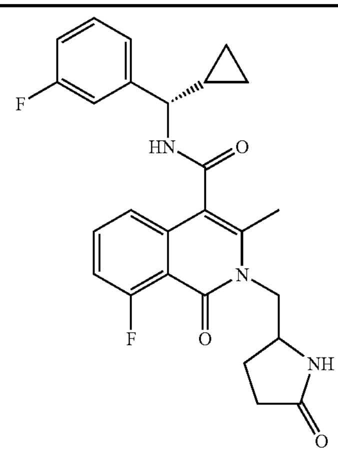 | 1.08 | 466.1 | 465.50 |
| 4o | 8-Fluoro-3-methyl-1-oxo-2-piperidin-3-ylmethyl-1,2-dihydro-isoquinoline-4-carboxylic acid [(S)-cyclopropyl-(3-fluoro-phenyl)-methyl]-amide | 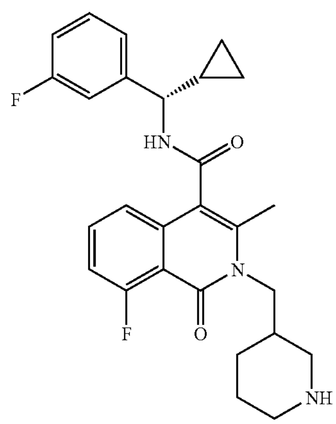 | 0.91 | 466.4 | 465.54 |
| 4p | 8-Fluoro-2-(2-hydroxy-ethyl)-3-methyl-1-oxo-1,2-dihydro-isoquinoline-4-carboxylic acid [(S)-cyclobutyl-(3-fluoro-phenyl)-methyl]-amide | 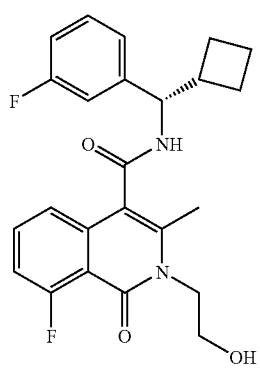 | 1.21 | 427.1 | 426.46 |
| 4q | 8-Fluoro-3-methyl-1-oxo-2-(R)-tetrahydro-furan-3-yl-1,2-dihydro-isoquinoline-4-carboxylic acid [(S)-cyclobutyl-(3-fluoro-phenyl)-methyl]-amide | 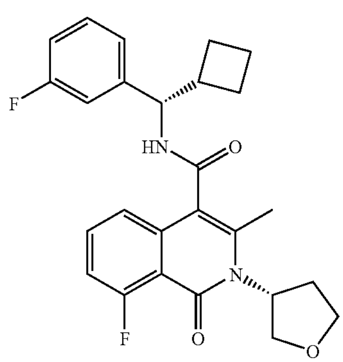 | 1.31 | 453.4 | 452.50 |

| | Chemical name | Structure | $t_R$ (min)* | m/z (MH⁺) | MW |
|---|---|---|---|---|---|
| 4r | 8-Fluoro-3-methyl-1-oxo-2-(S)-tetrahydro-furan-3-yl-1,2-dihydro-isoquinoline-4-carboxylic acid [(S)-cyclobutyl-(3-fluoro-phenyl)-methyl]-amide | 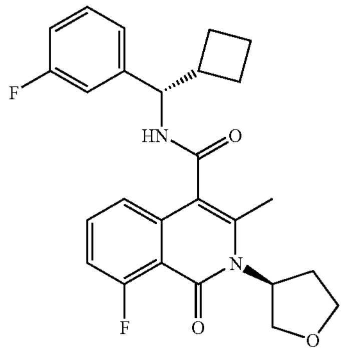 | 1.31 | 453.5 | 452.50 |
| 4s | 8-Fluoro-3-methyl-1-oxo-2-(tetrahydro-pyran-4-yl)-1,2-dihydro-isoquinoline-4-carboxylic acid [(S)-cyclobutyl-(3-fluoro-phenyl)-methyl]-amide | 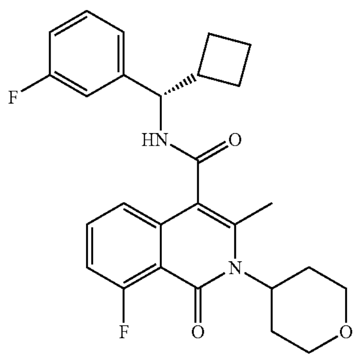 | 1.35 | 467.5 | 466.53 |
| 4t | 2-Ethoxy-8-fluoro-3-methyl-1-oxo-1,2-dihydro-isoquinoline-4-carboxylic acid [(S)-cyclobutyl-(3-fluoro-phenyl)-methyl]-amide | 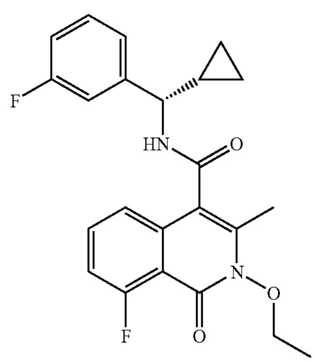 | 1.39 | 427.2 | 426.46 |
| 4u | 8-Fluoro-3-methyl-1-oxo-2-propoxy-1,2-dihydro-isoquinoline-4-carboxylic acid [(S)-cyclobutyl-(3-fluoro-phenyl)-methyl]-amide | 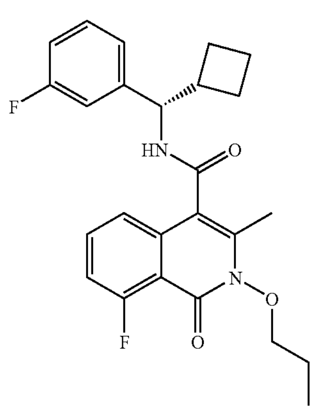 | 1.51 | 441.2 | 440.49 |

-continued

| | Chemical name | Structure | $t_R$ (min)* | m/z (MH$^+$) | MW |
|---|---|---|---|---|---|
| 4v | 2-Ethoxy-8-fluoro-3-methyl-1-oxo-1,2-dihydro-isoquinoline-4-carboxylic acid [(S)-cyclopropyl-(3-fluoro-phenyl)-methyl]-amide | 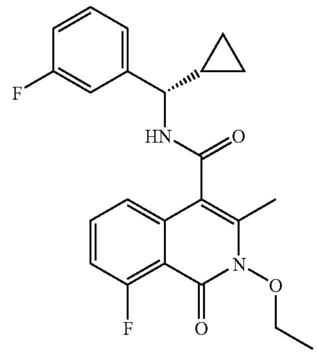 | 1.27 | 413.5 | 412.43 |
| 4w | 8-Fluoro-3-methyl-1-oxo-2-propoxy-1,2-dihydro-isoquinoline-4-carboxylic acid [(S)-cyclopropyl-(3-fluoro-phenyl)-methyl]-amide | 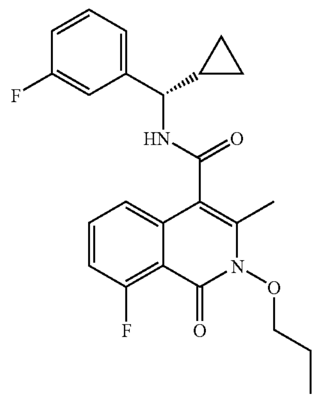 | 1.38 | 427.2 | 426.46 |
| 4x | 2-Allyl-8-fluoro-3-methyl-1-oxo-1,2-dihydro-isoquinoline-4-carboxylic acid [(S)-cyclobutyl-(3-fluoro-phenyl)-methyl]-amide | 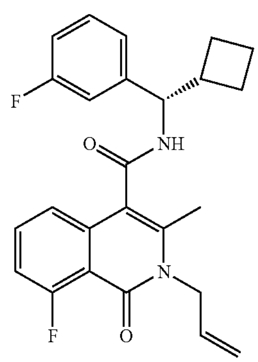 | 0.8 (B) | 423.0 | 422.47 |
| 4y | 2-Allyl-8-fluoro-3-methyl-1-oxo-1,2-dihydro-isoquinoline-4-carboxylic acid [(S)-cyclopropyl-(3-fluoro-phenyl)-methyl]-amide | 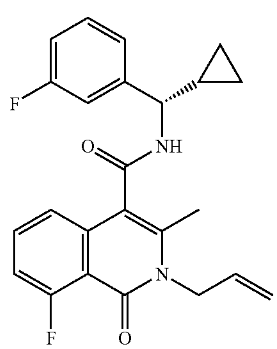 | 0.76 (B) | 408.9 | 408.45 |

-continued

| | Chemical name | Structure | $t_R$ (min)* | m/z (MH+) | MW |
|---|---|---|---|---|---|
| 4z | 8-Fluoro-3-methyl-1-oxo-2-prop-2-ynyl-1,2-dihydro-isoquinoline-4-carboxylic acid [(S)-cyclobutyl-(3-fluoro-phenyl)-methyl]-amide | 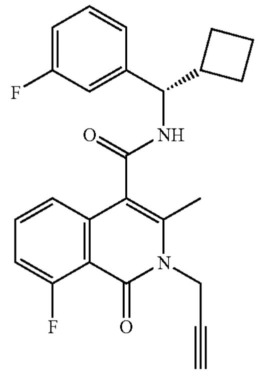 | 0.8 (B) | 420.9 | 420.46 |
| 4aa | 8-Fluoro-3-methyl-1-oxo-2-prop-2-ynyl-1,2-dihydro-isoquinoline-4-carboxylic acid [(S)-cyclopropyl-(3-fluoro-phenyl)-methyl]-amide | 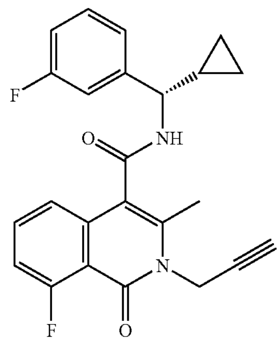 | 0.75 (B) | 407.3 | 406.43 |
| 4ab | 2-Cyclopropylmethyl-8-fluoro-3-methyl-1-oxo-1,2-dihydro-isoquinoline-4-carboxylic acid [(S)-cyclobutyl-(3-fluoro-phenyl)-methyl]-amide | 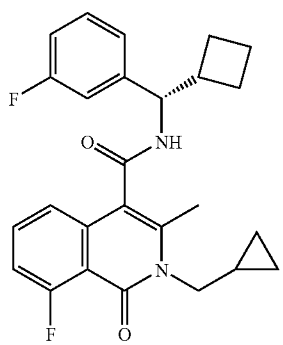 | 0.86 (B) | 437.5 | 436.50 |

*LC-MS method A was used unless noted otherwise.

Example 5

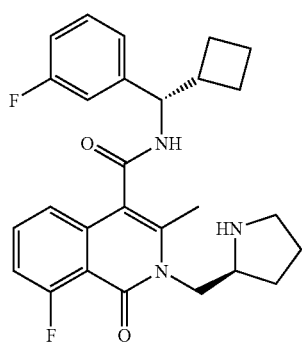

5a 8-Fluoro-3-methyl-1-oxo-2-(S)-1-pyrrolidin-2-ylmethyl-1,2-dihydro-isoquinoline-4-carboxylic acid [(S)-cyclobutyl-(3-fluoro-phenyl)-methyl]-amide (S)-2-Aminomethyl-pyrrolidine-1-carboxylic acid tert-butyl ester (510 mg, 2.54 mmol) and 2-(1-{[(S)-cyclobutyl-(3-fluoro-phenyl)-methyl]-carbamoyl}-2-oxo-propyl)-6-fluoro-benzoic acid (851 mg, 2.12 mmol) were condensed analogously to the method described for example 4 to give (S)-2-(4-{[(S)-Cyclobutyl-(3-fluoro-phenyl)-methyl]-carbamoyl}-8-fluoro-3-methyl-1-oxo-1H-isoquinolin-2-ylmethyl)-pyrrolidine-1-carboxylic acid tert-butyl ester. The Boc-protection group was removed analogously to the method described for example 6 with trifluoroacetic acid in 1,2-dichloroethane to give the title compound. LC-MS (m/z) 466.3 (MH+); $t_R$=0.96.

The following compounds were obtained analogously:

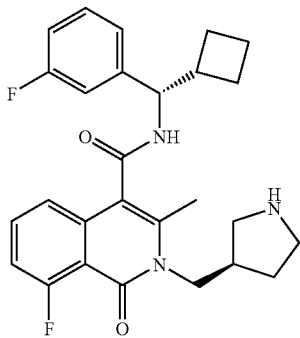

5b 8-Fluoro-3-methyl-1-oxo-2-(R)-1-pyrrolidin-3-ylmethyl-1,2-dihydro-isoquinoline-4-carboxylic acid [(S)-cyclobutyl-(3-fluoro-phenyl)-methyl]-amide LC-MS (m/z) 466.4 (MH+); $t_R$=0.98.

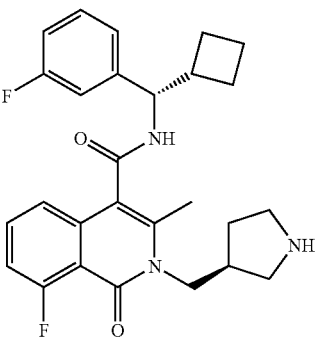

5c 8-Fluoro-3-methyl-1-oxo-2-(S)-1-pyrrolidin-3-ylmethyl-1,2-dihydro-isoquinoline-4-carboxylic acid [(S)-cyclobutyl-(3-fluoro-phenyl)-methyl]-amide LC-MS (m/z) 466.2 (MH+); $t_R$=0.98.

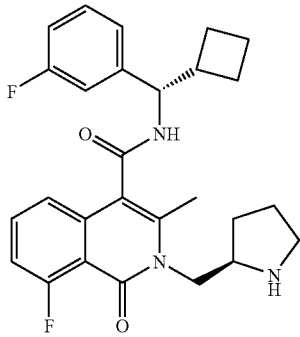

5d 8-Fluoro-3-methyl-1-oxo-2-(R)-1-pyrrolidin-2-ylmethyl-1,2-dihydro-isoquinoline-4-carboxylic acid [(S)-cyclobutyl-(3-fluoro-phenyl)-methyl]-amide LC-MS (method B) (m/z) 466.3 (MH+); $t_R$=0.59.

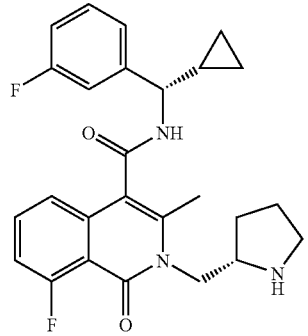

5e 8-Fluoro-3-methyl-1-oxo-2-(S)-1-pyrrolidin-2-ylmethyl-1,2-dihydro-isoquinoline-4-carboxylic acid [(S)-cyclopropyl-(3-fluoro-phenyl)-methyl]-amide LC-MS (m/z) 452.4 (MH+); $t_R$=0.88.

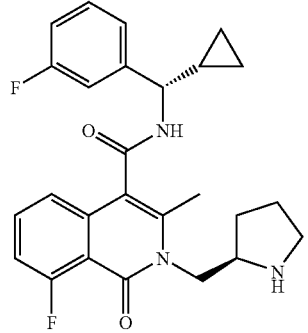

5f 8-Fluoro-3-methyl-1-oxo-2-(R)-1-pyrrolidin-2-ylmethyl-1,2-dihydro-isoquinoline-4-carboxylic acid [(S)-cyclopropyl-(3-fluoro-phenyl)-methyl]-amide LC-MS (m/z) 452.3 (MH+); $t_R$=0.88.

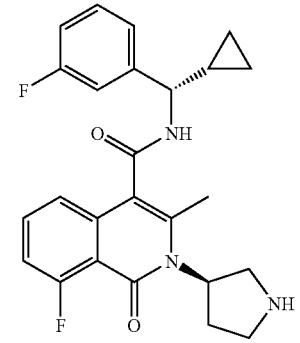

5g 8-Fluoro-3-methyl-1-oxo-2-(R)-1-pyrrolidin-3-yl-1,2-dihydro-isoquinoline-4-carboxylic acid [(S)-cyclopropyl-(3-fluoro-phenyl)-methyl]-amide LC-MS (m/z) 438.5 (MH+); $t_R$=0.87.

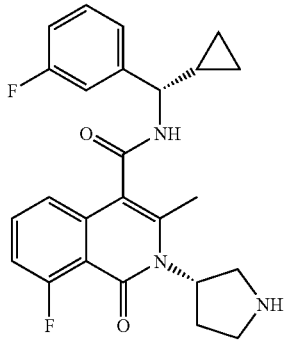

5h 8-Fluoro-3-methyl-1-oxo-2-(S)-1-pyrrolidin-3-yl-1,2-dihydro-isoquinoline-4-carboxylic acid [(S)-cyclopropyl-(3-fluoro-phenyl)-methyl]-amide LC-MS (m/z) 438.4 (MH+); $t_R$=0.88.

Example 6

Synthesis of intermediates:

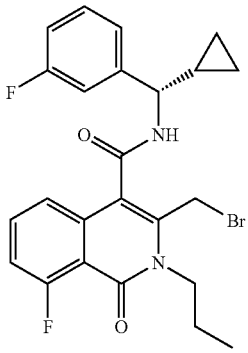

3-Bromomethyl-8-fluoro-1-oxo-2-propyl-1,2-dihydro-isoquinoline-4-carboxylic acid [(S)-cyclopropyl-(3-fluoro-phenyl)-methyl]-amide Bromine (400 mg, 2.5 mmol) in 0.5 ml 1,2-dichloroethane was added to 8-fluoro-3-methyl-1-oxo-2-propyl-1,2-dihydro-isoquinoline-4-carboxylic acid [(S)-cyclopropyl-(3-fluoro-phenyl)-methyl]-amide (344 mg, 0.84 mmol, see example 3) in 1,2-dichloroethane (20 mL) at 60° C. The reaction mixture was stirred for 15 minutes at 60° C. The reaction mixture was concentrated in vacuo to give crude 3-bromomethyl-8-fluoro-1-oxo-2-propyl-1,2-dihydro-isoquinoline-4-carboxylic acid [(S)-cyclopropyl-(3-fluoro-phenyl)-methyl]-amide, which was used in the next step without purification. LC-MS (m/z) 489.5 (MH+); $t_R$=1.55.

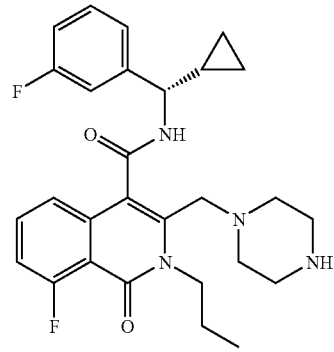

6a 8-Fluoro-1-oxo-3-piperazin-1-ylmethyl-2-propyl-1,2-dihydro-isoquinoline-4-carboxylic acid [(S)-cyclopropyl-(3-fluoro-phenyl)-methyl]-amide Triethyl amine (280 µL, 2 mmol) and piperazine-1-carboxylic acid tert-butyl ester (186 mg, 1 mmol) were added to 3-bromomethyl-8-fluoro-1-oxo-2-propyl-1,2-dihydro-isoquinoline-4-carboxylic acid [(S)-cyclopropyl-(3-fluoro-phenyl)-methyl]-amide (0.84 mmol) in 20 mL THF. The reaction mixture was stirred at room temperature for 24 hours and poured into 50 mL water and 50 mL brine. The mixture was extracted with ethyl acetate (250 mL). The organic phase was washed with brine, dried over MgSO$_4$ and concentrated in vacuo. The crude product was flash chromatographed on silica gel (gradient heptane-ethyl acetate) to give 365 mg of a mixture of 4-(4-{[(S)-cyclopropyl-(3-fluoro-phenyl)-methyl]-carbamoyl}-8-fluoro-1-oxo-2-propyl-1,2-dihydro-isoquinolin-3-ylmethyl)-piperazine-1-carboxylic acid tert-butyl ester and 8-fluoro-3-methyl-1-oxo-2-propyl-1,2-dihydro-isoquinoline-4-carboxylic acid [(S)-cyclopropyl-(3-fluoro-phenyl)-methyl]-amide. The mixture was dissolved in 7 mL 1,2-dichloroethane. 7 mL trifluoroacetic acid was added and the reaction mixture was stirred at room temperature for 2 hours and concentrated in vacuo. 50 mL sat. NaHCO$_3$ (aq) was added, and the mixture was extracted with ethyl acetate (50 mL). The organic phase was washed with brine, dried over MgSO$_4$ and concentrated in vacuo. The crude product was flash chromatographed on silica gel (ethyl acetate and then ethyl acetate:methanol:triethyl amine 3:1:1) to give 8-Fluoro-1-oxo-3-piperazin-1-ylmethyl-2-propyl-1,2-dihydro-isoquinoline-4-carboxylic acid [(S)-cyclopropyl-(3-fluoro-phenyl)-methyl]-amide, yield 50%. LC-MS (method B) (m/z) 495.5 (MH+); $t_R$=0.55.

The following compound was obtained analogously via corresponding 3-bromomethyl derivative:

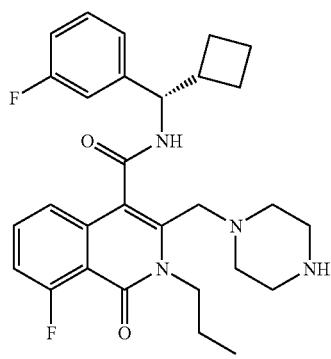

6b 8-Fluoro-1-oxo-3-piperazin-1-ylmethyl-2-propyl-1,2-dihydro-isoquinoline-4-carboxylic acid [(S)-cyclobutyl-(3-fluoro-phenyl)-methyl]-amide LC-MS (m/z) 509.3 (MH+); $t_R$=1.01

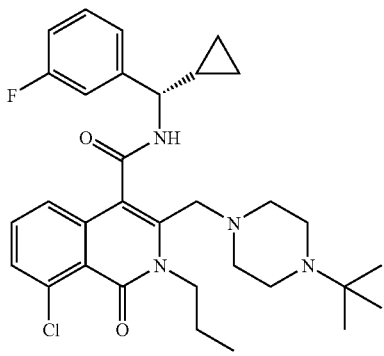

6c 3-(4-tert-Butyl-piperazin-1-ylmethyl)-8-chloro-1-oxo-2-propyl-1,2-dihydro-isoquinoline-4-carboxylic acid [(S)-cyclopropyl-(3-fluoro-phenyl)-methyl]-amide Triethyl amine (280 µL, 2 mmol) and 1-tert-butyl-piperazine (96 mg, 0.67 mmol) were added to 3-bromomethyl-8-chloro-1-oxo-2-propyl-1,2-dihydro-isoquinoline-4-carboxylic acid [(S)-cyclopropyl-(3-fluoro-phenyl)-methyl]-amide (0.56 mmol) in 10 mL THF. The reaction mixture was stirred at room temperature for 30 minutes and poured into 50 mL 0.5 N NaOH (aq). The mixture was extracted with ethyl acetate (100 mL). The organic phase was washed with brine, dried over MgSO₄ and concentrated in vacuo. The crude product was flash chromatographed on silica gel (gradient heptane-ethyl acetate/methanol) to give 190 mg of the title compound, yield 60%. LC-MS (m/z) 567.8 (MH+); $t_R$=1.07.

The following compounds were obtained analogously:

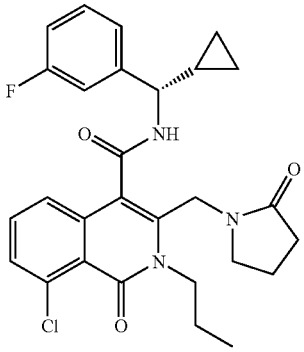

6d 8-Chloro-1-oxo-3-(2-oxo-pyrrolidin-1-ylmethyl)-2-propyl-1,2-dihydro-isoquinoline-4-carboxylic acid [(S)-cyclopropyl-(3-fluoro-phenyl)-methyl]-amide Pyrrolidinone was treated with sodium hydride in THF before addition to the corresponding 3-bromomethyl compound. LC-MS (m/z) 510.2 (MH+); $t_R$=1.43.

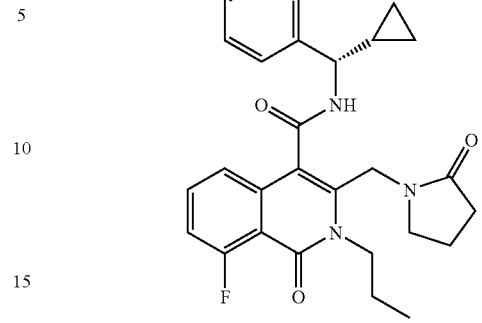

6e 8-Fluoro-1-oxo-3-(2-oxo-pyrrolidin-1-ylmethyl)-2-propyl-1,2-dihydro-isoquinoline-4-carboxylic acid [(S)-cyclopropyl-(3-fluoro-phenyl)-methyl]-amide Pyrrolidinone was treated with sodium hydride in THF before addition to the corresponding 3-bromomethyl compound. LC-MS (m/z) 494.3 (MH+); $t_R$=1.29

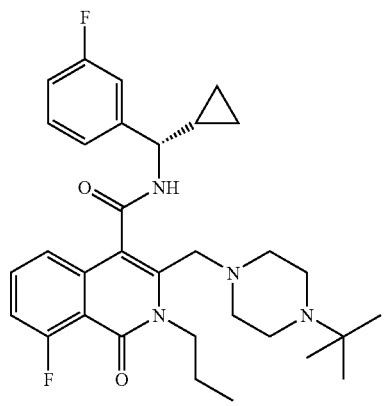

6f 3-(4-tert-Butyl-piperazin-1-ylmethyl)-8-fluoro-1-oxo-2-propyl-1,2-dihydro-isoquinoline-4-carboxylic acid [(S)-cyclopropyl-(3-fluoro-phenyl)-methyl]-amide LC-MS (m/z) 551.7 (MH+); $t_R$=0.97.

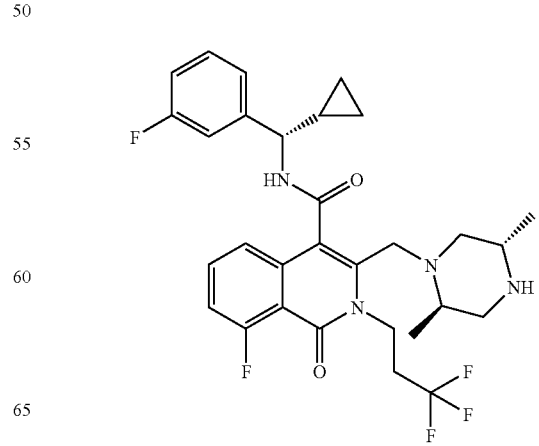

6g 3-((2R,5S)-2,5-Dimethyl-piperazin-1-ylmethyl)-8-fluoro-1-oxo-2-(3,3,3-trifluoro-propyl)-1,2-dihydro-isoquinoline-4-carboxylic acid [(S)-cyclopropyl-(3-fluoro-phenyl)-methyl]-amide.

LC-MS (m/z) 577.6 (MH+); $t_R$=1.05.

Example 7

The following compounds were obtained from the corresponding compounds described in the example 5 by reductive alkylation with appropriate aldehyde and sodium cyanoborohydride analogously to the method described for example 2 or by acylation with acetic anhydride (neat) followed by evaporation. The title compounds were isolated by SCX ion exchange, flash chromatography or by preparative LC-MS.

7a 8-Fluoro-3-methyl-2-((S)-1-methyl-pyrrolidin-2-ylmethyl)-1-oxo-1,2-dihydro-isoquinoline-4-carboxylic acid [(S)-cyclopropyl-(3-fluoro-phenyl)-methyl]-amide

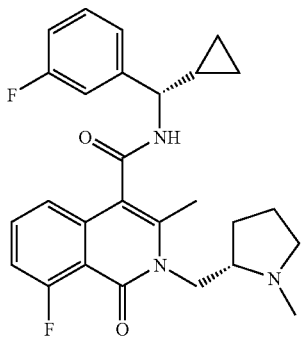

LC-MS (m/z) 466.4 (MH+); $t_R$=0.89.

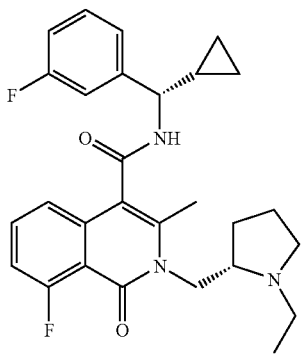

7b 2-((S)-1-Ethyl-pyrrolidin-2-ylmethyl)-8-fluoro-3-methyl-1-oxo-1,2-dihydro-isoquinoline-4-carboxylic acid [(S)-cyclopropyl-(3-fluoro-phenyl)-methyl]-amide LC-MS (m/z) 480.4 (MH+); $t_R$=0.92.

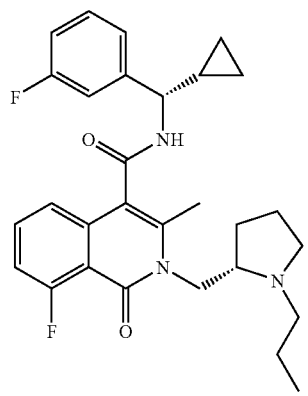

7c 8-Fluoro-3-methyl-1-oxo-2-((S)-1-propyl-pyrrolidin-2-ylmethyl)-1,2-dihydro-isoquinoline-4-carboxylic acid [(S)-cyclopropyl-(3-fluoro-phenyl)-methyl]-amide LC-MS (m/z) 494.4 (MH+); $t_R$=0.98.

7d 2-((S)-1-Acetyl-pyrrolidin-2-ylmethyl)-8-fluoro-3-methyl-1-oxo-1,2-dihydro-isoquinoline-4-carboxylic acid [(S)-cyclopropyl-(3-fluoro-phenyl)-methyl]-amide LC-MS (m/z) 494.5 (MH+); $t_R$=1.21.

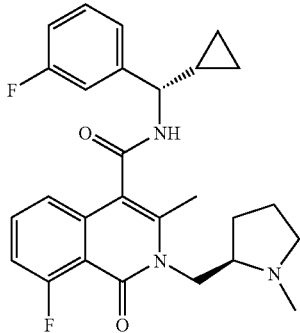

7e 8-Fluoro-3-methyl-2-((R)-1-methyl-pyrrolidin-2-ylmethyl)-1-oxo-1,2-dihydro-isoquinoline-4-carboxylic acid [(S)-cyclopropyl-(3-fluoro-phenyl)-methyl]-amide LC-MS (m/z) 466.2 (MH+); $t_R$=0.89.

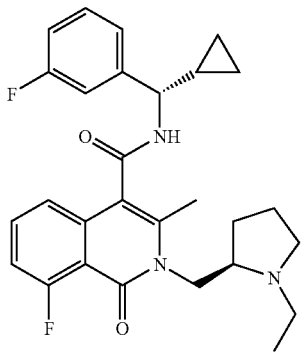

7f 2-((R)-1-Ethyl-pyrrolidin-2-ylmethyl)-8-fluoro-3-methyl-1-oxo-1,2-dihydro-isoquinoline-4-carboxylic acid [(S)-cyclopropyl-(3-fluoro-phenyl)-methyl]-amide LC-MS (m/z) 480.4 (MH+); $t_R$=0.92.

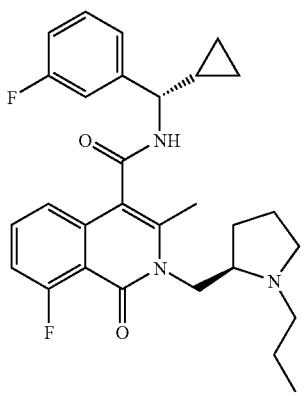

7g 8-Fluoro-3-methyl-1-oxo-2-((R)-1-propyl-pyrrolidin-2-ylmethyl)-1,2-dihydro-isoquinoline-4-carboxylic acid [(S)-cyclopropyl-(3-fluoro-phenyl)-methyl]-amide LC-MS (m/z) 494.6 (MH+); $t_R$=0.98.

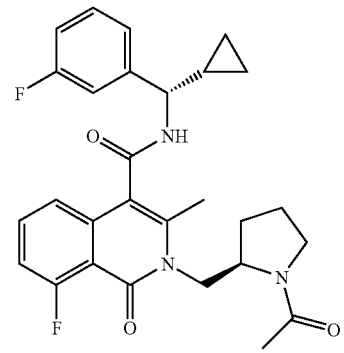

7h 2-((R)-1-Acetyl-pyrrolidin-2-ylmethyl)-8-fluoro-3-methyl-1-oxo-1,2-dihydro-isoquinoline-4-carboxylic acid [(S)-cyclopropyl-(3-fluoro-phenyl)-methyl]-amide LC-MS (m/z) 494.3 (MH+); $t_R$=1.21.

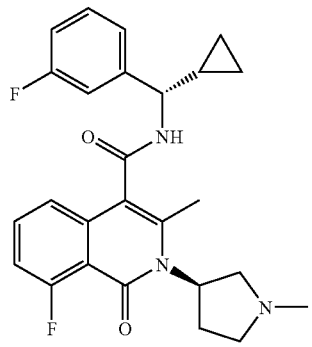

7i 8-Fluoro-3-methyl-2-((R)-1-methyl-pyrrolidin-3-yl)-1-oxo-1,2-dihydro-isoquinoline-4-carboxylic acid [(S)-cyclopropyl-(3-fluoro-phenyl)-methyl]-amide LC-MS (m/z) 452.3 (MH+); $t_R$=0.88.

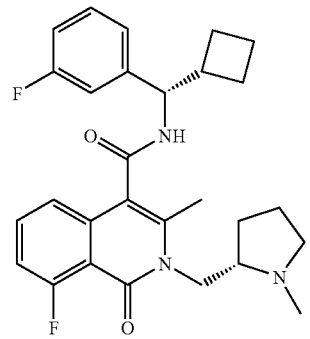

7j 8-Fluoro-3-methyl-2-((S)-1-methyl-pyrrolidin-2-ylmethyl)-1-oxo-1,2-dihydro-isoquinoline-4-carboxylic acid [(S)-cyclobutyl-(3-fluoro-phenyl)-methyl]-amide LC-MS (m/z) 480.4 (MH+); $t_R$=0.98.

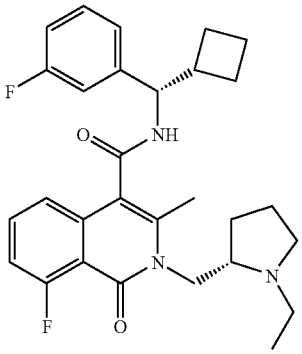

7k 2-((S)-1-Ethyl-pyrrolidin-2-ylmethyl)-8-fluoro-3-methyl-1-oxo-1,2-dihydro-isoquinoline-4-carboxylic acid[(S)-cyclobutyl-(3-fluoro-phenyl)-methyl]-amide LC-MS (m/z) 494.5 (MH+); $t_R$=1.01

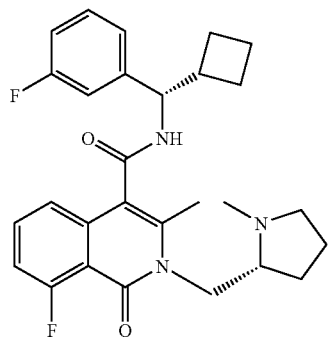

7l 8-Fluoro-3-methyl-2-((R)-1-methyl-pyrrolidin-2-ylmethyl)-1-oxo-1,2-dihydro-isoquinoline-4-carboxylic acid [(S)-cyclobutyl-(3-fluoro-phenyl)-methyl]-amide LC-MS (m/z) 480.4 (MH+); $t_R$=0.99.

Example 8

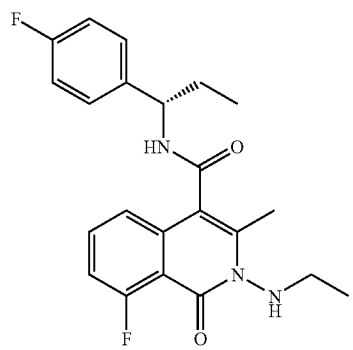

8a 2-Ethylamino-8-fluoro-3-methyl-1-oxo-1,2-dihydro-isoquinoline-4-carboxylic acid [(S)-1-(4-fluoro-phenyl)-propyl]-amide To a mixture of crude 2-ethylamino-8-fluoro-3-methyl-1-oxo-1,2-dihydro-isoquinoline-4-carboxylic acid (62 mg, 0.059 mmol), (S)-1-(4-fluoro-phenyl)-propylamine hydrochloride (40 mg), N-(3-dimethylaminopropyl)-NT-ethylcarbodiimide hydrochloride (=EDC, 191.7 mg, 1.0 mmol), 1-Hydroxybenzotriazole (135.1 mg, 1.0 mmol), N,N-Dimethylformamide (3 mL) was added followed by triethylamine (0.5 mL, 4 mmol). The obtained suspension was flashed with Argon and stirred at r.t. overnight. The reaction mixture was quenched with 1 M HCl (20 ml) then diethyl ether (20 ml), shaked and the ether layer was washed with 1M HCl (3×5 ml), sat. aq. NaHCO$_3$ (20 ml), water (2×10 ml) and rotovaped to give 36 mg of pale brown residue. It was transferred to 5 g prepacked SiO$_2$ column with 1,2-dichloroethane and flash chromatographed with the gradient heptane-ethyl acetate. The product came out with 40% ethyl acetate to give 12 mg of the title compound. LC-MS (m/z) 400.1 (MH$^+$), $t_R$=1.3. $^1$H NMR (DMSO-d$_6$, 250 MHz, 70° C., dmso-d$_5$=2.5 ppm): 0.94 (t, J=7.3 Hz, 3H, Et), 1.12 (t, J=7.1 Hz, 3H, EtNH), 1.69-1.91 (m, 2H, Et), 2.34 (s, 3H, Me), 2.94 (quintet, J=7.1 Hz, 2H, EtNH), 4.96 (q (unres. dt), J=7.6 Hz, CHNH), 6.04 (t, J=6.5 Hz, EtNH), 7.05-7.21 (m, 4H), 7.42 (dd, J=5.7 Hz, J=8.4 Hz, 2H, p-FC$_6$H$_4$), 7.61 (dt, J (d)=5.1 Hz, J (t)=8.1 Hz, 1H, C6H), 8.7 (br. d, J=8.1 Hz, NHCO). $^{19}$F NMR(CFCl$_3$=0 ppm): −110.9 (dd, J=4.2 Hz, J=11.5 Hz, C8F), −115.95 (br. s (unres. m), C$_6$H$_4$F).

The following compounds were obtained analogously:

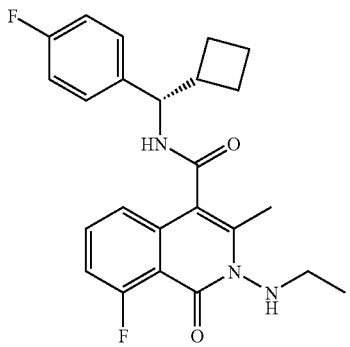

8b 2-Ethylamino-8-fluoro-3-methyl-1-oxo-1,2-dihydro-isoquinoline-4-carboxylic acid [(S)-cyclobutyl-(4-fluoro-phenyl)-methyl]-amide LC-MS (m/z) 426.4 (MH$^+$); t$_R$=1.45.

The following compound was obtained analogously (from (4-Bromo-8-fluoro-3-methyl-1-oxo-1H-isoquinolin-2-yl)-propyl-carbamic acid tert-butyl ester followed by standard tert-butoxy carbonyl deprotection):

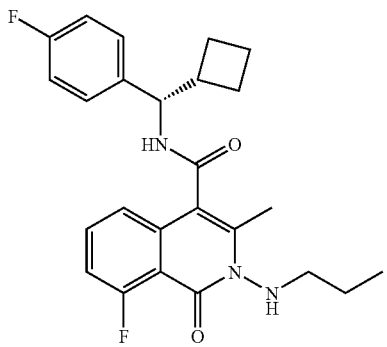

8c 8-Fluoro-3-methyl-1-oxo-2-propylamino-1,2-dihydro-isoquinoline-4-carboxylic acid [(S)-cyclobutyl-(4-fluoro-phenyl)-methyl]-amide LC-MS (m/z) 440.2 (MH$^+$); t$_R$=1.57.

Example 9

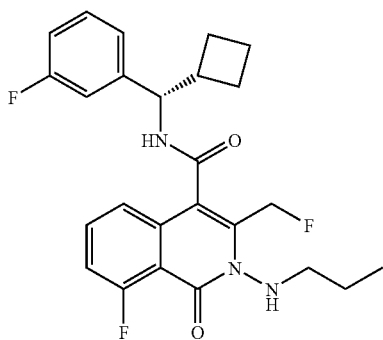

9a 8-Fluoro-3-fluoromethyl-1-oxo-2-propylamino-1,2-dihydro-isoquinoline-4-carboxylic acid [(S)-cyclobutyl-(3-fluoro-phenyl)-methyl]-amide 3-Bromomethyl-8-fluoro-1-oxo-2-propylamino-1,2-dihydro-isoquinoline-4-carboxylic acid [(S)-cyclobutyl-(3-fluoro-phenyl)-methyl]-amide (27 mg, 0.052 mmol) N,N-Dimethylformamide (2 mL) and potassium fluoride (0.015 g, 0.26) were stirred at room temperature overnight. The reaction mixture was poured into water. The mixture was extracted with ethyl acetate. The organic phase was washed with brine, dried over MgSO4 and concentrated in vacuo. The crude was purified by preparative HPLC to give the title compound.

LC-MS (m/z) 458.3 (MH$^+$); t$_R$=1.67.

Example 10

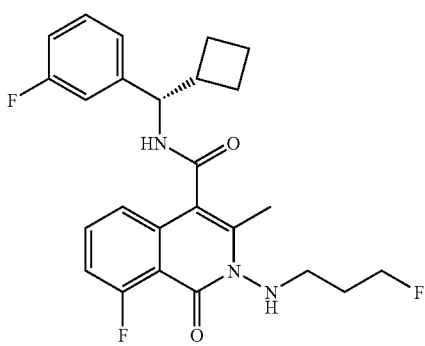

10a 8-Fluoro-2-(3-fluoro-propylamino)-3-methyl-1-oxo-1,2-dihydro-isoquinoline-4-carboxylic acid [(S)-cyclobutyl-(3-fluoro-phenyl)-methyl]-amide To (4-{[(S)-cyclobutyl-(3-fluoro-phenyl)-methyl]-carbamoyl}-8-fluoro-3-methyl-1-oxo-1H-isoquinolin-2-yl)-carbamic acid tert-butyl ester (0.5000 g, 1.005 mmol; prepared as described in example 8) and tetra-N-butylammonium bromide (0.340 g, 1.05 mmol) in toluene (10 mL, 90 mmol) was added potassium hydroxide (84.6 mg, 1.51 mmol) (powdered). The reaction was stirred at 50° C. for 10 minutes. 1-Iodo-3-fluoropropane (0.525 g, 2.79 mmol) was added and the reaction mixture was stirred for 1 hour at 50° C. The temperature was raised to 80° C. and the reaction mixture was stirred for another for 2 hours. The reaction mixture was cooled to room temperature and washed with 50 ml of water, dried over MgSO4 and was concentrated in vacuo to give 0.76 g (4-{[(S)-cyclobutyl-(3-fluoro-phenyl)-methyl]-carbamoyl}-8-fluoro-3-methyl-1-oxo-1H-isoquinolin-2-yl)-(3-fluoro-propyl)-carbamic acid tert-butyl ester as an oil. The Boc-protection group was removed analogously to the method described in example 6 with trifluoroacetic acid in 1,2-dichloroethane to give the title compound.

LC-MS (m/z) 458.2 (MH+); t$_R$=1.53.

The following compounds were obtained analogously:

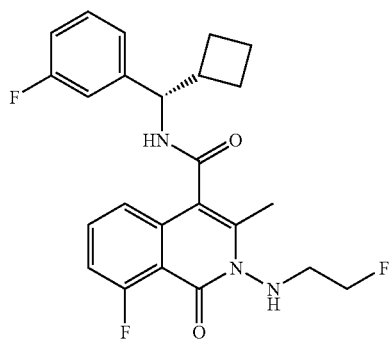

10b 8-Fluoro-2-(2-fluoro-propylamino)-3-methyl-1-oxo-1,2-dihydro-isoquinoline-4-carboxylic acid [(S)-cyclobutyl-(3-fluoro-phenyl)-methyl]-amide LC-MS (m/z) 444.6 (MH+); $t_R$=1.45

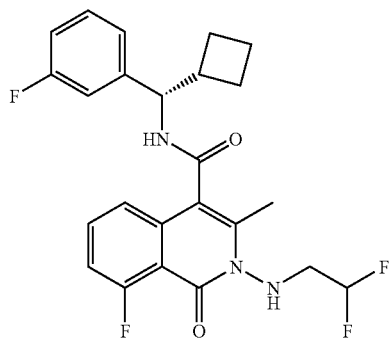

10c 2-(2,2-Difluoro-ethylamino)-8-fluoro-3-methyl-1-oxo-1,2-dihydro-isoquinoline-4-carboxylic acid [(S)-cyclobutyl-(3-fluoro-phenyl)-methyl]-amide LC-MS (m/z) 462.5 (MH+); $t_R$=1.54

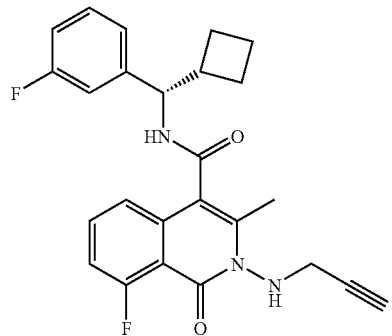

10d 8-Fluoro-3-methyl-1-oxo-2-prop-2-ynylamino-1,2-dihydro-isoquinoline-4-carboxylic acid [(S)-cyclobutyl-(3-fluoro-phenyl)-methyl]-amide LC-MS (m/z) 436.4 (MH+); $t_R$=1.49

Example 11

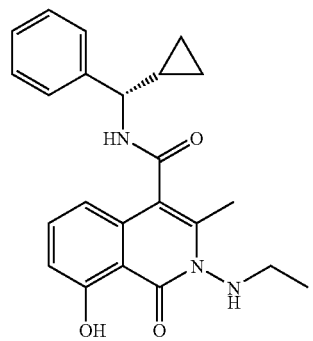

11a 2-ethylamino-8-hydroxy-3-methyl-1-oxo-1,2-dihydro-isoquinoline-4-carboxylic acid ((S)-cyclopropyl-phenyl-methyl)-amide A mixture of 2-ethylamino-8-fluoro-3-methyl-1-oxo-1,2-dihydro-isoquinoline-4-carboxylic acid ((S)-cyclopropyl-phenyl-methyl)-amide (47.0 mg, 0.119 mmol, sodium nitrite (80.0 mg, 1.16 mmol), and N,N-dimethylformamide (0.2 mL) was heated under microwave irradiation at 220° C. for 60 min. Partitioned between EtOAc and water (4×10 ml), then combined aqueous phases were extracted with ether (15 ml), which was washed with water (4×10 ml). The combined organic solution was concentrated in vacuo, and purified by flash chromatography (with a gradient of heptane-ethylacetate) to give 2-ethylamino-8-hydroxy-3-methyl-1-oxo-1,2-dihydro-isoquinoline-4-carboxylic acid ((S)-cyclopropyl-phenyl-methyl)-amide as a yellow solid.

LC-MS (m/z) 392.7 (MH+); $t_R$=1.52

Reagents used for the preparation of the compounds.

| Name | Supplier | CAS no. | Cat. no. |
|---|---|---|---|
| (S)-(−)-1-Phenylpropylamine | Lancaster | 3789-59-1 | X16320G0025 |
| 1-Ethyl-3-(3-dimethylaminopropyl)carbodiimide hydrochloride (EDC) | Aldrich | 25952-53-8 | 16,146-2 |
| 1-Hydroxybenzotriazole (HOBT) | ABCR | 2592-95-2 | AV21700 |
| Homophthalic anhydride | ABCR | 703-59-3 | AV15538 |
| 1-Bromo-3-fluorobenzene | Aldrich | 1073-06-9 | B67007 |
| Xantphos (=4,5-bis(diphenylphosphino)-9,9-dimethylxanthene) | Aldrich | 161265-03-8 | 52,646-0 |
| N-bromosuccinimide | Aldrich | 128-08-5 | B8,125-5 |
| N-tert-butylpiperazine | 3B-Medical | 38216-72-7 | 3B-2316 |
| 2-pyrrolidinone | Aldrich | 616-45-5 | P7,437-0 |
| Sodium hydride | Aldrich | 7646-69-7 | 45,291-2 |
| Bromine | Merck | 7726-95-6 | 101948 |
| Triethyl orthoacetate | Acros | 78-39-7 | 13965-5000 |
| 2,6-Difluorobenzonitrile | FLROCHEM | 1897-52-5 | 1958 |
| 2-Chloro-6-fluorobenzonitrile | Aldrich | 668-45-1 | 188182 |
| 2,3,6-Trifluorobenzonitrile | Aldrich | 136514-17-5 | 310883 |
| 2,4,6-Trifluorobenzonitrile | Aldrich | 96606-37-0 | 548103 |
| C-((S)-C-Cyclopropyl-C-phenyl)-methylamine | Acesys | | A5011S |
| tert-Butyl carbazate | Aldrich | 870-46-2 | B9,100-5 |
| Propargyl bromide | Aldrich | 106-96-7 | P5.100-1 |
| 1-Iodo-3-fluoropropane | Apollo | 462-40-8 | PC1027 |
| 1-Fluoro-2-iodoethane | Apollo | 762-51-6 | PC0560 |
| 2-Iodo-1,1-difluoroethane | Apollo | 598-39-0 | PC1038 |
| 3-Iodobenzylamine | Aldrich | 696-40-2 | 100064 |
| 2-Fluoro-6-iodobenzonitrile | Fluorochem | 79544-29-9 | 6244 |
| Sodium nitrite | Aldrich | 7632-00-0 | 52,437-9 |
| Tetrabutylammonium bromide | Aldrich | 1643-19-2 | 19,311-9 |

30

Amines of the general formula VI used for the preparation of the compounds.

| Name | Supplier | CAS no. | Cat. no. |
|---|---|---|---|
| Cyclopentylamine | Acros | 1003-03-8 | 111591000 |
| Cyclobutylamine | Aldrich | 2516-34-9 | 225185 |
| Cyclopropylamine | Aldrich | 765-30-0 | 12,550-4 |
| Cyclohexylamine | Aldrich | 108-91-8 | 240648 |
| 2,2,2-Trifluoroethylhydrazine | Aldrich | 5042-30-8 | 129046 |
| 2,2,2-Trifluoroethylamine | Aldrich | 753-90-2 | 269042 |
| N-Aminopiperidine | Aldrich | 2213-43-6 | A75900 |
| tert-Butylhydrazine hydrochloride | Aldrich | 7400-27-3 | 194972 |
| Isopropylhydrazine | Matrix | 2257-52-5 | 19945 |
| Propylamine | Aldrich | 107-10-8 | 10,981-9 |
| Butylamine | Aldrich | 109-73-9 | B88985 |
| Isoamylamine | Aldrich | 107-85-7 | 126810 |
| 2-Methoxyethylamine | Aldrich | 109-85-3 | 143693 |
| Tetrahydrofurfurylamine | Aldrich | 4795-29-3 | 131911 |
| n-Amylamine | Aldrich | 110-58-7 | 171409 |
| 2-(Methylthio)ethylamine | Aldrich | 18542-42-2 | 632929 |
| Cyclobutylhydrazine | Enamine | — | — |
| Cyclopentylhydrazine | Enamine | — | — |
| Ethoxyamine hydrochloride | Aldrich | 3332-29-4 | 27,499-2 |
| O-iso-Butylhydroxylamine hydrochloride | ABCR | 6084-58-8 | TCI0387 |
| 1-(Aminooxy)propane chloride | ABCR | 6084-54-4 | KO12H-939 |
| Methylamine | Aldrich | 74-89-5 | 39,505-6 |
| Isopropylamine | Aldrich | 75-31-0 | 320366 |
| 2,2-Difluoropropylamine hydrochloride | Flrochem | 421-00-1 | 22069 |
| Isopropylamine | Aldrich | 75-31-0 | 320336 |
| Aminoacetonitrile hydrochloride | Lancaster | 6011-14-9 | 7658 |
| 3,3,3-Trifluoropropylamine | Flurochem | 2968-33-4 | 007712 |
| N-(2-Aminoethyl)pyrrolidine | Aldrich | 7154-73-6 | A55357 |
| Allylamine | Aldrich | 107-11-9 | 241075 |
| 3-Methoxypropylamine | Aldrich | 5332-73-0 | M2,500-7 |
| Propargylamine | Aldrich | 2450-71-7 | P5,090-0 |
| 5-Aminomethyl-pyrrolidin-2-one | Chembridge | 154148-69-3 | 4111537 |
| Cyclopropaneamine | Aldrich | 2516-47-4 | 359521 |
| 3-(Aminomethyl)piperidine | AB Chem | 23099-21-0 | AB1087 |
| Ethanolamine | Fluka | 141-43-5 | 02400 |
| (R)-3-Aminotetrahydrofuran | Milestone | 111769-26-7 | 7D-0006 |
| (S)-3-Aminotetrahydrofuran | Milestone | 104530-79-2 | 7D-0005 |

-continued

| Name | Supplier | CAS no. | Cat. no. |
|---|---|---|---|
| 4-Aminotetrahydropyrane | Combi-Blocks | 38041-19-9 | AM-1004-005 |
| (R)-2-(Aminomethyl-1-N-BOC-pyrrolidine | Flrochem | 259537-92-3 | 11384 |
| (S)-2-(Aminomethyl-1-N-BOC-pyrrolidine | Flrochem | 119020-01-8 | 11392 |
| (S)-3-Amino-1-N-BOC-pyrrolidine | Aldrich | 147081-44-5 | 634794 |
| (R)-3-Amino-1-N-BOC-pyrrolidine | CNH | 147081-49-0 | C-3153R |

Aldehydes used for reductive alkylation in examples 2 and 7:

| Name | Supplier | CAS no. | Cat. no. |
|---|---|---|---|
| Acetaldehyde | Aldrich | 75-07-0 | W200336 |
| Propionaldehyde | Acros | 123-38-6 | 13151 |
| Butyraldehyde | Aldrich | 123-72-8 | 53,819-1 |
| Isobutyraldehyde | Aldrich | 78-84-2 | 418110 |
| Trimethylacetaldehyde | Aldrich | 630-19-3 | T71501 |
| Cyclopropanecarboxaldehyde | Aldrich | 1489-69-6 | 272213 |
| Isovaleraldehyde | Aldrich | 590-86-3 | 146455 |
| Formaldehyde, 40% in water | Merck | 50-00-0 | 1.04003.1000 |

Example 12

NK3 Receptor Binding Assay

Membrane preparation: BHK cells stably expressing the human NK3 receptor were seeded in harvesting plates in Dulbeccos MEM containing GlutaMax (862 mg/l), 1 mM sodium pyruvate, 10% fetal calf serum, 1% Pen/Strep, 1 mg/ml G418 and were grown at 34° C. in a humidified atmosphere containing 10% $CO_2$. To increase receptor expression, 10 μM trichotatin A was added to the media 24 hours before harvest of the cells at a confluency of app 90%. Prior to the harvesting, the cells were washed twice with PBS without $Mg^{2+}$ og $Ca^{2+}$ and subsequently scrapped of in 10 ml PBS pr harvesting plate. The cells suspension were centrifuged at 1500×G in three minutes before resuspension in 15 mM Tris-HCl pH 7.5 buffer containing 2 mM $MgCl_2$; 0.3 mM EDTA and 1 mM EGTA (buffer A). The cell suspension was homogenised and subsequently centrifuged at 40000×G in 30 minutes. The membrane-pellet was resuspended in buffer A containing 250 mM sucrose, aliquoted and stored at −80° C.

Affinity assay description: The assay was performed as a SPA-based competition-binding assay in a 50 mM Tris pH 7.4 assay buffer containing 120 mM NaCl, 3 mM $MnCl_2$, 40 μg/ml bacitracin, 2 μg/ml Chymostatin, 1 μg/ml Phosphoramidon and 4 μg/ml Leupeptin. App 0.02 nM $^{125}$I-NKB was mixed with test compounds before addition of 40 μg of the homogenised NK3 membrane preparation and 0.025 mg SPA beads in a total volume of 60 μl. The assay plate was subsequently under agitation incubated for 90 min at RT. The plate was centrifugated 10 minutes at 500×G and counted in a topcounter 5 minutes per well.

The total binding, which comprised less than 5% of added radioligand, was defined using assay buffer whereas the non-specific binding was defined in the presence of 1 μM osanetant. The non-specific binding constituted app 5% of the total binding.

Data points were expressed in percent of the specific binding of $^{125}$I-NKB and the $IC_{50}$ values (concentration causing 50 percent inhibition of $^{125}$I-NKB specific binding) were determined by non-linear regression analysis using a sigmoidal variable slope curve fitting. The dissociation constant ($K_i$) were calculated from the Cheng Prusoff equation ($K_i=IC_{50}/(1+(L/K_D))$), where the concentration of free radioligand L is approximated to the concentration of added $^{125}$I-NKB in the assay (app 0.02 nM). The $K_D$ of $^{125}$I-NKB was determined to be 0.7 nM from three independent saturation assays each performed with duplicate determinations. Bmax was app 2 pmol/mg.

The compounds of the present invention generally have $K_i$ values of 1000 nM or less, such as 500 nM. Many compounds, in fact, have $K_i$ values below 100 nM and down to single digit values.

Example 13

NK3 Receptor Efficacy and Potency Assay

BHK cells stably expressing the human NK3 receptor were seeded in 100 μl media in black walled clear-base 96-wells plates (Costar) aiming at a confluency of 95-100% at the day of assay. The assay was performed according to the FLIPR Calcium 4 Assay kit (Molecular Devices). At the day of the assay, the media was removed and the cells were washed once with the HBSS buffer (Hanks BSS buffer, pH 7.4 containing 20 mM Hepes) before 100 μl of a solution of the calcium assay reagent dissolved in the HBSS buffer containing 2.5 mM probinicid was added to the cells. The plates were incubated for 60 min at 34° C., 10% $CO_2$ before use in the FLIPR for examination of fluorescence.

One representative plate was examined with a dose-response curve with NKB in a setup in which the wells initially were added HBSS buffer and 15 min later the various concentrations of NKB were added in order to determine the $EC_{50}$ and $EC_{85}$ of NKB. All compound plates used for NKB were precoated with a 1% BSA solution and subsequently washed three times with $H_2O$. NKB was diluted in HBSS buffer containing 0.1% BSA.

For efficacy and potency evaluation of compounds, these were diluted in HBSS buffer prior to test. For test of agonist activity, 25 μl of the diluted compound solution was added and the plate was analyzed for 5 minutes in the FLIPR. For test of antagonist activity, the plate was incubated for another 45 minutes before addition of 25 μl of the $EC_{85}$ concentration of NKB (app. 4 nM) as described above. The plates were subsequently analyzed for 5 minutes before the assay was terminated. The maximal increase in fluorescence over background following each ligand addition was determined. The $IC_{50}$ value was calculated using sigmoidal variable slope curve fitting, and the $cIC_{50}$ value was determined using the equation ($cIC_{50}=IC_{50}/(1+(EC_{85}/EC_{50}))$), where $EC_{85}$ and $EC_{50}$ for NKB were determined as described above.

Results

All isoquinolinones of the present invention characterized in the NK3 receptor efficacy and potency assay have been antagonists without any observed significant agonist activity at relevant doses. Table 1 shows the affinity and potency for the NK3 receptor.

TABLE 1

| Example | Affinity (K$_i$/nM) | Potency (cIC$_{50}$/nM) |
|---|---|---|
| 1a | 310 | 570 |
| 1q | 200 | 440 |
| 2d | 46 | 230 |
| 2e | 180 | 580 |
| 2h | 31 | 36 |
| 2p | 12 | 27 |
| 4f | 76 | 230 |
| 4l | 9.3 | 10 |
| 4p | 160 | 380 |
| 4r | 170 | 390 |
| 4t | 68 | 180 |
| 5d | 25 | 16 |
| 5g | 180 | 910 |
| 6a | 13 | 7 |
| 6b | 6.6 | 18 |
| 6e | 9.8 | 21 |
| 7a | 78 | 130 |
| 7i | 90 | 660 |
| 2i | 27 | |
| 2j | 23 | |
| 2q | 7.4 | |
| 2r | 6.8 | |
| 2s | 4.7 | |
| 2t | 43 | |
| 2w | 28 | |

Example 14

Free Fraction in Plasma

Free fraction in human plasma has been determined by equilibrium dialysis between human EDTA plasma (Bioreclamation) and 0.1M NaH$_2$PO$_4$ buffer adjusted to pH 7.4. The experiment was performed in a 96 well dialysis plate (HTD 96b, htdialysis). Plasma was frozen at −80° C. immediately after purchasing. Membranes (HTD 96a/b Dialysis Membrane Strips, MWCO 12-14 K, htdialysis) were soaked for one hour in pure PBS and kept in PBS/EtOH 80:20 (v/v) in a closed bottle at 5° C. until use.

Experiment:

Plasma was thawed in cold water and centrifuged 5 min at 3000 rpm before use to move potential clots. The plasma supernatant was transferred to a new tube. Test compounds were diluted to 0.2 mM in DMSO. Plasma was spiked 1:100 with test compound (final concentration 2 μM).

The dialysis plate was assembled with membranes according to the instructions whereupon 150 μL phosphate buffer was loaded to the lower side of the wells immediately after assembling and spiked plasma was loaded to the upper side of the wells. The plate was sealed with sealing tape and incubated at 37° C. with gently shaking in 5 hours.

After 5 hours incubation the plate was removed from the incubator. The sealing tape was carefully removed and 70 μL from the buffer wells ("lower" side) were transferred to 96 well plates for analysis.

Samples were analysed by LC-MS-MS on a Sciex API 4000 (Applied Biosystems).

Table 2 shows the plasma free fraction (%) for talnetant and 9 compounds of the present invention.

TABLE 2

| Example | Plasma free fraction (%) |
|---|---|
| Talnetant | 0.6 |
| 2a | 16.2 |
| 2h | 6.2 |
| 2k | 12.4 |
| 2i | 13.4 |
| 2s | 6.0 |
| 2t | 14.6 |
| 2w | 13.2 |
| 8c | 4.6 |
| 10a | 8.9 |

The invention claimed is:

1. A compound according to formula I

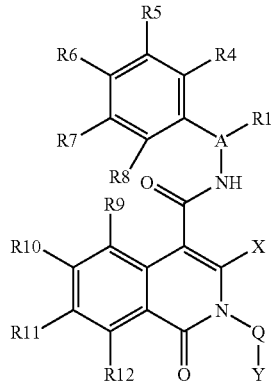

wherein A represents N, CH or CR$^1$;

each R$^1$ independently represents hydrogen, C$_{1-6}$alkyl, C$_{2-6}$alkenyl, C$_{2-6}$alkynyl, —C(O)—C$_{1-6}$alkyl, —C(O)—C$_{2-6}$alkenyl, —C(O)—C$_{2-6}$alkynyl, —C(O)—O—C$_{2-6}$alkenyl, —C(O)—O—C$_{2-6}$alkynyl or phenyl, wherein said phenyl, C$_{1-6}$alkyl, C$_{2-6}$alkenyl or C$_{2-6}$alkynyl is optionally substituted with one or more substituents selected from halogen, hydroxyl, haloC$_{1-6}$alkyl, nitro, C$_{1-6}$alkoxy, and NR$^2$R$^3$;

X represents hydrogen, C$_{1-6}$alkyl optionally substituted with F, or —CR$^a$R$^b$—X', wherein X' represents a monocyclic saturated moiety having 5-6 ring atoms one of which is N and wherein one or two additional ring atom may be a hetero atom selected from N, O and S, which monocyclic ring may be substituted with one or more substituent W, wherein W is selected from C$_{1-6}$alkyl, C$_{2-6}$alkenyl, C$_{2-6}$alkynyl, C$_{1-6}$haloalkyl or (=O);

R$^a$ and R$^b$ each individually represent hydrogen, —CH$_3$ or halogen;

Q represents a bond, —CH$_2$—, —NH—, or —O—;

Y represents C$_{1-6}$alkyl, C$_{2-6}$alkenyl or C$_{2-6}$alkynyl, wherein said alkyl, alkenyl or alkynyl may be substituted with one or more substituents P, wherein P is selected from halogen, hydroxy, C$_{1-6}$alkoxy, cyano, —S—C$_{1-6}$alkyl, and a monocyclic saturated moiety having 5-6 ring atoms one ring atom of which may be N and the rest is C; or Y may represent a monocyclic saturated moiety having 4-6 ring atoms, wherein one of said ring atoms may be selected from N and O, the rest being C, and which monocyclic saturated moiety may be substituted with one or more substituents Z, wherein Z is selected from $C_{1-6}$alkyl, $C_{2-6}$alkenyl, $C_{2-6}$alkynyl, (=O), C(O)H, —C(O)—$C_{1-6}$alkyl, halogen, $C_{1-6}$alkoxy, $C_{1-6}$hydroxyalkyl and hydroxy;

wherein each of $R^2$ and $R^3$ independently represents hydrogen, $C_{1-6}$alkyl, $C_{2-6}$alkenyl, $C_{2-6}$alkynyl, hydroxy$C_{1-6}$alkyl, or halo$C_{1-6}$alkyl;

each of $R^4$-$R^8$ and $R^9$-$R^{12}$ independently represents hydrogen, $C_{1-6}$alkyl, $C_{2-6}$alkenyl, $C_{2-6}$alkynyl, halogen, $NR^2R^3$, hydroxy, cyano, nitro, $C_{1-6}$alkoxy, halo$C_{1-6}$alkyl or hydroxy$C_{1-6}$alkyl;

provided said compound is different from 2-methyl-1-oxo-1,2-dihydro-isoquinoline-4-carboxylic acid (1-phenyl-ethyl)-amide;

or a pharmaceutically acceptable salt thereof.

2. The compound according to claim 1, wherein A represents CH.

3. The compound according to claim 1, wherein $R^1$ represents $C_{1-6}$alkyl.

4. The compound according to claim 3, wherein $R^1$ represents ethyl, cyclopropyl or cyclobutyl.

5. The compound according to claim 1, wherein X represents H, methyl optionally substituted with F, or —CH$_2$—X', wherein X' represents a monocyclic saturated moiety selected from piperazinyl and pyrrolidinyl, wherein said monocyclic moiety may be substituted with one or more substituents W, wherein W is selected from $C_{1-6}$alkyl and (=O).

6. The compound according to claim 1, wherein Q represents —CH$_2$— and Y represents $C_{1-4}$alkyl, $C_{2-4}$alkenyl or $C_{2-4}$alkynyl, and wherein P is selected from halogen, hydroxyl, —S—CH$_3$ and cyano.

7. The compound according to claim 1, wherein Q represents —CH$_2$— and Y represents a monocyclic saturated moiety having 4-6 ring atoms, wherein one of said ring atoms may be selected from N and O, the rest being C, and which monocyclic saturated moiety may be substituted with one or more substituents Z, wherein Z is selected from $C_{1-6}$alkyl, (=O), C(O)H, —C(O)—O—$C_{1-6}$alkyl, halogen, $C_{1-6}$alkoxy, $C_{1-6}$hydroxyalkyl and hydroxy.

8. The compound according to claim 1, wherein Q represents —NH— and Y represents $C_{1-6}$alkyl, wherein P is halogen, or wherein Y represents a monocyclic moiety having 4, 5 or 6 ring atoms, which ring atoms are selected from C.

9. The compound according to claim 1, wherein Q represents —O— and Y represents $C_{1-4}$alkyl.

10. The compound according to claim 1, wherein Q represents a bond and Y represents a monocyclic saturated moiety having 4-6 ring atoms, wherein 1 of said ring atoms may be selected from N and O, the rest being C, and which monocyclic saturated moiety may be substituted with one or more substituents Z, wherein Z is selected from $C_{1-6}$alkyl, (=O), halogen, and hydroxy.

11. The compound according to claim 1, wherein each of $R^4$-$R^8$ independently represents hydrogen or halogen.

12. The compound according to claim 11, wherein $R^7$ represents halogen and $R^4$, $R^5$ and $R^8$ represent hydrogen.

13. The compound according to claim 11, wherein all of $R^4$-$R^8$ represent hydrogen.

14. The compound according to claim 1, wherein each of $R^9$-$R^{12}$ independently represents hydrogen of halogen.

15. The compound according to claim 14, wherein $R^{12}$ represents halogen and $R^9$-$R^{11}$ represent hydrogen.

16. The compound according to claim 14, wherein all of $R^9$-$R^{12}$ represent hydrogen.

17. The compound according to claim 1 according to formula I'

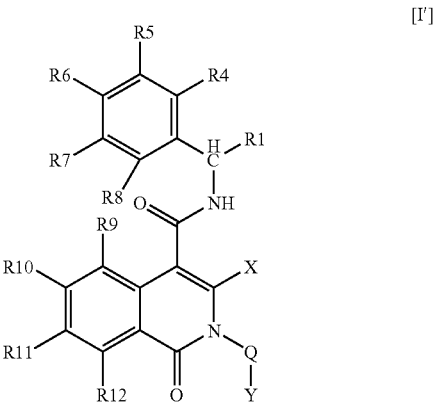

[I']

wherein $R^1$ represents $C_{1-6}$alkyl;

X represents hydrogen, $C_{1-6}$alkyl optionally substituted with F, or —CR$^a$R$^b$—X', wherein X' represents a monocyclic saturated moiety having 5-6 ring atoms one of which is N and wherein one or two additional ring atom may be a hetero atom selected from N, O and S, selected from piperazinyl and pyrrolidinyl, which monocyclic ring may be substituted with one or more substituent W, wherein W is selected from $C_{1-6}$alkyl or (=O);

$R^a$ and $R^b$ each individually represent hydrogen, —CH$_3$ or halogen;

Q represents a bond, —CH$_2$—, —NH—, —O—;

Y represents $C_{1-6}$alkyl, $C_{2-6}$alkenyl or $C_{2-6}$alkynyl, wherein said alkyl, alkenyl or alkynyl may be substituted with one or more substituents P, wherein P is selected from halogen, hydroxy, $C_{1-6}$alkoxy, cyano, —S—$C_{1-6}$alkyl, and a monocyclic saturated moiety having 5-6 ring atoms one ring atom of which may be N and the rest is C; or alternatively Y may represent a monocyclic saturated moiety having 4-6 ring atoms, wherein one of said ring atoms may be selected from N and O, the rest being C, and which monocyclic saturated moiety may be substituted with one or more substituents Z, wherein Z is selected from $C_{1-6}$alkyl, (=O), C(O)H, —C(O)—O—$C_{1-6}$alkyl, halogen, $C_{1-6}$alkoxy, $C_{1-6}$hydroxyalkyl and hydroxy;

each of $R^4$-$R^8$ and $R^9$-$R^{12}$ independently represents hydrogen, halogen, $C_{1-6}$alkoxy or $C_{1-6}$haloalkyl;

or a pharmaceutically acceptable salt thereof.

18. The compound according to claim 17 wherein $R^1$ represents ethyl, cyclopropyl or cyclobutyl;

X represents $C_{1-6}$alkyl optionally substituted with F, or —CH$_2$—X', wherein X' represents a monocyclic saturated moiety having 5-6 ring atoms one of which is N and wherein one or two additional ring atom may be a hetero atom selected from N, O and S, selected from piperazinyl and pyrrolidinyl, which monocyclic ring may be substituted with one or more substituent W, wherein W is selected from $C_{1-6}$alkyl or (=O);

Q represents —CH$_2$— or —NH—;

Y represents $C_{1-6}$alkyl, $C_{2-6}$alkenyl or $C_{2-6}$alkynyl all of which optionally substituted with up to three halogens, or alternatively Y represent a monocyclic saturated moiety having 4-6 ring atoms, wherein one of said ring atoms may be selected from N and O, the rest being C, and which monocyclic saturated moiety may be substituted with one or more substituents Z, wherein Z is selected from $C_{1-6}$alkyl;

each of $R^4$-$R^8$ and $R^9$-$R^{12}$ independently represents hydrogen, halogen, $C_{1-6}$alkoxy or $C_{1-6}$haloalkyl.

19. The compound according to claim 18, wherein each of $R^4$-$R^8$ and $R^9$-$R^{12}$ independently represents hydrogen or halogen.

20. The compound according to claim 19, wherein $R^7$ represents halogen, $R^5$, $R^6$ and $R^8$ represent hydrogen.

21. The compound according to claim 17 wherein $R^1$ represents ethyl, cyclopropyl or cyclobutyl;

X represents $C_{1-6}$alkyl optionally substituted with F, or —$CH_2$—X', wherein X' represents a monocyclic saturated moiety having 5-6 ring atoms one of which is N and wherein one or two additional ring atom may be a hetero atom selected from N, O and S, selected from piperazinyl and pyrrolidinyl, which monocyclic ring may be substituted with one or more substituent W, wherein W is selected from $C_{1-6}$alkyl or (=O);

Q represents —$CH_2$— or —NH—;

Y represents $C_{1-4}$alkyl, $C_{2-4}$alkenyl or $C_{2-4}$alkynyl, all of which optionally substituted with up to three halogens;

each of $R^4$-$R^8$ and $R^9$-$R^{12}$ independently represents hydrogen or halogen.

22. The compound according to claim 21, wherein $R^7$ and $R^{12}$ each independently represent halogen and $R^4$-$R^6$, $R^8$ and $R^9$-$R^{11}$ represent hydrogen.

23. The compound according to claim 1 selected from the list comprising 1a  2-Cyclopentyl-3-methyl-1-oxo-1,2-dihydro-isoquinoline-4-carboxylic acid ((S)-1-phenyl-propyl)-amide
1b  2-Cyclopropyl-3-methyl-1-oxo-1,2-dihydro-isoquinoline-4-carboxylic acid ((S)-1-phenyl-propyl)-amide
1c  2-Cyclobutyl-3-methyl-1-oxo-1,2-dihydro-isoquinoline-4-carboxylic acid ((S)-1-phenyl-propyl)-amide
1d  2-Cyclohexyl-3-methyl-1-oxo-1,2-dihydro-isoquinoline-4-carboxylic acid ((S)-1-phenyl-propyl)-amide
1e  3-Methyl-1-oxo-2-(2,2,2-trifluoro-ethylamino)-1,2-dihydro-isoquinoline-4-carboxylic acid ((S)-1-phenyl-propyl)-amide
1f  3-Methyl-1-oxo-2-(2,2,2-trifluoro-ethyl)-1,2-dihydro-isoquinoline-4-carboxylic acid ((S)-1-phenyl-propyl)-amide
1g  3-Methyl-1-oxo-2-piperidin-1-yl-1,2-dihydro-isoquinoline-4-carboxylic acid ((S)-1-phenyl-propyl)-amide
1h  2-tert-Butylamino-3-methyl-1-oxo-1,2-dihydro-isoquinoline-4-carboxylic acid ((S)-1-phenyl-propyl)-amide
1i  2-Isopropylamino-3-methyl-1-oxo-1,2-dihydro-isoquinoline-4-carboxylic acid ((S)-1-phenyl-propyl)-amide
1j  3-Methyl-2-morpholin-4-yl-1-oxo-1,2-dihydro-isoquinoline-4-carboxylic acid ((S)-1-phenyl-propyl)-amide
1k  3-Methyl-1-oxo-2-propyl-1,2-dihydro-isoquinoline-4-carboxylic acid ((S)-1-phenyl-propyl)-amide
1l  2-Butyl-3-methyl-1-oxo-1,2-dihydro-isoquinoline-4-carboxylic acid ((S)-1-phenyl-propyl)-amide
1m  3-Methyl-2-(3-methyl-butyl)-1-oxo-1,2-dihydro-isoquinoline-4-carboxylic acid ((S)-1-phenyl-propyl)-amide
1n  2-(2-Methoxy-ethyl)-3-methyl-1-oxo-1,2-dihydro-isoquinoline-4-carboxylic acid ((S)-1-phenyl-propyl)-amide
1o  3-Methyl-1-oxo-2-(tetrahydro-furan-2-ylmethyl)-1,2-dihydro-isoquinoline-4-carboxylic acid ((S)-1-phenyl-propyl)-amide
1p  3-Methyl-1-oxo-2-pentyl-1,2-dihydro-isoquinoline-4-carboxylic acid ((S)-1-phenyl-propyl)-amide
1q  3-Methyl-2-(2-methylsulfanyl-ethyl)-1-oxo-1,2-dihydro-isoquinoline-4-carboxylic acid ((S)-1-phenyl-propyl)-amide
1r  2-Ethoxy-3-methyl-1-oxo-1,2-dihydro-isoquinoline-4-carboxylic acid ((S)-1-phenyl-propyl)-amide
1s  2-Cyclobutylamino-8-fluoro-3-methyl-1-oxo-1,2-dihydro-isoquinoline-4-carboxylic acid ((S)-cyclopropyl-phenyl-methyl)-amide
1t  2-Cyclopentylamino-8-fluoro-3-methyl-1-oxo-1,2-dihydro-isoquinoline-4-carboxylic acid ((S)-cyclopropyl-phenyl-methyl)-amide
1u  2-Ethoxy-8-fluoro-3-methyl-1-oxo-1,2-dihydro-isoquinoline-4-carboxylic acid ((S)-cyclopropyl-phenyl-methyl)-amide
1v  8-Chloro-2-ethoxy-3-methyl-1-oxo-1,2-dihydro-isoquinoline-4-carboxylic acid ((S)-1-phenyl-propyl)-amide
1w  8-Chloro-2-isobutoxy-3-methyl-1-oxo-1,2-dihydro-isoquinoline-4-carboxylic acid ((S)-1-phenyl-propyl)-amide
1x  8-Chloro-3-methyl-1-oxo-2-propoxy-1,2-dihydro-isoquinoline-4-carboxylic acid ((S)-1-phenyl-propyl)-amide
1y  2,3-Dimethyl-1-oxo-1,2-dihydro-isoquinoline-4-carboxylic acid ((S)-1-phenyl-propyl)-amide
1z  2-Isopropyl-3-methyl-1-oxo-1,2-dihydro-isoquinoline-4-carboxylic acid ((S)-1-phenyl-propyl)-amide
1aa  2-(2,2-Difluoro-propyl)-3-methyl-1-oxo-1,2-dihydro-isoquinoline-4-carboxylic acid ((S)-1-phenyl-propyl)-amide
2a  2-Ethylamino-3-methyl-1-oxo-1,2-dihydro-isoquinoline-4-carboxylic acid ((S)-1-phenyl-propyl)-amide
2b  3-Methyl-1-oxo-2-propylamino-1,2-dihydro-isoquinoline-4-carboxylic acid ((S)-1-phenyl-propyl)-amide
2c  2-Butylamino-3-methyl-1-oxo-1,2-dihydro-isoquinoline-4-carboxylic acid ((S)-1-phenyl-propyl)-amide
2d  2-Isobutylamino-3-methyl-1-oxo-1,2-dihydro-isoquinoline-4-carboxylic acid ((S)-1-phenyl-propyl)-amide
2e  2-(2,2-Dimethyl-propylamino)-3-methyl-1-oxo-1,2-dihydro-isoquinoline-4-carboxylic acid ((S)-1-phenyl-propyl)-amide
2f  2-(Cyclopropylmethyl-amino)-3-methyl-1-oxo-1,2-dihydro-isoquinoline-4-carboxylic acid ((S)-1-phenyl-propyl)-amide
2g  3-Methyl-2-(3-methyl-butylamino)-1-oxo-1,2-dihydro-isoquinoline-4-carboxylic acid ((S)-1-phenyl-propyl)-amide
2h  8-Chloro-2-ethylamino-3-methyl-1-oxo-1,2-dihydro-isoquinoline-4-carboxylic acid ((S)-1-phenyl-propyl)-amide
2i  2-Ethylamino-8-fluoro-3-methyl-1-oxo-1,2-dihydro-isoquinoline-4-carboxylic acid ((S)-cyclopropyl-phenyl-methyl)-amide
2j  8-Fluoro-2-isobutylamino-3-methyl-1-oxo-1,2-dihydro-isoquinoline-4-carboxylic acid ((S)-cyclopropyl-phenyl-methyl)-amide
2k  8-Fluoro-3-methyl-1-oxo-2-propylamino-1,2-dihydro-isoquinoline-4-carboxylic acid ((S)-cyclopropyl-phenyl-methyl)-amide 2l 8-Chloro-3-methyl-1-oxo-2-propylamino-1,2-dihydro-isoquinoline-4-carboxylic acid ((S)-1-phenyl-propyl)-amide
2m 8-Chloro-2-isobutylamino-3-methyl-1-oxo-1,2-dihydro-isoquinoline-4-carboxylic acid ((S)-1-phenyl-propyl)-amide
2n 2-Ethylamino-1-oxo-3-(2-oxo-pyrrolidin-1-ylmethyl)-1,2-dihydro-isoquinoline-4-carboxylic acid ((S)-1-phenyl-propyl)-amide
2o 1-Oxo-3-(2-oxo-pyrrolidin-1-ylmethyl)-2-propylamino-1,2-dihydro-isoquinoline-4-carboxylic acid ((S)-1-phenyl-propyl)-amide
2p 2-Ethylamino-8-fluoro-3-methyl-1-oxo-1,2-dihydro-isoquinoline-4-carboxylic acid [(S)-cyclopropyl-(3-fluoro-phenyl)-methyl]-amide
2q 8-Fluoro-3-methyl-1-oxo-2-propylamino-1,2-dihydro-isoquinoline-4-carboxylic acid [(S)-cyclopropyl-(3-fluoro-phenyl)-methyl]-amide
2r 2-Ethylamino-8-fluoro-1-oxo-3-(2-oxo-pyrrolidin-1-ylmethyl)-1,2-dihydro-isoquinoline-4-carboxylic acid [(S)-cyclopropyl-(3-fluoro-phenyl)-methyl]-amide
2s 2-Ethylamino-8-fluoro-3-methyl-1-oxo-1,2-dihydro-isoquinoline-4-carboxylic acid [(S)-cyclobutyl-(3-fluoro-phenyl)-methyl]-amide
2t 2-Ethylamino-8-fluoro-3-methyl-1-oxo-1,2-dihydro-isoquinoline-4-carboxylic acid ((S)-1-phenyl-propyl)-amide
2u 8-Fluoro-3-methyl-2-methylamino-1-oxo-1,2-dihydro-isoquinoline-4-carboxylic acid ((S)-cyclopropyl-phenyl-methyl)-amide
2v 8-Fluoro-3-methyl-2-methylamino-1-oxo-1,2-dihydro-isoquinoline-4-carboxylic acid [(S)-cyclopropyl-(4-fluoro-phenyl)-methyl]-amide
2w 2-Ethylamino-8-fluoro-3-methyl-1-oxo-1,2-dihydro-isoquinoline-4-carboxylic acid [(S)-cyclopropyl-(4-fluoro-phenyl)-methyl]-amide
2x 8-Fluoro-3-methyl-2-methylamino-1-oxo-1,2-dihydro-isoquinoline-4-carboxylic acid [(S)-cyclopropyl-(3,4-difluoro-phenyl)-methyl]-amide
2y 2-Ethylamino-8-fluoro-3-methyl-1-oxo-1,2-dihydro-isoquinoline-4-carboxylic acid [(S)-cyclopropyl-(3,4-difluoro-phenyl)-methyl]-amide
2z 8-Fluoro-3-methyl-2-methylamino-1-oxo-1,2-dihydro-isoquinoline-4-carboxylic acid [(S)-cyclobutyl-(3,4-difluoro-phenyl)-methyl]-amide
2aa 2-Ethylamino-8-fluoro-3-methyl-1-oxo-1,2-dihydro-isoquinoline-4-carboxylic acid [(S)-cyclobutyl-(3,4-difluoro-phenyl)-methyl]-amide
2ab 8-Iodo-3-methyl-1-oxo-2-propylamino-1,2-dihydro-isoquinoline-4-carboxylic acid [(S)-cyclobutyl-(3-fluoro-phenyl)-methyl]-amide
2ac 8-Fluoro-3-methyl-1-oxo-2-propylamino-1,2-dihydro-isoquinoline-4-carboxylic acid 3-iodo-benzylamide
3a 8-Fluoro-3-methyl-1-oxo-2-propyl-1,2-dihydro-isoquinoline-4-carboxylic acid [(S)-cyclopropyl-(3-fluoro-phenyl)-methyl]-amide
3b 8-Chloro-3-methyl-1-oxo-2-propyl-1,2-dihydro-isoquinoline-4-carboxylic acid [(S)-cyclopropyl-(3-fluoro-phenyl)-methyl]-amide
3c 8-Fluoro-3-methyl-1-oxo-2-propyl-1,2-dihydro-isoquinoline-4-carboxylic acid [(S)-cyclobutyl-(3-fluoro-phenyl)-methyl]-amide
3d 5,8-Difluoro-3-methyl-1-oxo-2-propyl-1,2-dihydro-isoquinoline-4-carboxylic acid [(S)-cyclopropyl-(3-fluoro-phenyl)-methyl]-amide
4a 8-Fluoro-2,3-dimethyl-1-oxo-1,2-dihydro-isoquinoline-4-carboxylic acid [(S)-cyclopropyl-(3-fluoro-phenyl)-methyl]-amide
4b 8-Fluoro-2-isopropyl-3-methyl-1-oxo-1,2-dihydro-isoquinoline-4-carboxylic acid [(S)-cyclopropyl-(3-fluoro-phenyl)-methyl]-amide
4c 2-Cyanomethyl-8-fluoro-3-methyl-1-oxo-1,2-dihydro-isoquinoline-4-carboxylic acid [(S)-cyclopropyl-(3-fluoro-phenyl)-methyl]-amide
4d 8-Fluoro-3-methyl-1-oxo-2-(3,3,3-trifluoro-propyl)-1,2-dihydro-isoquinoline-4-carboxylic acid [(S)-cyclopropyl-(3-fluoro-phenyl)-methyl]-amide
4e 2-(2,2-Difluoro-propyl)-8-fluoro-3-methyl-1-oxo-1,2-dihydro-isoquinoline-4-carboxylic acid [(S)-cyclopropyl-(3-fluoro-phenyl)-methyl]-amide
4f 8-Fluoro-2-(2-methoxy-ethyl)-3-methyl-1-oxo-1,2-dihydro-isoquinoline-4-carboxylic acid [(S)-cyclopropyl-(3-fluoro-phenyl)-methyl]-amide
4g 8-Fluoro-3-methyl-1-oxo-2-(2-pyrrolidin-1-yl-ethyl)-1,2-dihydro-isoquinoline-4-carboxylic acid [(S)-cyclopropyl-(3-fluoro-phenyl)-methyl]-amide
8-Fluoro-3-methyl-2-(2-morpholin-4-yl-ethyl)-1-oxo-1,2-dihydro-isoquinoline-4-carboxylic acid [(S)-cyclopropyl-(3-fluoro-phenyl)-methyl]-amide
4h 2-Allyl-3-methyl-1-oxo-1,2-dihydro-isoquinoline-4-carboxylic acid ((S)-1-phenyl-propyl)-amide
8-Fluoro-3-methyl-2-(3-morpholin-4-yl-propyl)-1-oxo-1,2-dihydro-isoquinoline-4-carboxylic acid [(S)-cyclopropyl-(3-fluoro-phenyl)-methyl]-amide
4i 2-(3-Methoxy-propyl)-3-methyl-1-oxo-1,2-dihydro-isoquinoline-4-carboxylic acid ((S)-1-phenyl-propyl)-amide
4j 6,8-Difluoro-3-methyl-1-oxo-2-(3,3,3-trifluoro-propyl)-1,2-dihydro-isoquinoline-4-carboxylic acid [(S)-cyclopropyl-(3-fluoro-phenyl)-methyl]-amide
8-Fluoro-3-methyl-1-oxo-2-(2-oxo-oxazolidine-3-yl)-1,2-dihydro-isoquinoline-4-carboxylic acid [(S)-cyclopropyl-(3-fluoro-phenyl)-methyl]-amide
4k 3-Methyl-1-oxo-2-prop-2-ynyl-1,2-dihydro-isoquinoline-4-carboxylic acid ((S)-1-phenyl-propyl)-amide
4l 8-Fluoro-1-oxo-3-(2-oxo-pyrrolidin-1-ylmethyl)-2-(3,3,3-trifluoro-propyl)-1,2-dihydro-isoquinoline-4-carboxylic acid [(S)-cyclopropyl-(3-fluoro-phenyl)-methyl]-amide
4m 2-Cyclopropylmethyl-8-fluoro-3-methyl-1-oxo-1,2-dihydro-isoquinoline-4-carboxylic acid [(S)-cyclopropyl-(3-fluoro-phenyl)-methyl]-amide
4n 8-Fluoro-3-methyl-1-oxo-2-(5-oxo-pyrrolidin-2-ylmethyl)-1,2-dihydro-isoquinoline-4-carboxylic acid [(S)-cyclopropyl-(3-fluoro-phenyl)-methyl]-amide
4o 8-Fluoro-3-methyl-1-oxo-2-piperidin-3-ylmethyl-1,2-dihydro-isoquinoline-4-carboxylic acid [(S)-cyclopropyl-(3-fluoro-phenyl)-methyl]-amide
4p 8-Fluoro-2-(2-hydroxy-ethyl)-3-methyl-1-oxo-1,2-dihydro-isoquinoline-4-carboxylic acid [(S)-cyclobutyl-(3-fluoro-phenyl)-methyl]-amide
4q 8-Fluoro-3-methyl-1-oxo-2-(R)-tetrahydro-furan-3-yl-1,2-dihydro-isoquinoline-4-carboxylic acid [(S)-cyclobutyl-(3-fluoro-phenyl)-methyl]-amide
4r 8-Fluoro-3-methyl-1-oxo-2-(S)-tetrahydro-furan-3-yl-1,2-dihydro-isoquinoline-4-carboxylic acid [(S)-cyclobutyl-(3-fluoro-phenyl)-methyl]-amide
4s 8-Fluoro-3-methyl-1-oxo-2-(tetrahydro-pyran-4-yl)-1,2-dihydro-isoquinoline-4-carboxylic acid [(S)-cyclobutyl-(3-fluoro-phenyl)-methyl]-amide 4t  2-Ethoxy-8-fluoro-3-methyl-1-oxo-1,2-dihydro-isoquinoline-4-carboxylic acid [(S)-cyclobutyl-(3-fluoro-phenyl)-methyl]-amide 4u  8-Fluoro-3-methyl-1-oxo-2-propoxy-1,2-dihydro-isoquinoline-4-carboxylic acid [(S)-cyclobutyl-(3-fluoro-phenyl)-methyl]-amide 4v  2-Ethoxy-8-fluoro-3-methyl-1-oxo-1,2-dihydro-isoquinoline-4-carboxylic acid [(S)-cyclopropyl-(3-fluoro-phenyl)-methyl]-amide 4w  8-Fluoro-3-methyl-1-oxo-2-propoxy-1,2-dihydro-isoquinoline-4-carboxylic acid [(S)-cyclopropyl-(3-fluoro-phenyl)-methyl]-amide 4x  2-Allyl-8-fluoro-3-methyl-1-oxo-1,2-dihydro-isoquinoline-4-carboxylic acid [(S)-cyclobutyl-(3-fluoro-phenyl)-methyl]-amide 4y  2-Allyl-8-fluoro-3-methyl-1-oxo-1,2-dihydro-isoquinoline-4-carboxylic acid [(S)-cyclopropyl-(3-fluoro-phenyl)-methyl]-amide 4z  8-Fluoro-3-methyl-1-oxo-2-prop-2-ynyl-1,2-dihydro-isoquinoline-4-carboxylic acid [(S)-cyclobutyl-(3-fluoro-phenyl)-methyl]-amide 4aa  8-Fluoro-3-methyl-1-oxo-2-prop-2-ynyl-1,2-dihydro-isoquinoline-4-carboxylic acid [(S)-cyclopropyl-(3-fluoro-phenyl)-methyl]-amide 4ab  2-Cyclopropylmethyl-8-fluoro-3-methyl-1-oxo-1,2-dihydro-isoquinoline-4-carboxylic acid [(S)-cyclobutyl-(3-fluoro-phenyl)-methyl]-amide 5a  8-Fluoro-3-methyl-1-oxo-2-(S)-1-pyrrolidin-2-ylmethyl-1,2-dihydro-isoquinoline-4-carboxylic acid [(S)-cyclobutyl-(3-fluoro-phenyl)-methyl]-amide 5b  8-Fluoro-3-methyl-1-oxo-2-(R)-1-pyrrolidin-3-ylmethyl-1,2-dihydro-isoquinoline-4-carboxylic acid [(S)-cyclobutyl-(3-fluoro-phenyl)-methyl]-amide 5c  8-Fluoro-3-methyl-1-oxo-2-(S)-1-pyrrolidin-3-ylmethyl-1,2-dihydro-isoquinoline-4-carboxylic acid [(S)-cyclobutyl-(3-fluoro-phenyl)-methyl]-amide 5d  8-Fluoro-3-methyl-1-oxo-2-(R)-1-pyrrolidin-2-ylmethyl-1,2-dihydro-isoquinoline-4-carboxylic acid [(S)-cyclobutyl-(3-fluoro-phenyl)-methyl]-amide 5e  8-Fluoro-3-methyl-1-oxo-2-(S)-1-pyrrolidin-2-ylmethyl-1,2-dihydro-isoquinoline-4-carboxylic acid [(S)-cyclopropyl-(3-fluoro-phenyl)-methyl]-amide 5f  8-Fluoro-3-methyl-1-oxo-2-(R)-1-pyrrolidin-2-ylmethyl-1,2-dihydro-isoquinoline-4-carboxylic acid [(S)-cyclopropyl-(3-fluoro-phenyl)-methyl]-amide 5g  8-Fluoro-3-methyl-1-oxo-2-(R)-pyrrolidin-3-yl-1,2-dihydro-isoquinoline-4-carboxylic acid [(S)-cyclopropyl-(3-fluoro-phenyl)-methyl]-amide 5h  8-Fluoro-3-methyl-1-oxo-2-(S)-pyrrolidin-3-yl-1,2-dihydro-isoquinoline-4-carboxylic acid [(S)-cyclopropyl-(3-fluoro-phenyl)-methyl]-amide 6a  8-Fluoro-1-oxo-3-piperazin-1-ylmethyl-2-propyl-1,2-dihydro-isoquinoline-4-carboxylic acid [(S)-cyclopropyl-(3-fluoro-phenyl)-methyl]-amide 6b  8-Fluoro-1-oxo-3-piperazin-1-ylmethyl-2-propyl-1,2-dihydro-isoquinoline-4-carboxylic acid [(S)-cyclobutyl-(3-fluoro-phenyl)-methyl]-amide 6c  3-(4-tert-Butyl-piperazin-1-ylmethyl)-8-chloro-1-oxo-2-propyl-1,2-dihydro-isoquinoline-4-carboxylic acid [(S)-cyclopropyl-(3-fluoro-phenyl)-methyl]amide 6d  8-Chloro-1-oxo-3-(2-oxo-pyrrolidin-1-ylmethyl)-2-propyl-1,2-dihydro-isoquinoline-4-carboxylic acid [(S)-cyclopropyl-(3-fluoro-phenyl)-methyl]-amide 6e  8-Fluoro-1-oxo-3-(2-oxo-pyrrolidin-1-ylmethyl)-2-propyl-1,2-dihydro-isoquinoline-4-carboxylic acid [(S)-cyclopropyl-(3-fluoro-phenyl)-methyl]-amide 6f  3-(4-tert-Butyl-piperazin-1-ylmethyl)-8-fluoro-1-oxo-2-propyl-1,2-dihydro-isoquinoline-4-carboxylic acid [(S)-cyclopropyl-(3-fluoro-phenyl)-methyl]-amide 6g  3-((2R,5S)-2,5-Dimethyl-piperazin-1-ylmethyl)-8-fluoro-1-oxo-2-(3,3,3-trifluoro-propyl)-1,2-dihydro-isoquinoline-4-carboxylic acid [(S)-cyclopropyl-(3-fluoro-phenyl)-methyl]-amide 7a  8-Fluoro-3-methyl-2-((S)-1-methyl-pyrrolidin-2-ylmethyl)-1-oxo-1,2-dihydro-isoquinoline-4-carboxylic acid [(S)-cyclopropyl-(3-fluoro-phenyl)-methyl]-amide 7b  2-((S)-1-Ethyl-pyrrolidin-2-ylmethyl)-8-fluoro-3-methyl-1-oxo-1,2-dihydro-isoquinoline-4-carboxylic acid [(S)-cyclopropyl-(3-fluoro-phenyl)-methyl]-amide 7c  8-Fluoro-3-methyl-1-oxo-2-((S)-1-propyl-pyrrolidin-2-ylmethyl)-1,2-dihydro-isoquinoline-4-carboxylic acid [(S)-cyclopropyl-(3-fluoro-phenyl)-methyl]-amide 7d  2-((S)-1-Acetyl-pyrrolidin-2-ylmethyl)-8-fluoro-3-methyl-1-oxo-1,2-dihydro-isoquinoline-4-carboxylic acid [(S)-cyclopropyl-(3-fluoro-phenyl)-methyl]-amide 7e  8-Fluoro-3-methyl-2-((R)-1-methyl-pyrrolidin-2-ylmethyl)-1-oxo-1,2-dihydro-isoquinoline-4-carboxylic acid [(S)-cyclopropyl-(3-fluoro-phenyl)-methyl]-amide 7f  2-((R)-1-Ethyl-pyrrolidin-2-ylmethyl)-8-fluoro-3-methyl-1-oxo-1,2-dihydro-isoquinoline-4-carboxylic acid [(S)-cyclopropyl-(3-fluoro-phenyl)-methyl]-amide 7g  8-Fluoro-3-methyl-1-oxo-2-((R)-1-propyl-pyrrolidin-2-ylmethyl)-1,2-dihydro-isoquinoline-4-carboxylic acid [(S)-cyclopropyl-(3-fluoro-phenyl)-methyl]-amide 7h  2-((R)-1-Acetyl-pyrrolidin-2-ylmethyl)-8-fluoro-3-methyl-1-oxo-1,2-dihydro-isoquinoline-4-carboxylic acid [(S)-cyclopropyl-(3-fluoro-phenyl)-methyl]-amide 7i  8-Fluoro-3-methyl-2-((R)-1-methyl-pyrrolidin-3-yl)-1-oxo-1,2-dihydro-isoquinoline-4-carboxylic acid [(S)-cyclopropyl-(3-fluoro-phenyl)-methyl]-amide 7j  8-Fluoro-3-methyl-2-((S)-1-methyl-pyrrolidin-2-ylmethyl)-1-oxo-1,2-dihydro-isoquinoline-4-carboxylic acid [(S)-cyclobutyl-(3-fluoro-phenyl)-methyl]amide 7k  2-((S)-1-Ethyl-pyrrolidin-2-ylmethyl)-8-fluoro-3-methyl-1-oxo-1,2-dihydro-isoquinoline-4-carboxylic acid [(S)-cyclobutyl-(3-fluoro-phenyl)-methyl]-amide 7l  8-Fluoro-3-methyl-2-(R)-1-methyl-pyrrolidin-2-ylmethyl)-1-oxo-1,2-dihydro-isoquinoline-4-carboxylic acid [(S)-cyclobutyl-(3-fluoro-phenyl)-methyl]-amide 8a  2-Ethylamino-8-fluoro-3-methyl-1-oxo-1,2-dihydro-isoquinoline-4-carboxylic acid [(S)-1-(4-fluoro-phenyl)-propyl]-amide 8b  2-Ethylamino-8-fluoro-3-methyl-1-oxo-1,2-dihydro-isoquinoline-4-carboxylic acid [(S)-cyclobutyl-(4-fluoro-phenyl)-methyl]-amide 8c  8-Fluoro-3-methyl-1-oxo-2-propylamino-1,2-dihydro-isoquinoline-4-carboxylic acid [(S)-cyclobutyl-(3-fluoro-phenyl)-methyl]-amide 9a  8-Fluoro-3-fluoromethyl-1-oxo-2-propylamino-1,2-dihydro-isoquinoline-4-carboxylic acid [(S)-cyclobutyl-(3-fluoro-phenyl)-methyl]-amide 10a  8-Fluoro-2-(3-fluoro-propylamino)-3-methyl-1-oxo-1,2-dihydro-isoquinoline-4-carboxylic acid [(S)-cyclobutyl-(3-fluoro-phenyl)-methyl]-amide 10b  8-Fluoro-2-(2-fluoro-ethylamino)-3-methyl-1-oxo-1,2-dihydro-isoquinoline-4-carboxylic acid [(S)-cyclobutyl-(3-fluoro-phenyl)-methyl]-amide 10c  2-(2,2-Difluoro-ethylamino)-8-fluoro-3-methyl-1-oxo-1,2-dihydro-isoquinoline-4-carboxylic acid [(S)-cyclobutyl-(3-fluoro-phenyl)-methyl]-amide 10d  8-Fluoro-3-methyl-1-oxo-2-prop-2-ynylamino-1,2-dihydro-isoquinoline-4-carboxylic acid [(S)-cyclobutyl-(3-fluoro-phenyl)-methyl]-amide 11a 2-Ethylamino-8-hydroxy-3-methyl-1-oxo-1,2-dihydro-isoquinoline-4-carboxylic acid ((S)-cyclopropyl-phenyl-methyl)-amide, or a pharmaceutically acceptable salt thereof.

24. The compound according to claim 17 wherein each C can be the $^{11}$C isotope and each F can be the $^{18}$F isotope, wherein said compound comprises at least one of said isotopes;

or a pharmaceutically acceptable salt thereof.

25. The compound according to claim 24 selected from the list comprising 2-((1-$^{11}$C)-Ethylamino)-8-fluoro-3-methyl-1-oxo-1,2-dihydro-isoquinoline-4-carboxylic acid [(S)-cyclobutyl-(3-fluoro-phenyl)-methyl]-amide 8-Fluoro-3-methyl-1-oxo-2-((1-$^{11}$C)-propylamino)-1,2-dihydro-isoquinoline-4-carboxylic acid [(S)-cyclobutyl-(3-fluoro-phenyl)-methyl]-amide 2-Ethylamino-8-fluoro-3-($^{18}$F)-fluoromethyl-1-oxo-1,2-dihydro-isoquinoline-4-carboxylic acid [(S)-cyclobutyl-(3-fluoro-phenyl)-methyl]-amide 8-Fluoro-3-($^{18}$F)-fluoromethyl-1-oxo-2-propylamino-1,2-dihydro-isoquinoline-4-carboxylic acid [(S)-cyclobutyl-(3-fluoro-phenyl)-methyl]-amide 2-Ethylamino-8-($^{18}$F)-fluoro-3-methyl-1-oxo-1,2-dihydro-isoquinoline-4-carboxylic acid [(S)-cyclobutyl-(3-fluoro-phenyl)-methyl]-amide 8-($^{18}$F)-Fluoro-3-methyl-1-oxo-2-propylamino-1,2-dihydro-isoquinoline-4-carboxylic acid [(S)-cyclobutyl-(3-fluoro-phenyl)-methyl]-amide 2-Ethylamino-8-fluoro-3-methyl-1-oxo-1,2-dihydro-isoquinoline-4-($^{11}$C)-carboxylic acid [(S)-cyclobutyl-(3-fluoro-phenyl)-methyl]-amide 8-Fluoro-3-methyl-1-oxo-2-propylamino-1,2-dihydro-isoquinoline-4-($^{11}$C)-carboxylic acid [(S)-cyclobutyl-(3-fluoro-phenyl)-methyl]-amide 2-Ethylamino-8-fluoro-3-methyl-1-oxo-1,2-dihydro-isoquinoline-4-carboxylic acid [(S)-cyclobutyl-(3-($^{18}$F)-fluoro-phenyl)-methyl]-amide 8-Fluoro-3-methyl-1-oxo-2-propylamino-1,2-dihydro-isoquinoline-4-carboxylic acid [(S)-cyclobutyl-(3-($^{18}$F)-fluoro-phenyl)-methyl]-amide 8-Fluoro-2-(3-($^{18}$F)-fluoro-propylamino)-3-methyl-1-oxo-1,2-dihydro-isoquinoline-4-carboxylic acid [(S)-cyclobutyl-(3-fluoro-phenyl)-methyl]-amide 8-Fluoro-2-(3-($^{18}$F)-fluoro-propylamino)-3-methyl-1-oxo-1,2-dihydro-isoquinoline-4-carboxylic acid [(S)-cyclopropyl-(3-fluoro-phenyl)-methyl]-amide 8-Fluoro-3-methyl-1-oxo-2-propylamino-1,2-dihydro-isoquinoline-4-carboxylic acid [(S)-cyclopropyl-(3-($^{18}$F)-fluoro-phenyl)-methyl]-amide.

26. A pharmaceutical composition comprising a compound according to claim 1 in combination with one or more pharmaceutically acceptable carrier or excipient.

27. A method for the treatment of a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder; schizoid personality disorder; schizotypal personality disorder; psychosis or schizophrenia associated with major depression, bipolar disorder, Alzheimer's disease or Parkinson's disease; major depression; general anxiety disorder; bipolar disorder; mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; inflammatory bowel syndrome; PTSD; dementia and agitation and delirium in the elderly, said method comprising the administration of a therapeutically effective amount of a compound according to claim 1 to a patient in need thereof.

28. The method according to claim 27, wherein said disease is schizophrenia.

29. The method according to claim 28, wherein positive, negative and/or cognitive symptoms are treated.

30. The method according to claim 27 wherein the substance or drug induced psychotic disorder is cocaine, alcohol, or amphetamine.

31. The method according to claim 27 wherein the bipolar disorder is maintenance treatment, recurrence prevention and stabilization.

* * * * *